United States Patent
Miyoshi et al.

(10) Patent No.: US 8,858,428 B2
(45) Date of Patent: Oct. 14, 2014

(54) ENDOSCOPE AND ROTARY SELF-PROPELLED ENDOSCOPE

(75) Inventors: Hiroaki Miyoshi, Fuchu (JP); Satoshi Makiyama, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1602 days.

(21) Appl. No.: 12/168,610

(22) Filed: Jul. 7, 2008

(65) Prior Publication Data

US 2008/0262309 A1 Oct. 23, 2008

Related U.S. Application Data

(63) Continuation of application No. PCT/JP2007/050183, filed on Jan. 10, 2007.

(30) Foreign Application Priority Data

| Jan. 13, 2006 | (JP) | ................................ | 2006-006778 |
| Jan. 13, 2006 | (JP) | ................................ | 2006-006779 |
| Jan. 13, 2006 | (JP) | ................................ | 2006-006780 |

(51) Int. Cl.
| A61B 1/00 | (2006.01) |
| A61M 25/092 | (2006.01) |
| A61B 1/005 | (2006.01) |
| G02B 23/24 | (2006.01) |

(52) U.S. Cl.
CPC ............. *A61B 1/0052* (2013.01); *A61B 1/0057* (2013.01); *G02B 23/2476* (2013.01); *A61B 1/0016* (2013.01)
USPC ......................................... 600/146; 600/136

(58) Field of Classification Search
USPC .............. 600/136–142, 144–150, 152; 606/1, 606/108; 604/528, 529
See application file for complete search history.

(56) References Cited

U.S. PATENT DOCUMENTS

| 3,187,841 | A | * | 6/1965 | Renshaw | ....................... | 187/234 |
| 3,892,228 | A | * | 7/1975 | Mitsui | ........................... | 600/149 |
| 4,655,257 | A | * | 4/1987 | Iwashita | ....................... | 138/120 |
| 4,919,112 | A | * | 4/1990 | Siegmund | ..................... | 600/136 |
| 5,159,446 | A |   | 10/1992 | Hibino et al. | | |
| 2003/0040657 | A1 |   | 2/2003 | Yamaya et al. | | |

FOREIGN PATENT DOCUMENTS

| JP | 5-20704 | 3/1993 |
| JP | 10-113396 | 5/1998 |
| WO | 2005/110194 | 11/2005 |

OTHER PUBLICATIONS

Supplementary European Search Report dated Jan. 23, 2012 from corresponding European Application No. EP 07 70 6530.8.

* cited by examiner

*Primary Examiner* — Anhtuan T Nguyen
*Assistant Examiner* — Aaron B Fairchild
(74) *Attorney, Agent, or Firm* — Scully, Scott, Murphy & Presser, PC

(57) ABSTRACT

An endoscope of the present invention includes an insertion portion including a bending portion, an operation portion separate from the insertion portion, a bending operation wire that is inserted through the insertion portion and used for bending the bending portion in a predetermined direction with tugging in a forward/backward tugging direction, and connecting mechanisms that makes it possible to couple the insertion portion and the operation portion in a manner in which the bending wire is freely tugged in the operation portion.

5 Claims, 72 Drawing Sheets

ENDOSCOPE AND ROTARY SELF-PROPELLED ENDOSCOPE

CROSS REFERENCE TO RELATED APPLICATION

This application is a continuation application of PCT/JP2007/050183 filed on Jan. 10, 2007 and claims the benefit of Japanese Applications No. 2006-006778 filed in Japan on Jan. 13, 2006, and No. 2006-006779 filed in Japan on Jan. 13, 2006, and No. 2006-006780 filed in Japan on Jan. 13, 2006, the entire contents of each of which are incorporated herein by their reference.

BACKGROUND OF THE INVENTION

1. Field of the Invention

The present invention relates to an endoscope, an insertion portion and an operation portion of which are detachably attachable, and a rotary self-propelled endoscope.

2. Description of the Related Art

As is well known, endoscopes are used in various fields such as medical and industrial fields for the purpose of observing regions that cannot be visually observed directly such as the inside of tracts. In general, the endoscopes include slim and long insertion portions that are inserted into test regions.

As such endoscopes, those having various configurations are known. As an example, there is known a rotary self-propelled endoscope that is an endoscope, an insertion portion of which is inserted into the large intestine through the anus, and in which a rotary cylinder rotatable around a shaft including a spiral shape portion is provided on an outer periphery of the insertion portion and the insertion of the insertion portion into the large intestine can be automatically performed with a screw action by using friction generated between the spiral shape portion and the intestinal wall by rotating the rotary cylinder with a motor or the like.

The technique for inserting a medical instrument such as an endoscope into the body cavity using friction of a rotating member and a tissue in the body cavity is disclosed in, for example, Japanese Patent Application Laid-Open No. 10-113396. In Japanese Patent Application Laid-Open No. 10-113396, a propelling device for a medical apparatus that can easily and less invasively guide the medical apparatus to the depth of the organism tube is described.

In the propelling device, a rib oblique to an axial direction of a rotating member is provided in the rotating member. Therefore, by rotating the rotating member, the torque of the rotating member is converted into thrust by the rib and the medical apparatus coupled to the propelling device is moved in a depth direction by the thrust.

As endoscopes employing such a technique, there are various types. As an example, there is a rotary self-propelled endoscope that is an endoscope inserted into the large intestine through the anus and in which a rotary cylinder having flexibility rotatable around an axis is provided on an outer periphery side of an insertion portion and the insertion portion can be automatically inserted into the body cavity by rotating the rotary cylinder. The rotary cylinder is long because the rotary cylinder is inserted into the body cavity. As a material of the rotary cylinder, metal with high rotation transmissivity is used.

Regardless of the rotary self-propelled endoscopes, it is preferable that an insertion portion and an operation portion are detachably attachable to a medical endoscope from the viewpoints of storability in nonuse and sterilization and disinfection workability after use.

Therefore, for example, Japanese Utility Model Application Laid-Open Publication 5-20704 discloses a manual-operation-portion detachable endoscope, a manual operation portion and a main body of which can be separated.

SUMMARY OF THE INVENTION

An endoscope according to the present invention includes an insertion portion including a bending portion, an operation portion separate from the insertion portion, a bending operation wire that is inserted into the insertion portion and used for bending the bending portion in a predetermined direction with tugging in a forward/backward tugging direction, and a connecting mechanism that makes it possible to couple the insertion portion and the operation portion in a manner in which the bending wire is freely tugged in the operation portion.

DETAILED DESCRIPTION OF THE PREFERRED EMBODIMENT(S)

An embodiment of the present invention will be hereinafter explained with reference to the drawings.

Figure 1:
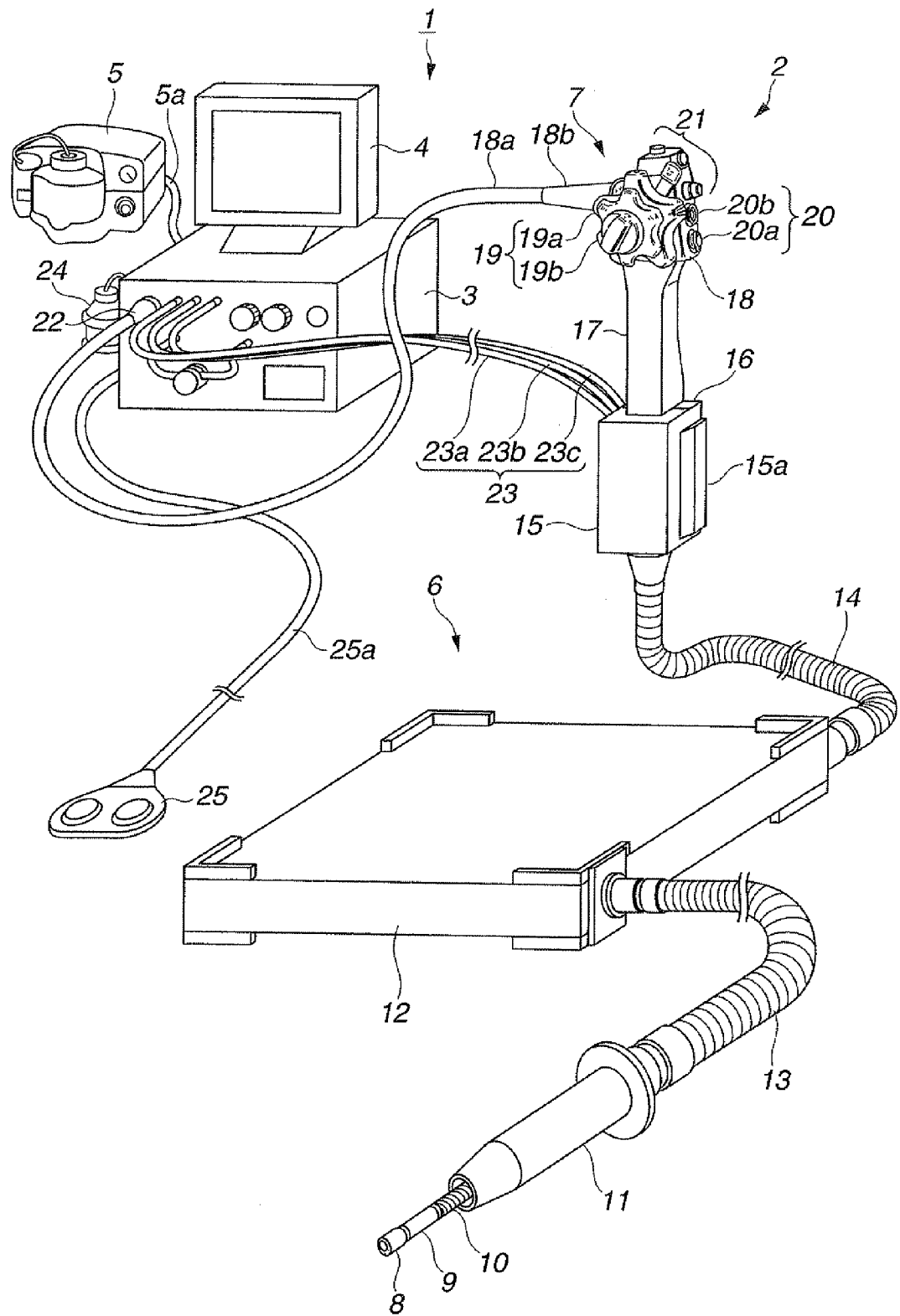
FIG. 1 is an overall diagram of a rotary self-propelled endoscope system according to an embodiment of the present invention.
Figure 2:
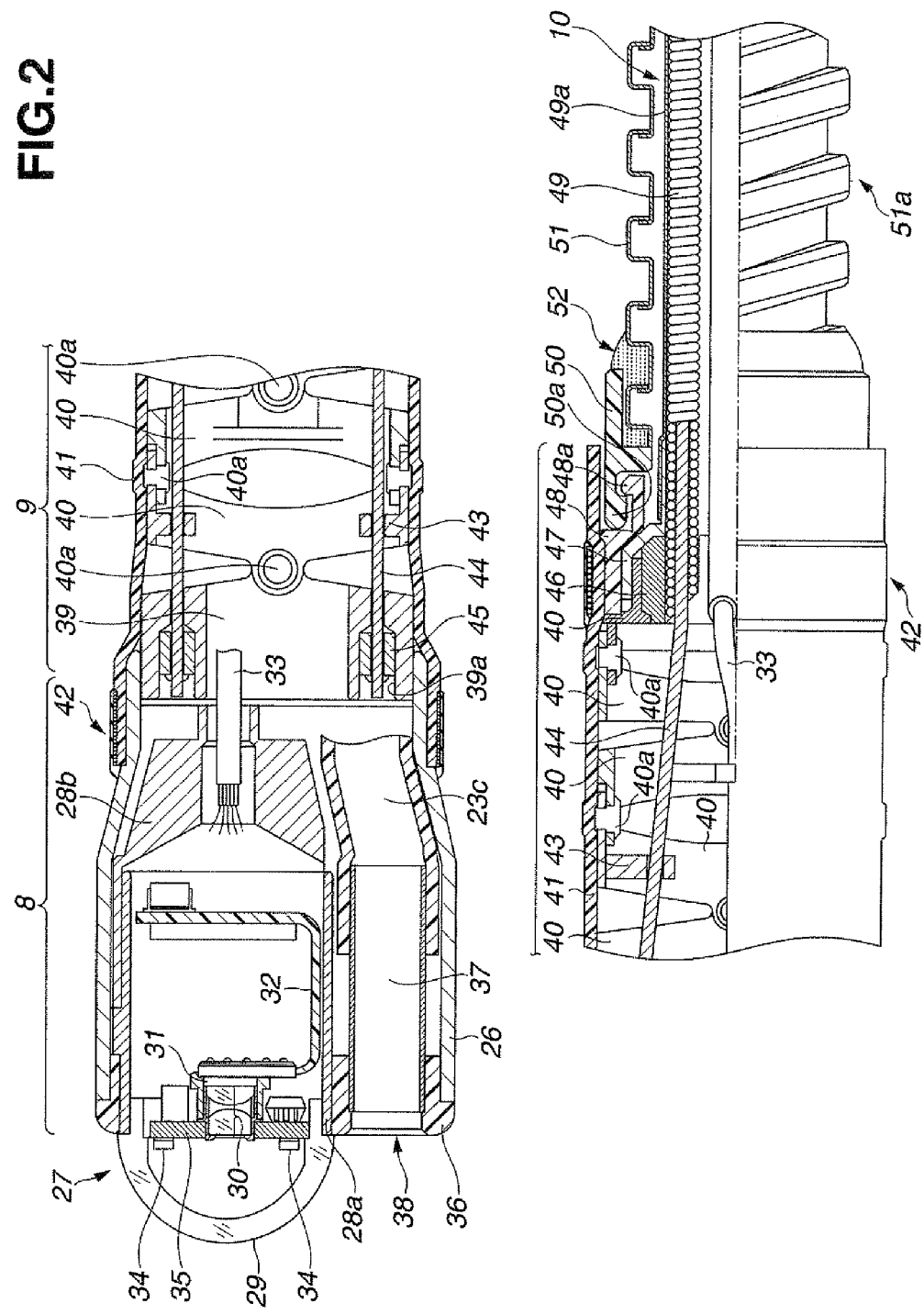
FIG. 2 is a sectional view showing a distal end portion, a bending portion, and a part of a rotating cylinder of the endoscope according to the embodiment.
Figure 3:
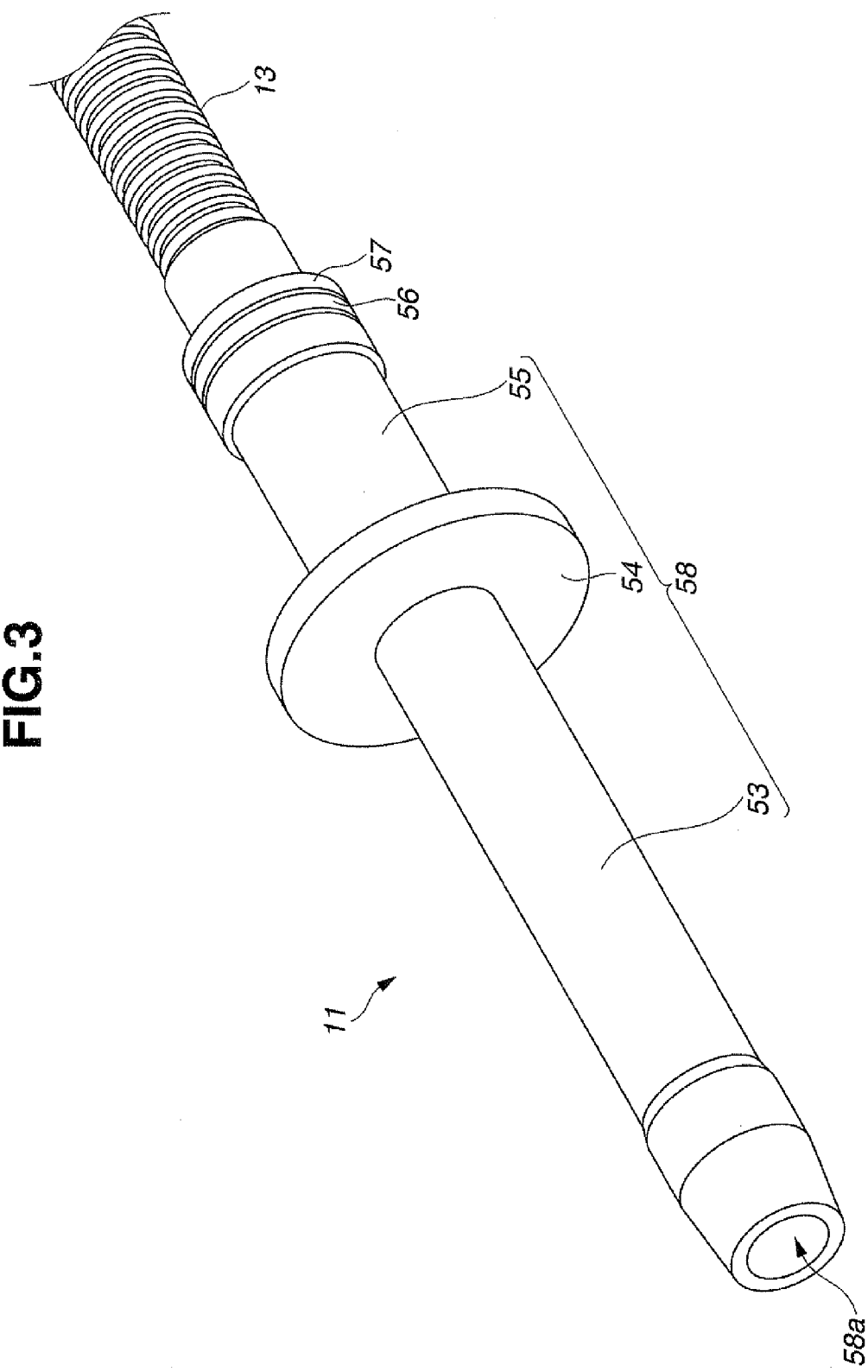
FIG. 3 is a perspective view showing an insertion assisting tool according to the embodiment.
Figure 4:
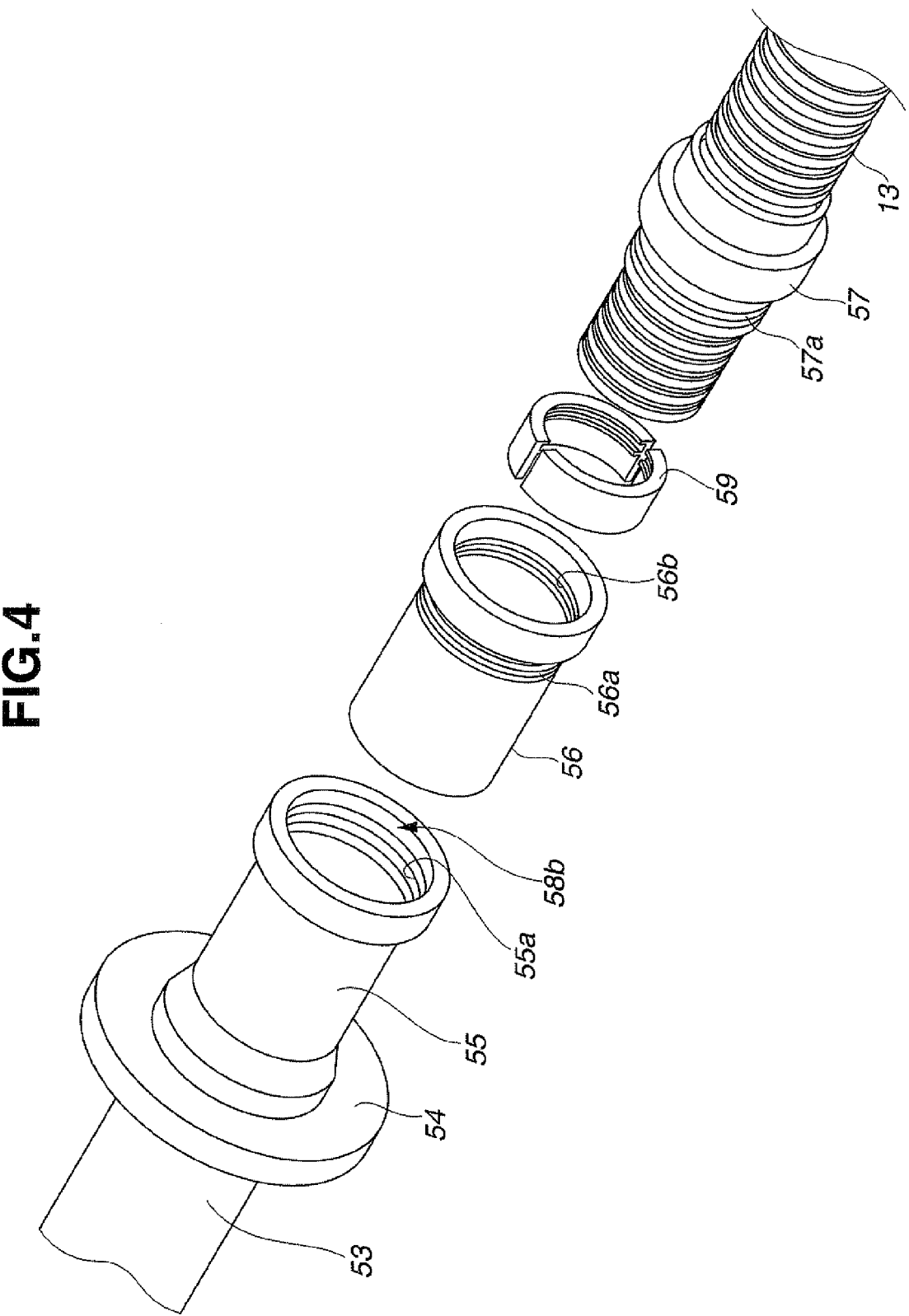
FIG. 4 is a disassembled perspective view of the insertion assisting tool to which a guide tube is connected according to the embodiment.
Figure 5:
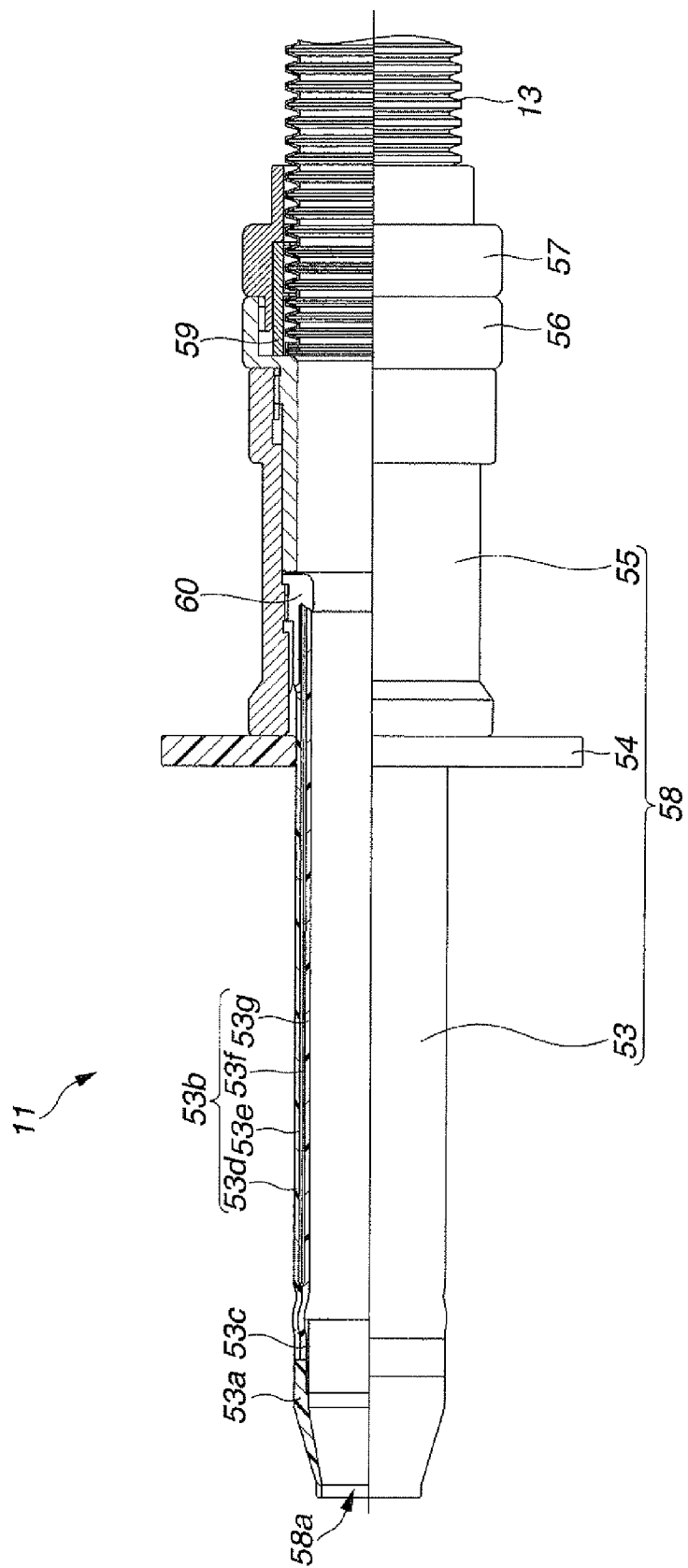
FIG. 5 is a sectional view of the insertion assisting tool with the guide tube connected thereto according to the embodiment.
Figure 6:
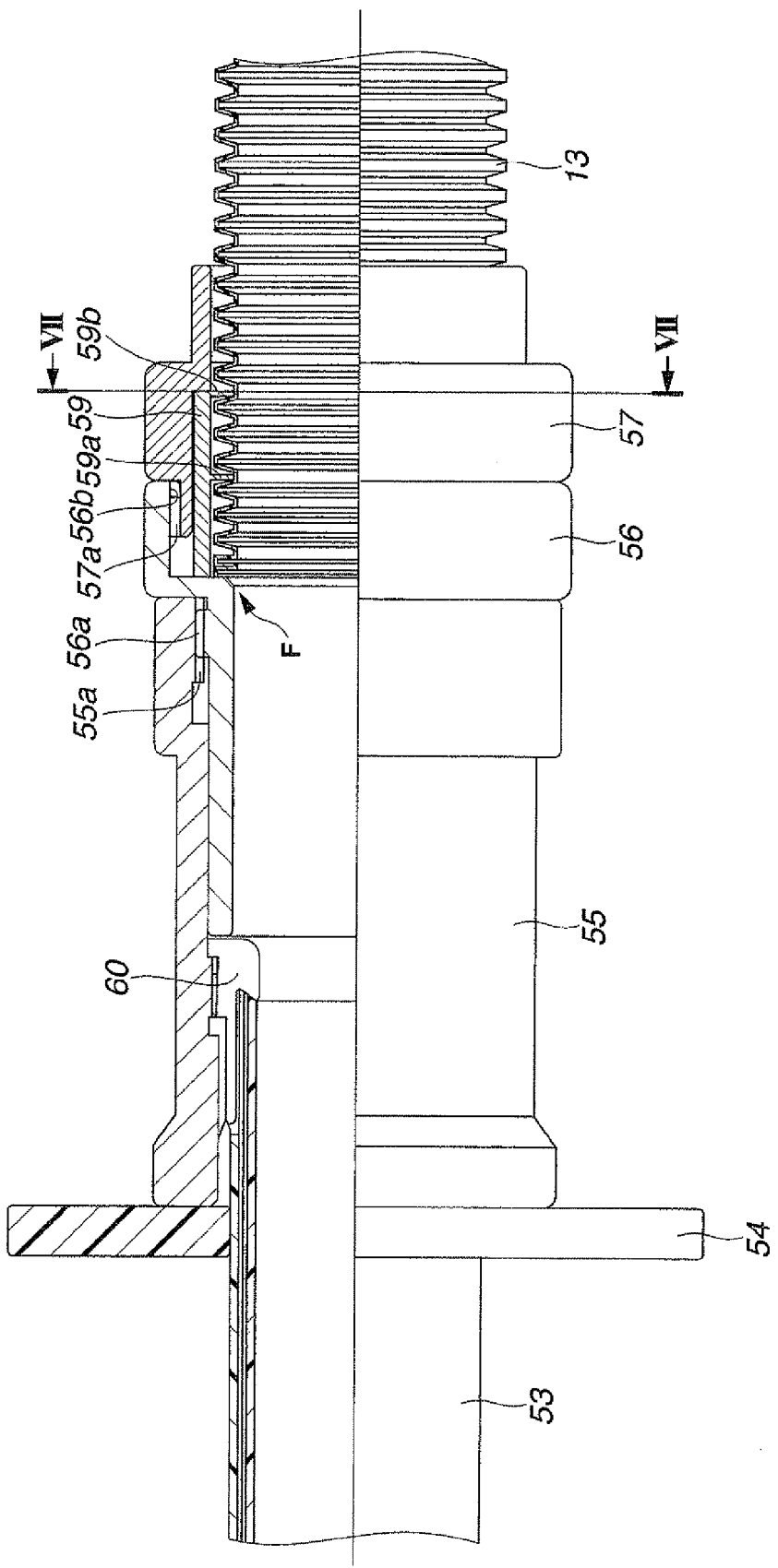
FIG. 6 is a sectional view showing a proximal end portion of the insertion assisting tool with the guide tube connected thereto according to the embodiment.
Figure 7:
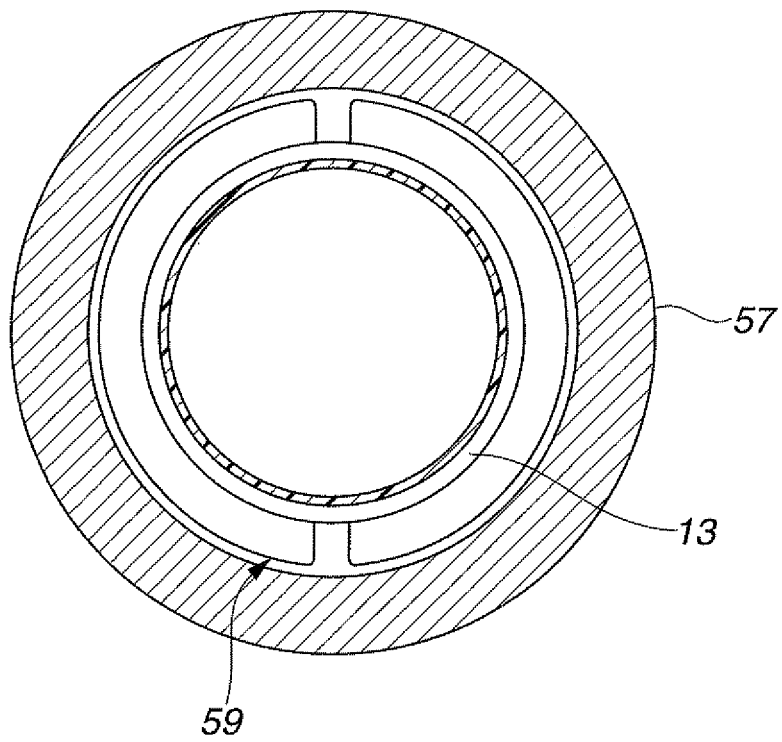
FIG. 7 is a sectional view of the insertion assisting tool along VII-VII line in FIG. 6 according to the embodiment.
Figure 8:
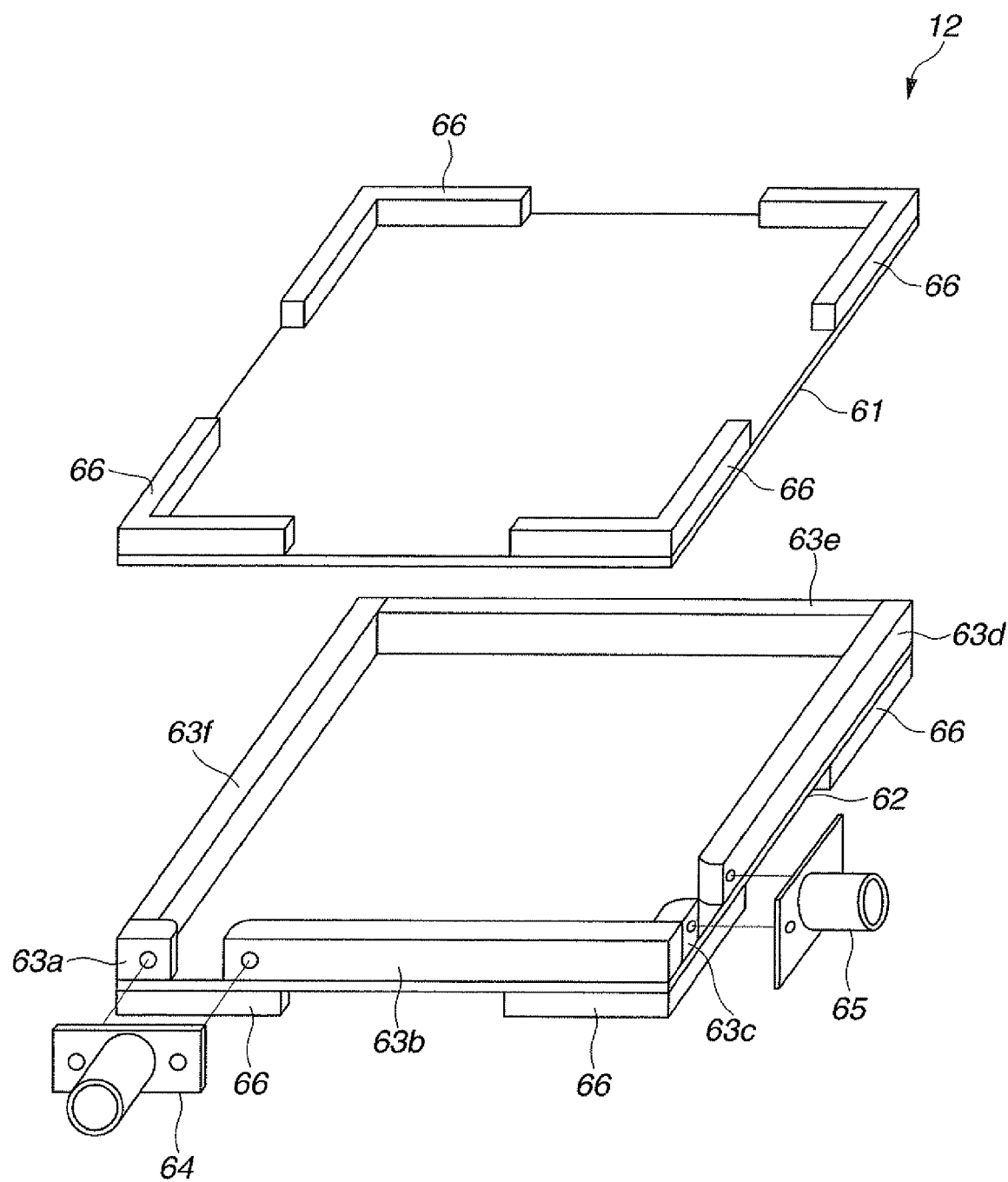
FIG. 8 is a disassembled perspective view of a housing case according to the embodiment.
Figure 9:
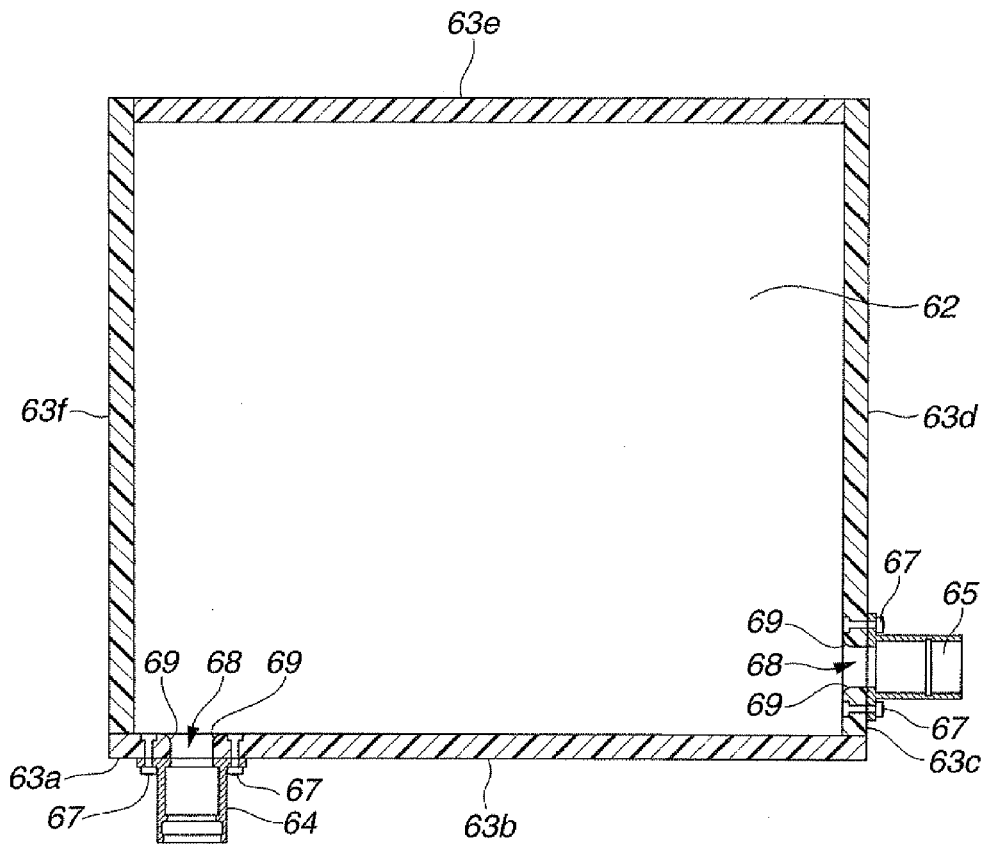
FIG. 9 is a sectional view of the housing case according to the embodiment.
Figure 10:
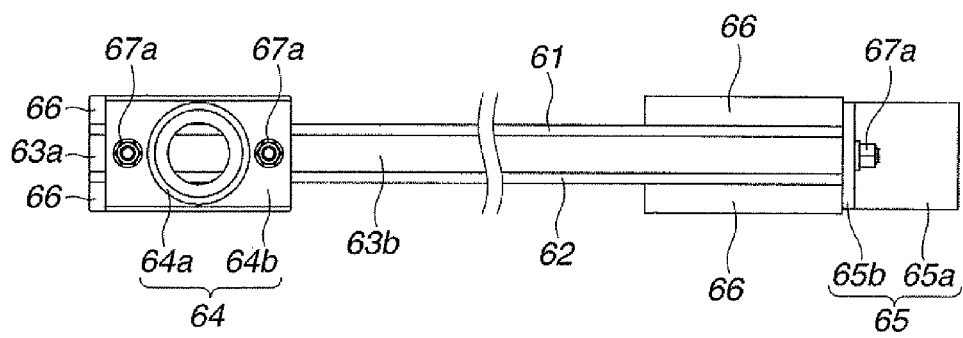
FIG. 10 is a plan view of the housing case viewed from one side according to the embodiment.
Figure 11:
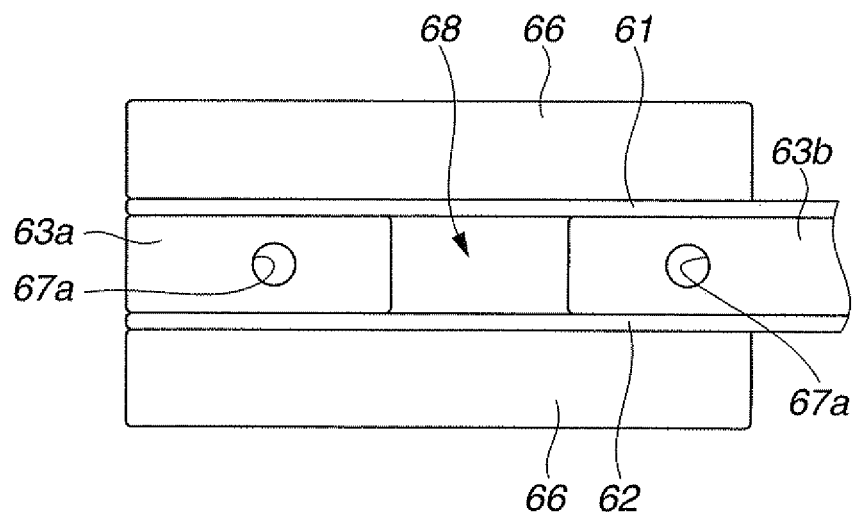
FIG. 11 is an enlarged view showing one side of the housing case to which a guide tube fixing member is attached according to the embodiment.
Figure 12:
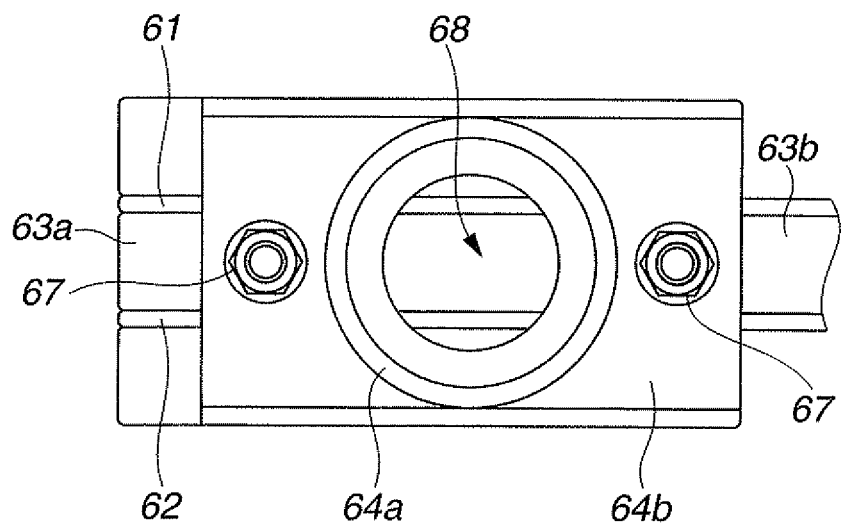
FIG. 12 is an enlarged plan view showing a state in which the guide tube fixing member is attached to one side of the housing case shown in FIG. 11 according to the embodiment.
Figure 13:
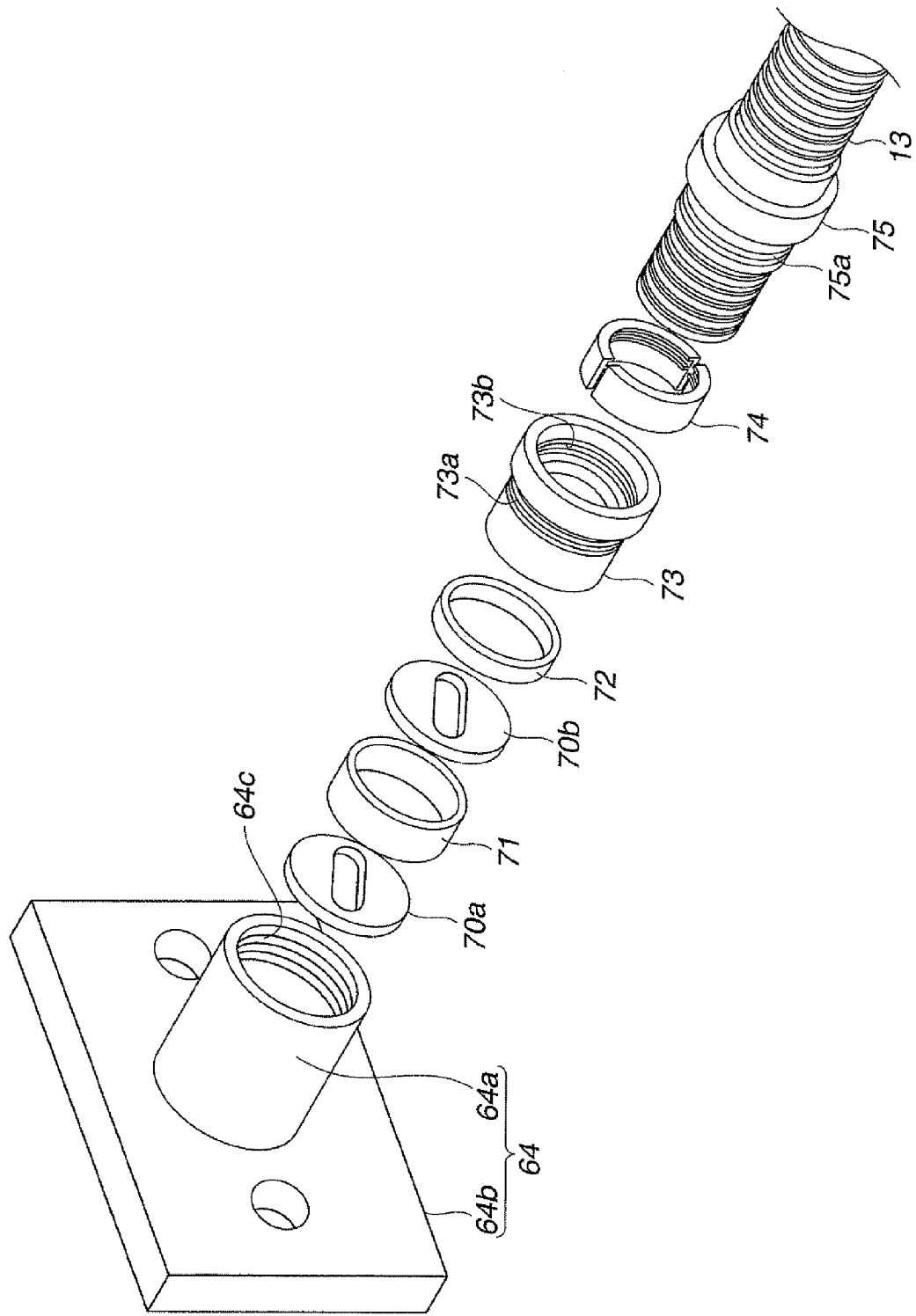
FIG. 13 is a disassembled perspective view of the guide tube fixing member, in which a thrust generating member is disposed, according to the embodiment.
Figure 14:
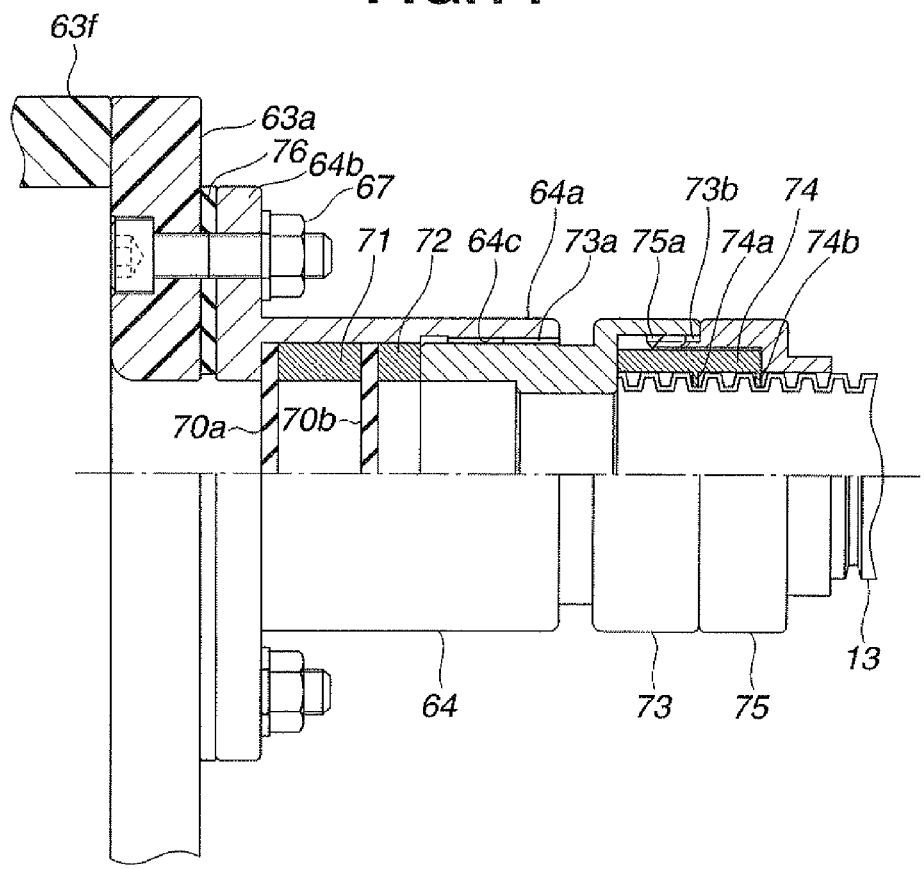
FIG. 14 is a partial sectional view of the guide tube fixing member, in which the thrust generating member is disposed, viewed from an up to down direction of the housing case according to the embodiment.
Figure 15:
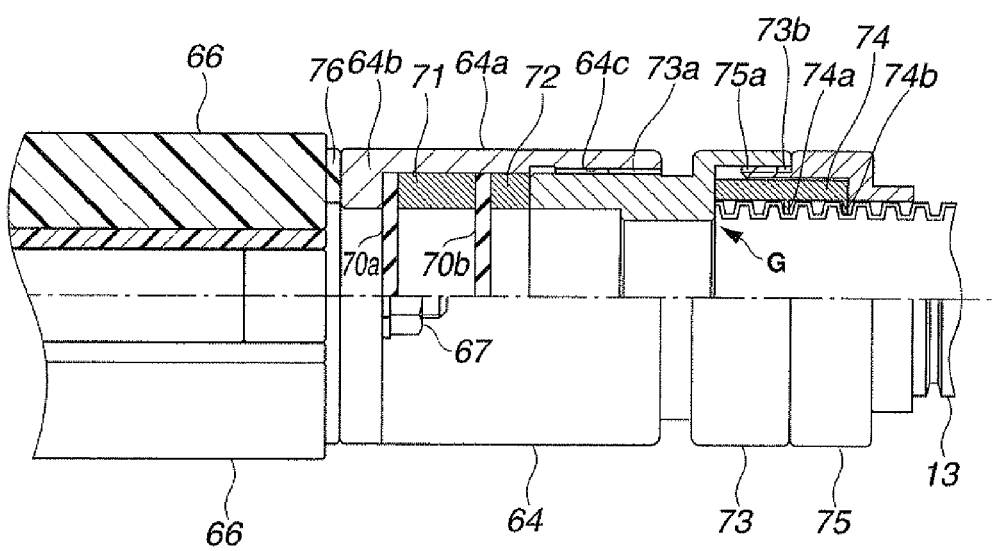
FIG. 15 is a partial sectional view of the guide tube fixing member, in which the thrust generating member is disposed, viewed from a left to right direction of the housing case according to the embodiment.
Figure 16:
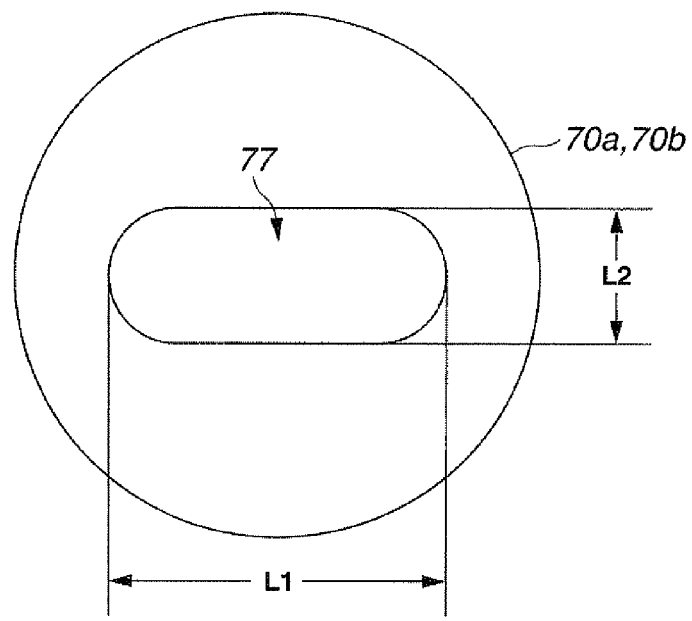
FIG. 16 is a plan view showing the thrust generating member according to the embodiment.
Figure 17:
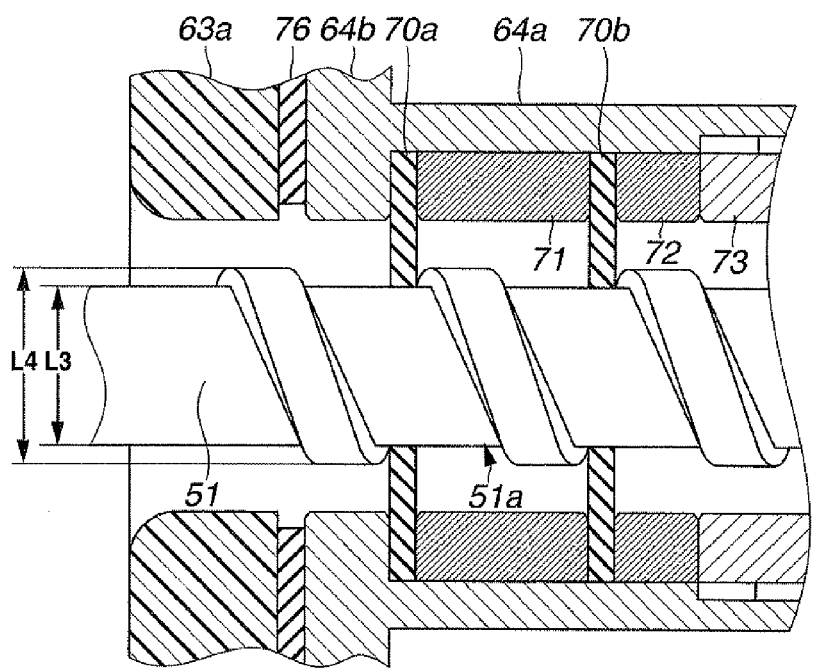
FIG. 17 is a sectional view for explaining an action of the thrust generating member in the guide tube fixing member, through which the rotating cylinder is inserted, according to the embodiment.
Figure 18:
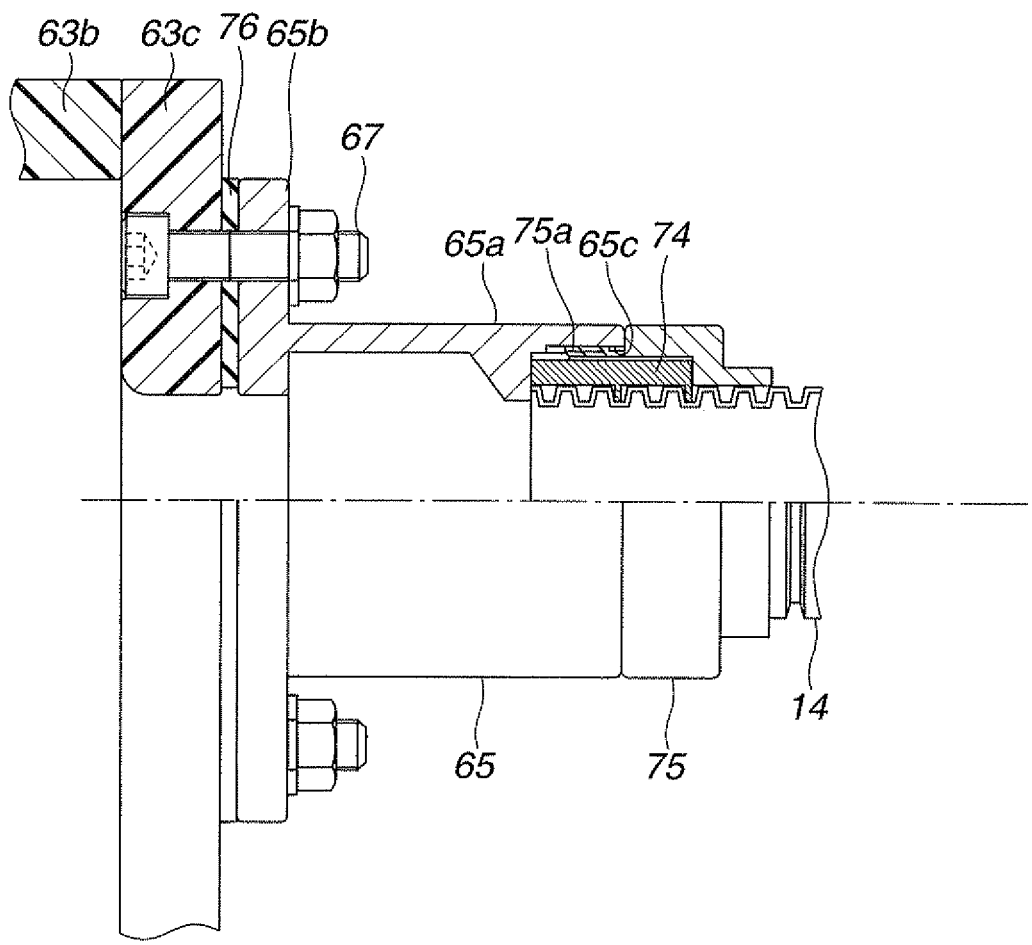
FIG. 18 is a partial sectional view of the guide tube fixing member on the operation portion side according to the embodiment.
Figure 19:
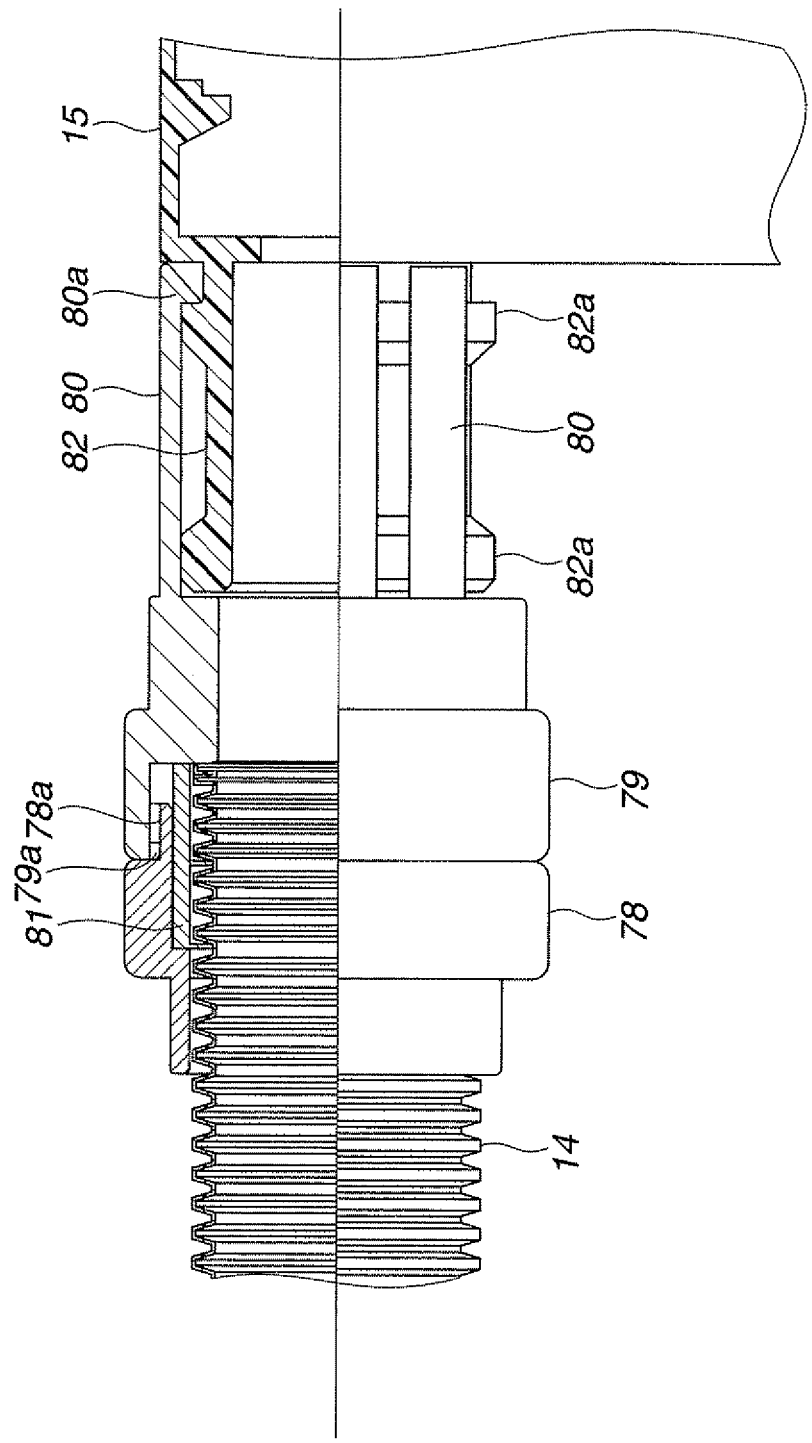
FIG. 19 is a sectional view showing a state of connection between an operation portion side guide tube and a connector cover according to the embodiment.
Figure 20:
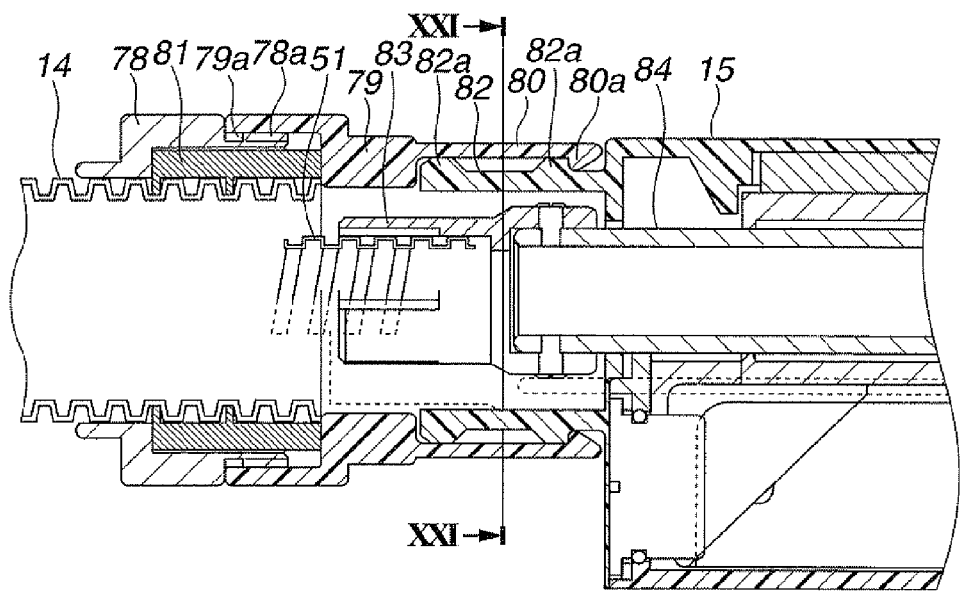
FIG. 20 is a sectional view showing a part of the connector cover, to which the operation portion side guide tube is connected, according to the embodiment.
Figure 21:
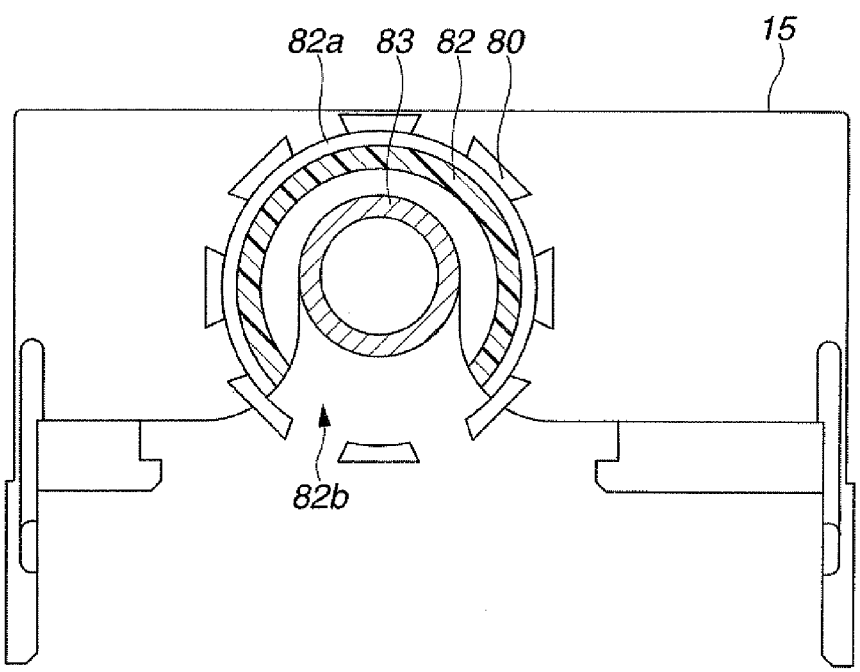
FIG. 21 is a plan view of a connector box showing a section along XXI-XXI line in FIG. 20 according to the embodiment.
Figure 22:
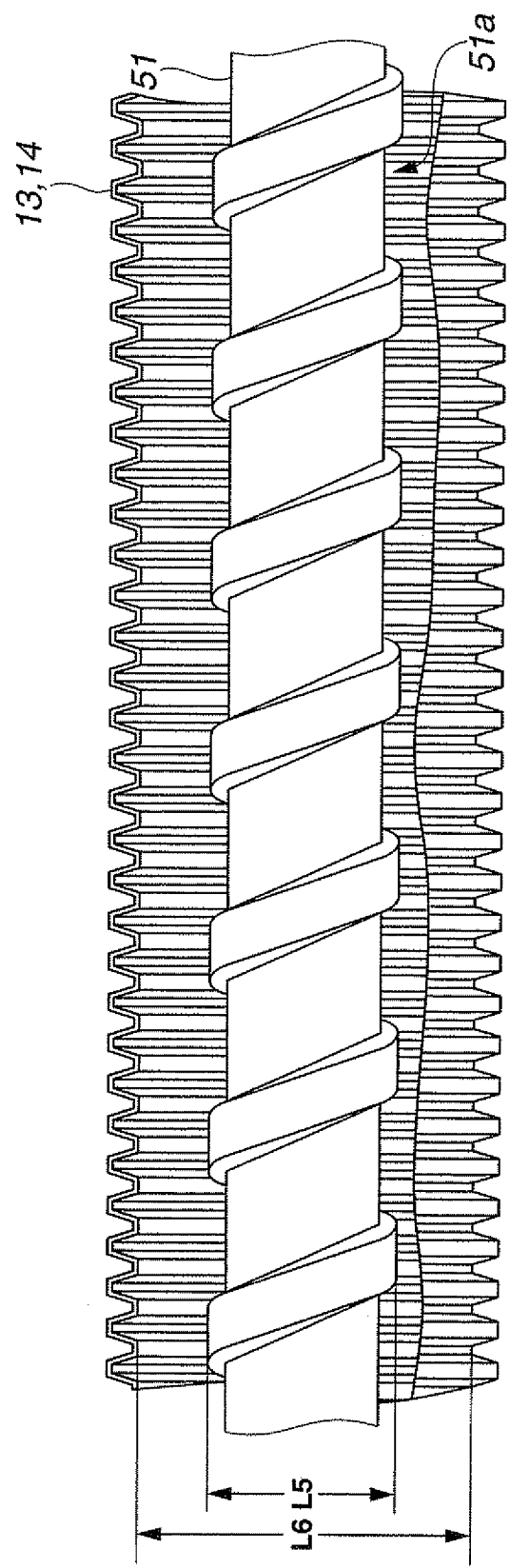
FIG. 22 is a sectional view showing a state in which the rotating cylinder of an insertion portion main body is inserted through the guide tube according to the embodiment.
Figure 23:
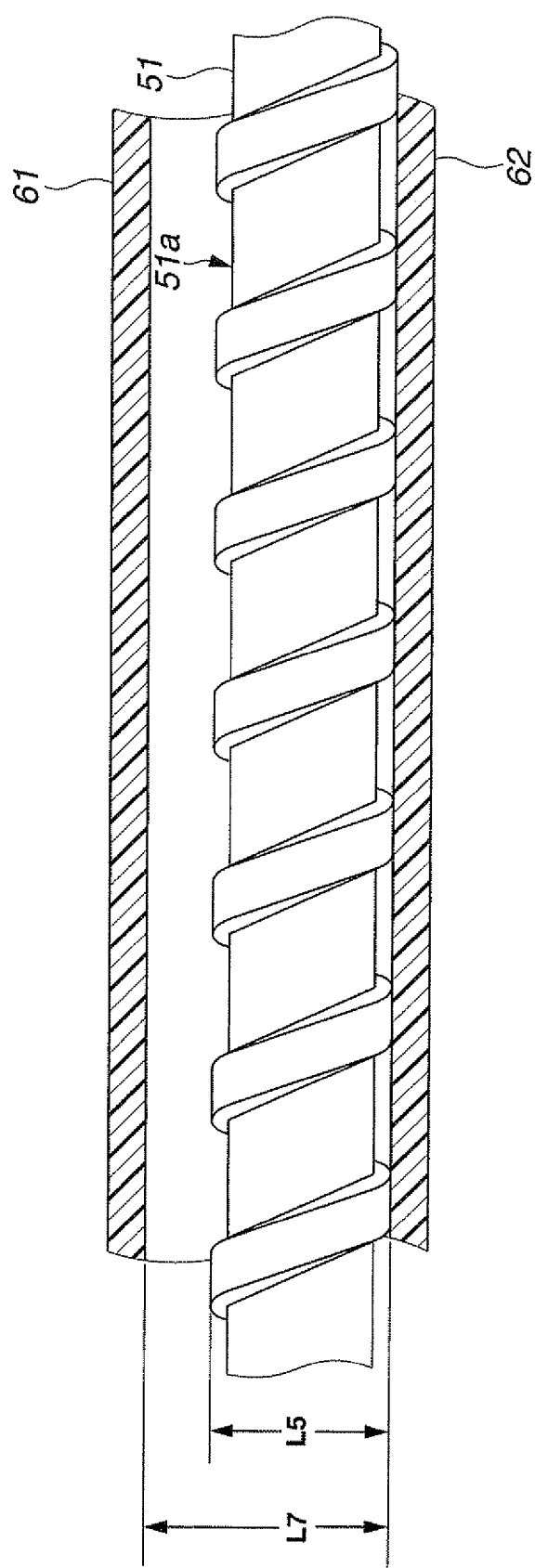
FIG. 23 is a sectional view of the rotating cylinder of the insertion portion main body in the housing case viewed from one side according to the embodiment.
Figure 24:
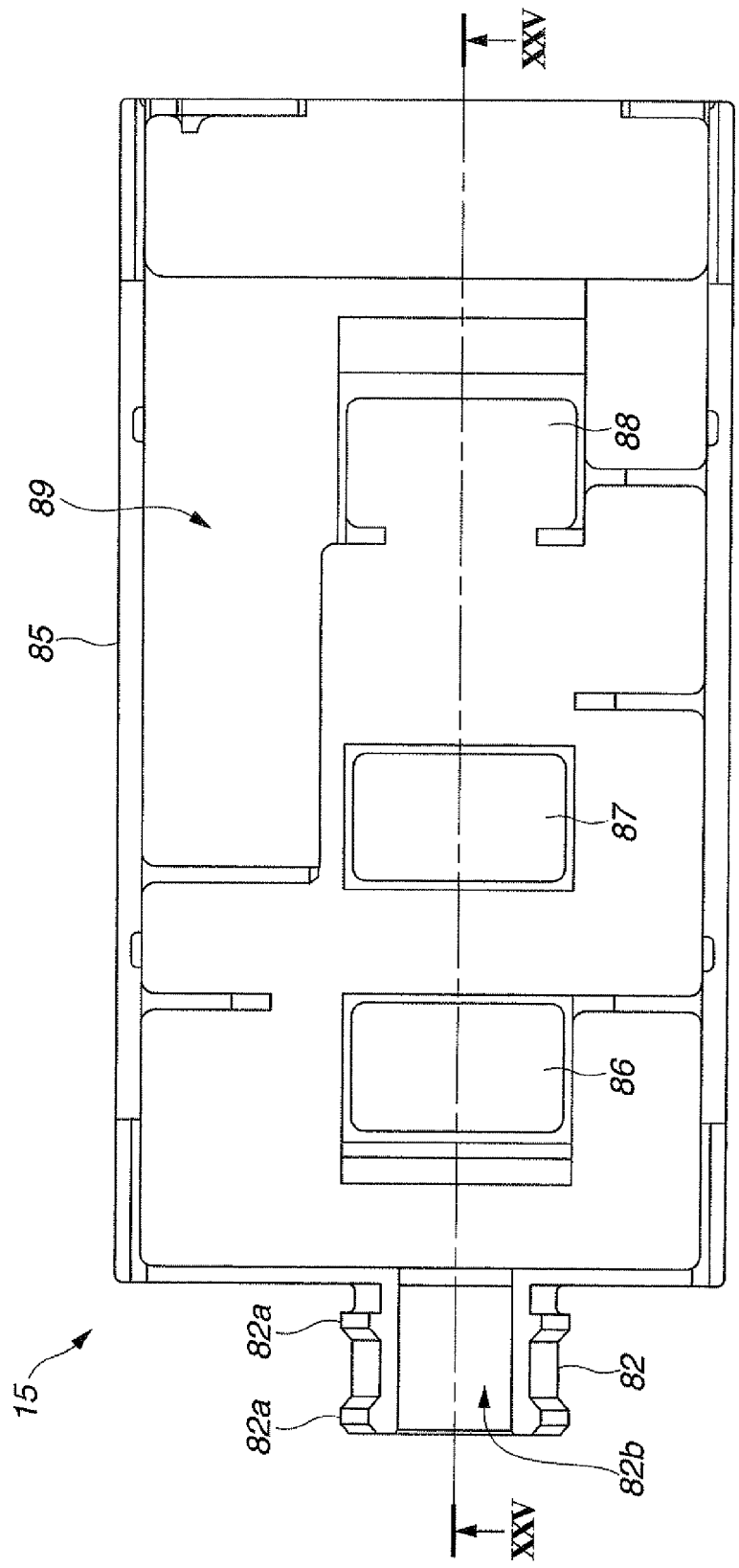
FIG. 24 is a plan view of the connector cover viewed from a surface on an opening side according to the embodiment.
Figure 25:
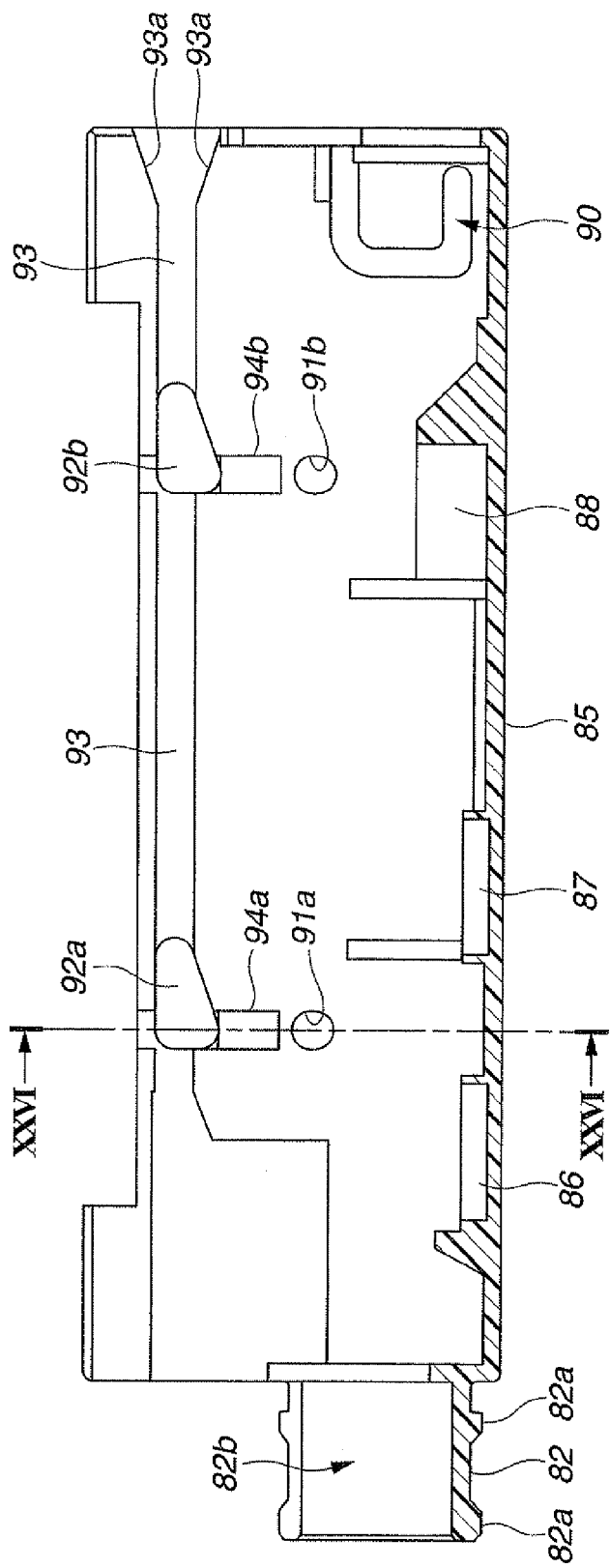
FIG. 25 is a sectional view of the connector cover along XXV-XXV line in FIG. 24 according to the embodiment.
Figure 26:
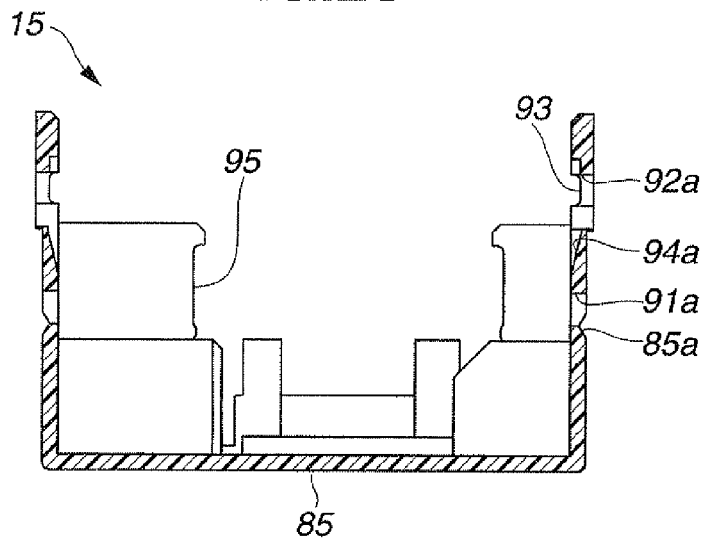
FIG. 26 is a sectional view of the connector cover along XXVI-XXVI line in FIG. 25 according to the embodiment.
Figure 27:
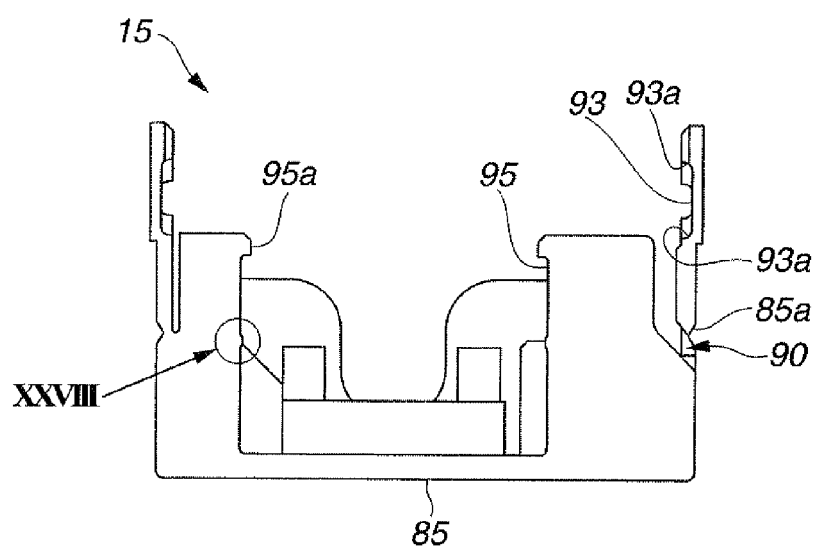
FIG. 27 is a plan view of a connector main body of the connector cover viewed from a proximal end side according to the embodiment.
Figure 28:
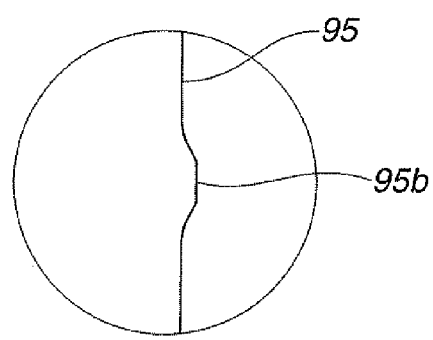
FIG. 28 is a diagram for explaining a locking convex portion in an enlarged circle XXVIII in FIG. 27 according to the embodiment.
Figure 29:
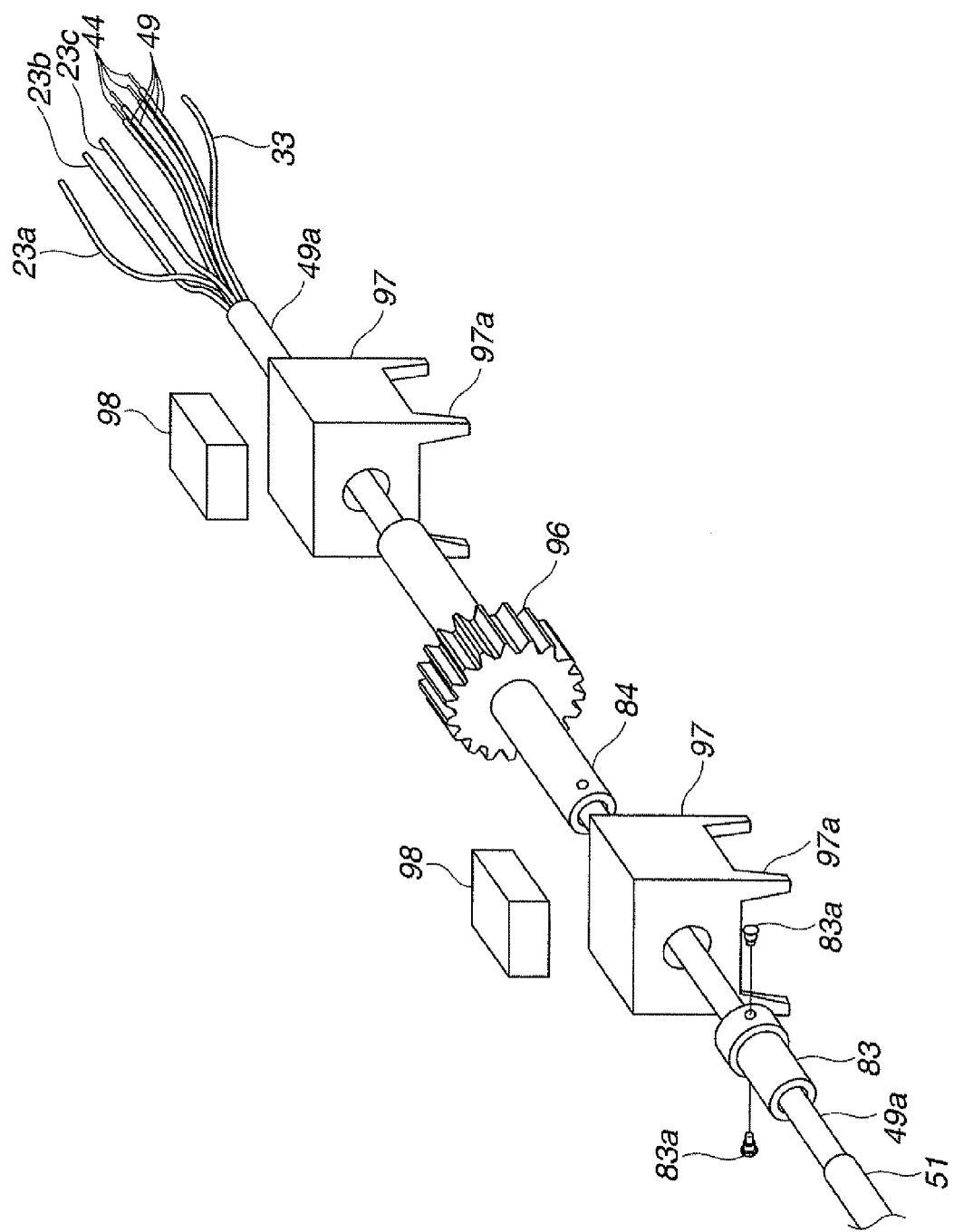
FIG. 29 is a disassembled perspective view for explaining an insertion portion side gear, a rotating shaft, a bearing, and an elastic member disposed in the connector main body.
Figure 30:
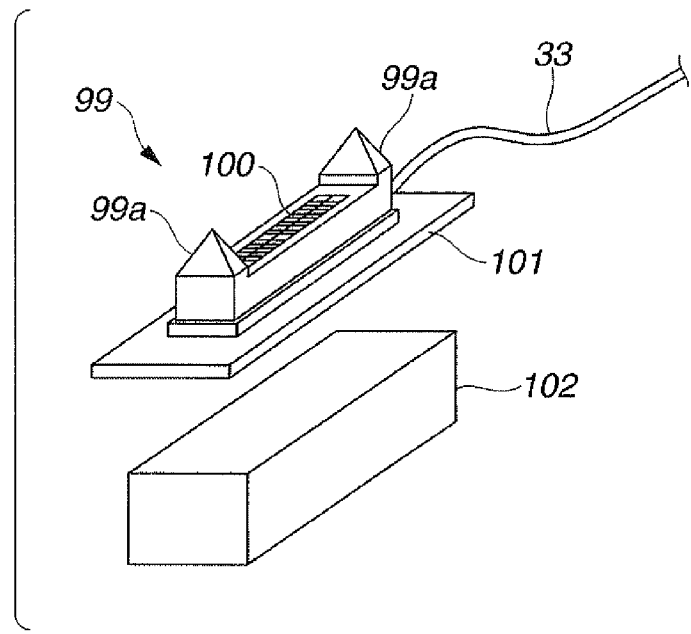
FIG. 30 is a diagram for explaining an electric connector and the elastic member according to the embodiment.
Figure 31:
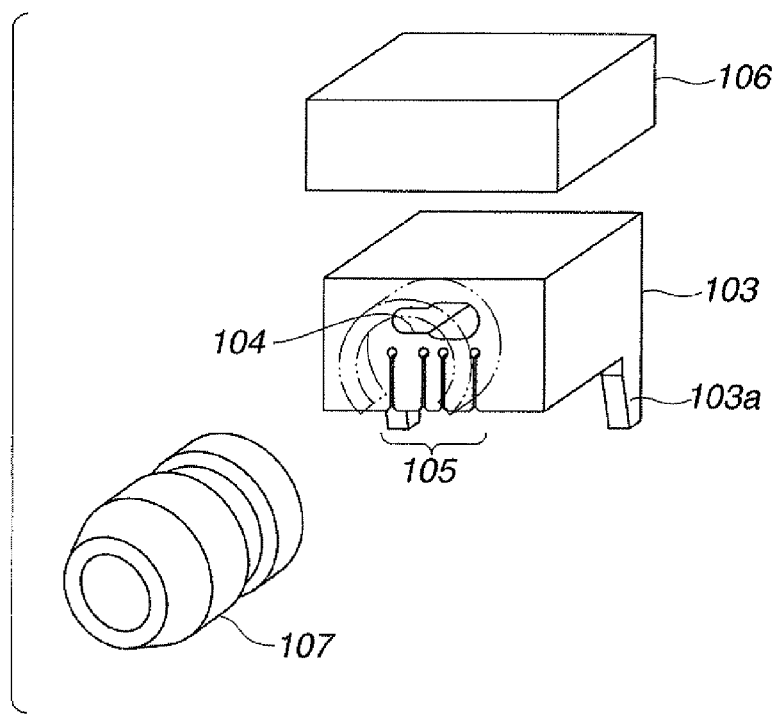
FIG. 31 is a diagram for explaining a content holding body and the elastic member according to the embodiment.
Figure 32:
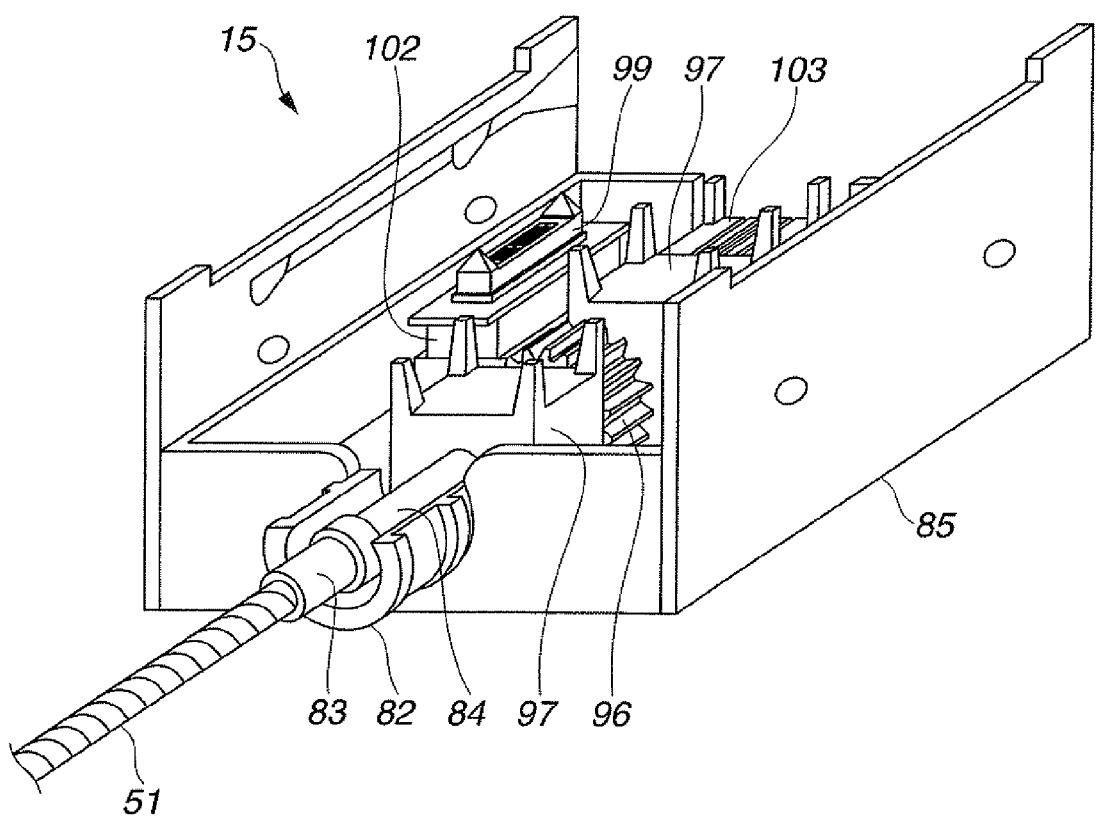
FIG. 32 is a perspective view of an assembled connector main body with a rear side thereof set upward according to the embodiment.
Figure 33:
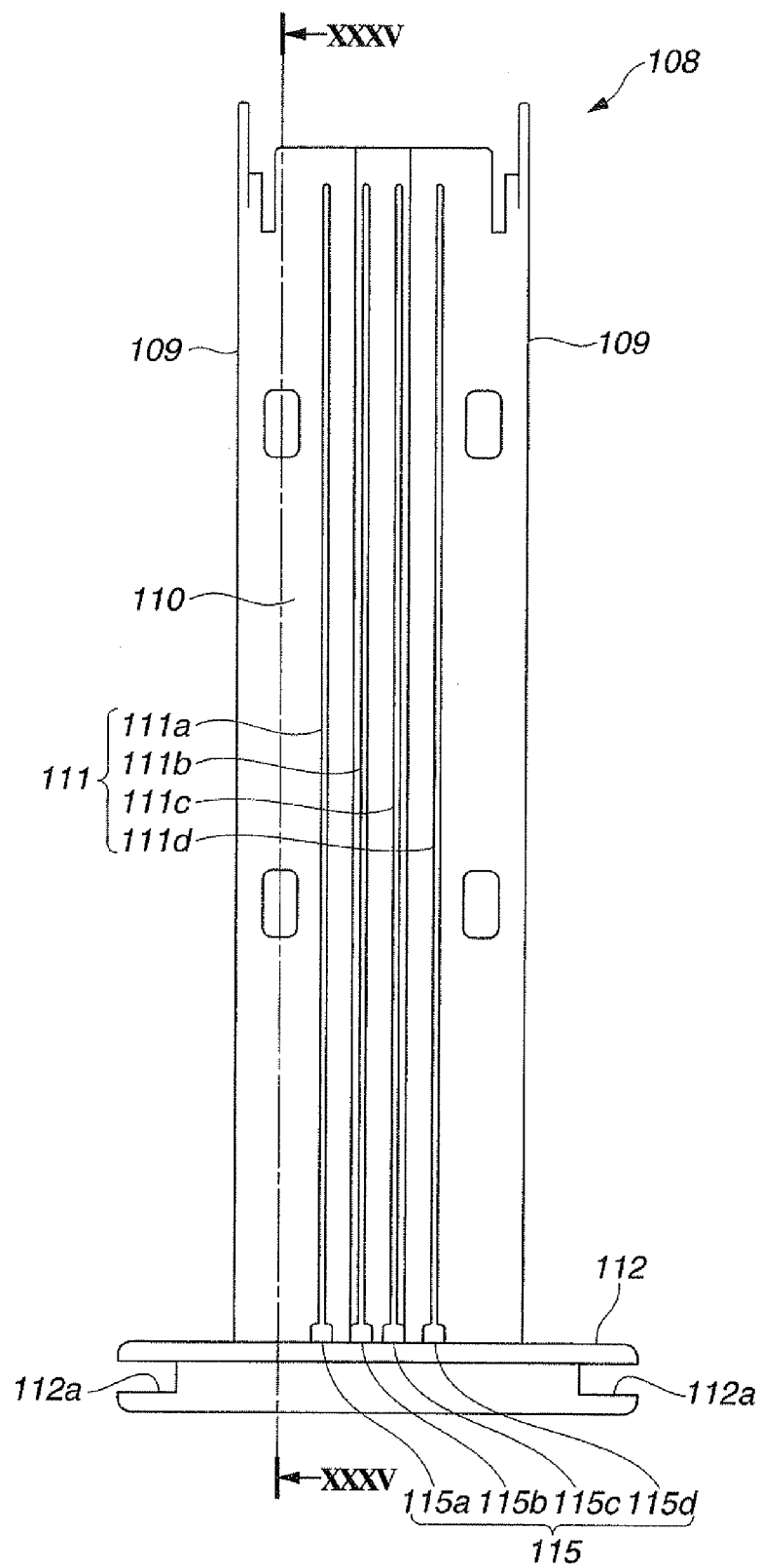
FIG. 33 is a plan view showing an upper surface of a wire connection plate according to the embodiment.
Figure 34:
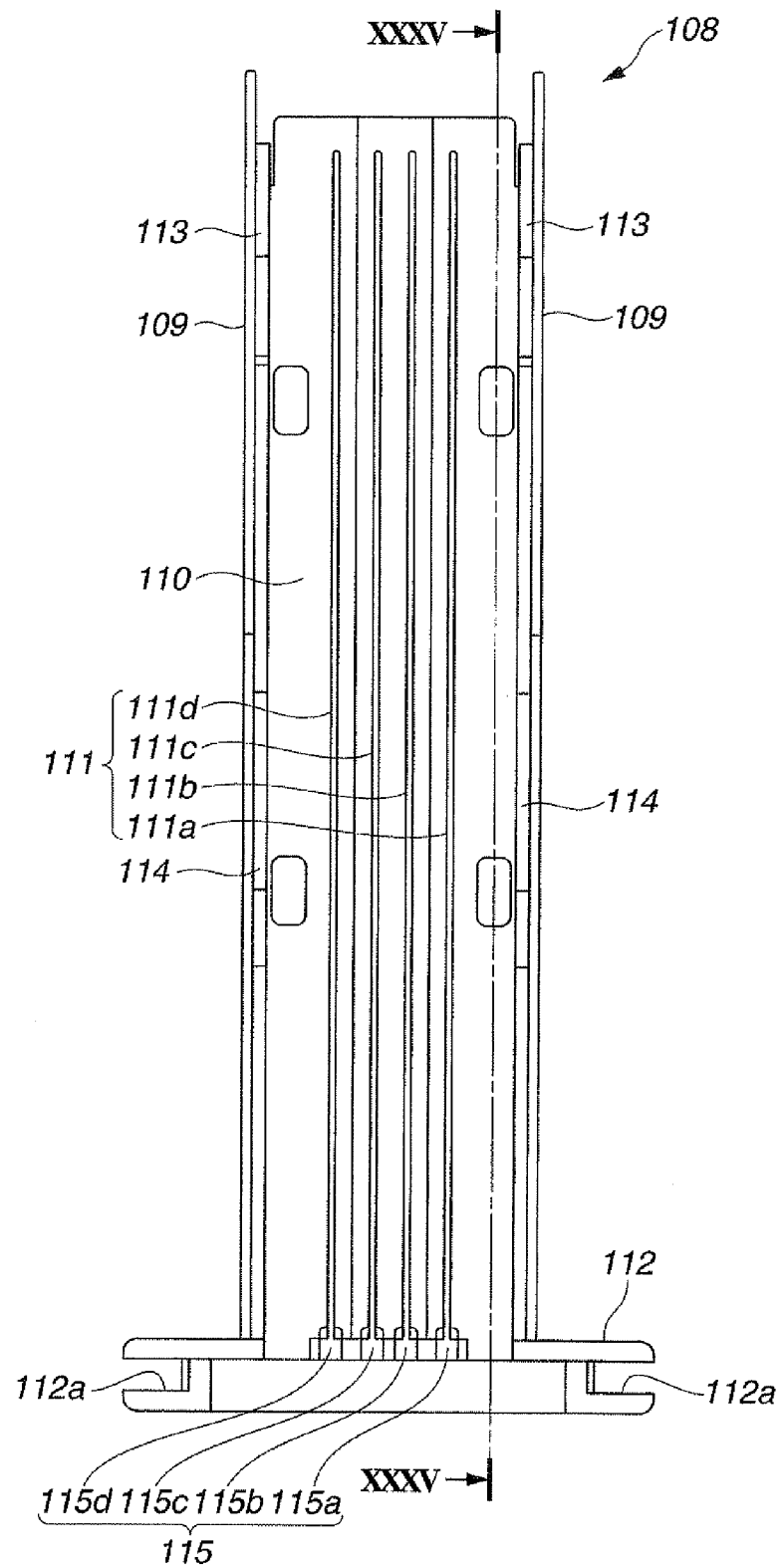
FIG. 34 is a plan view showing a rear surface of the wire connection plate according to the embodiment.
Figure 35:
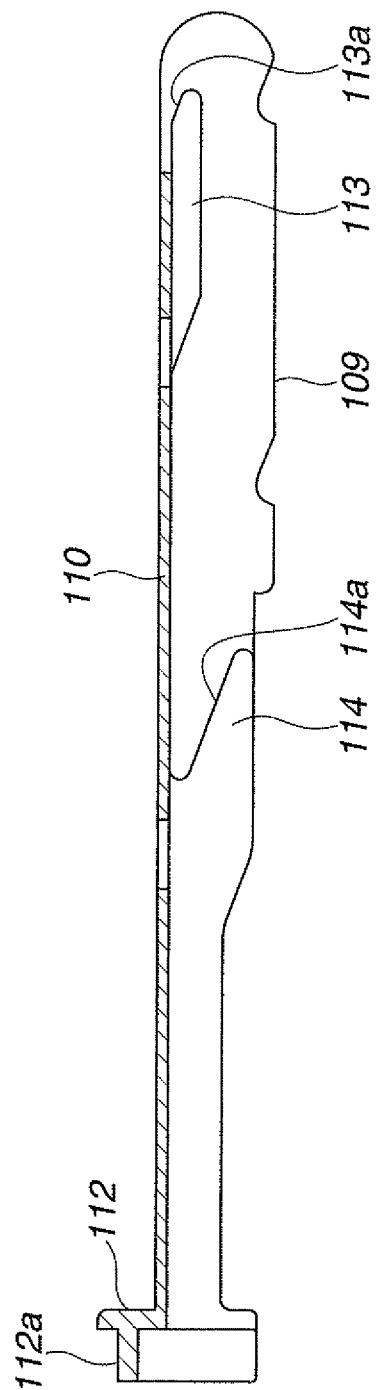
FIG. 35 is a sectional view of the wire connection plate along XXXV-XXXV line in FIGS. 33 and 34 according to the embodiment.
Figure 36:
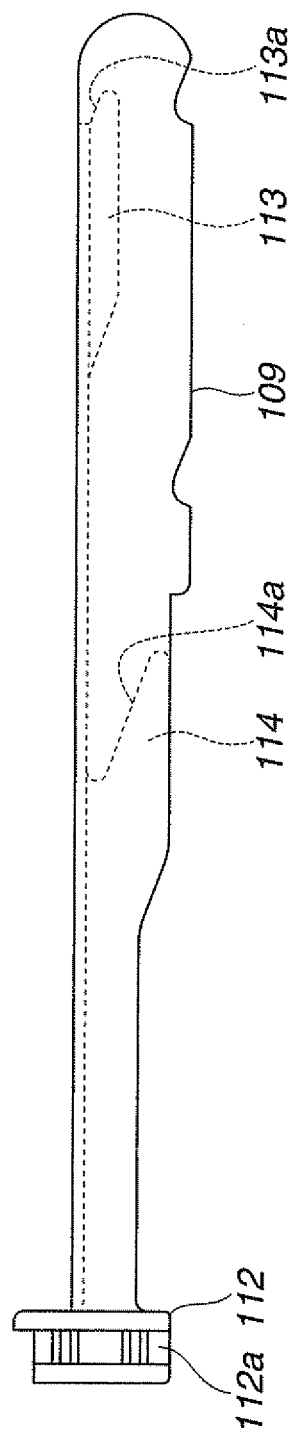
FIG. 36 is a side view of the wire connection plate according to the embodiment.
Figure 37:
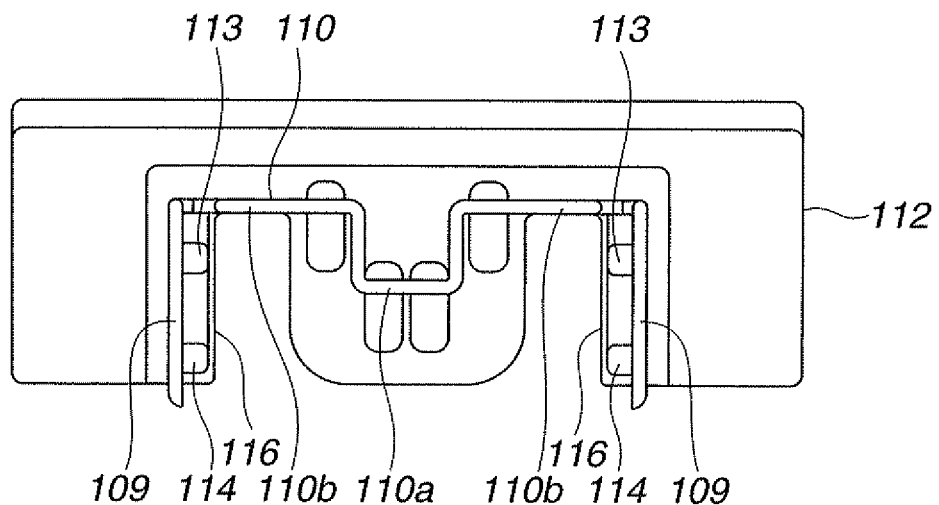
FIG. 37 is a plan view of the wire connection plate viewed from a proximal end side thereof according to the embodiment.
Figure 38:
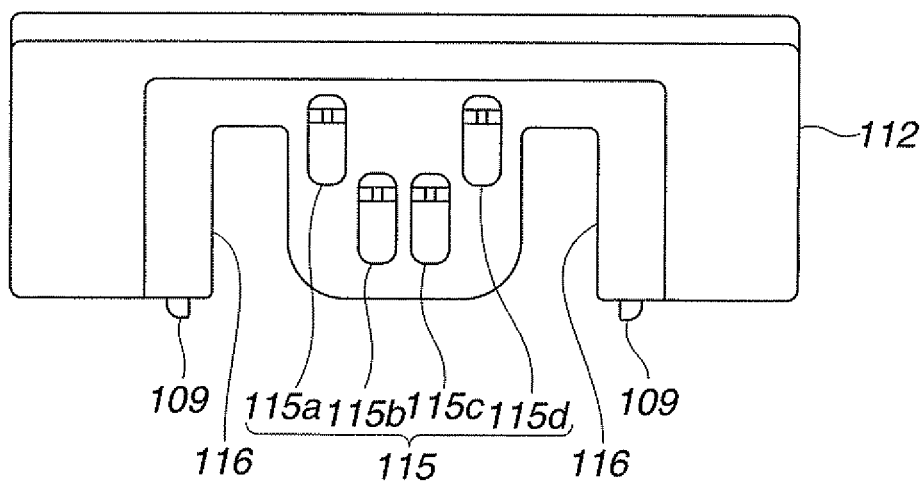
FIG. 38 is a plan view of the wire connection plate viewed from a distal end side thereof according to the embodiment.
Figure 39:
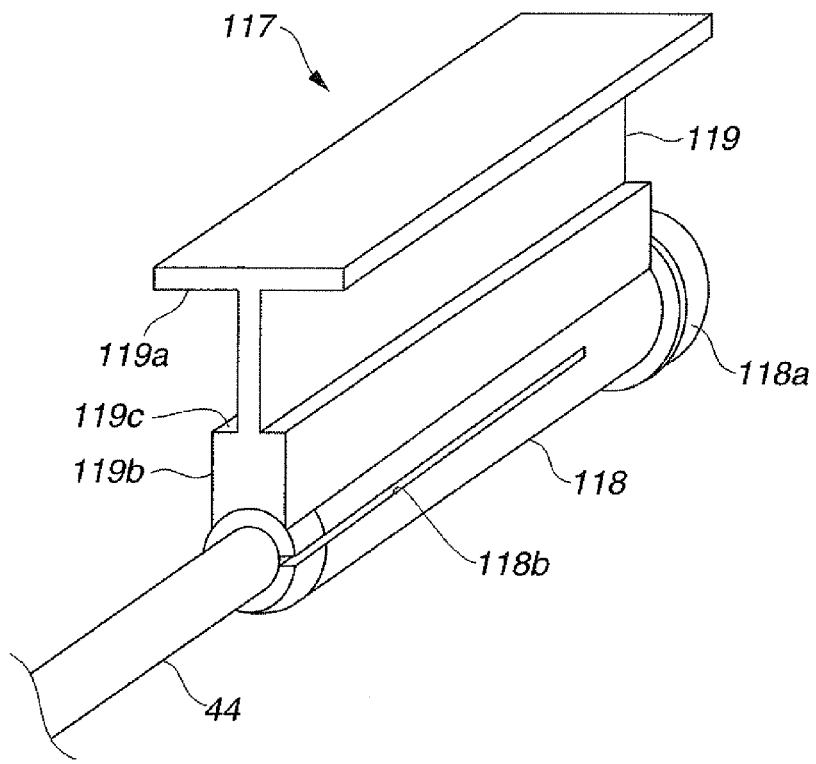
FIG. 39 is a perspective view of a wire anchor connected to a bending operation wire according to the embodiment.
Figure 40:
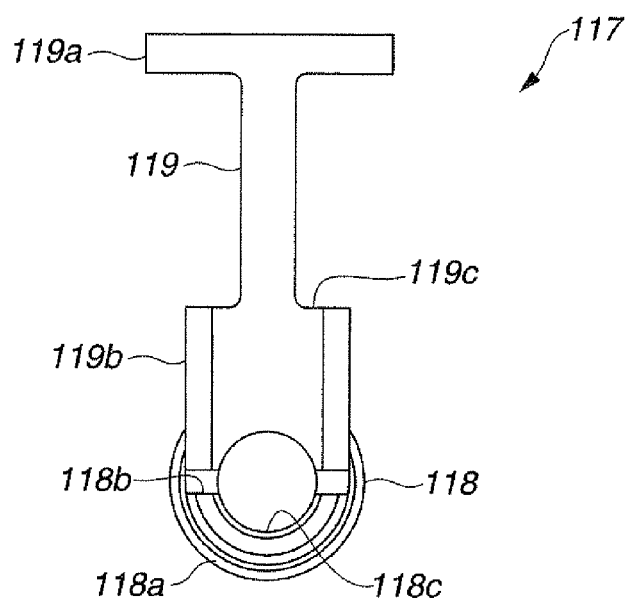
FIG. 40 is a plan view of the wire anchor viewed from a distal end side thereof according to the embodiment.
Figure 41:
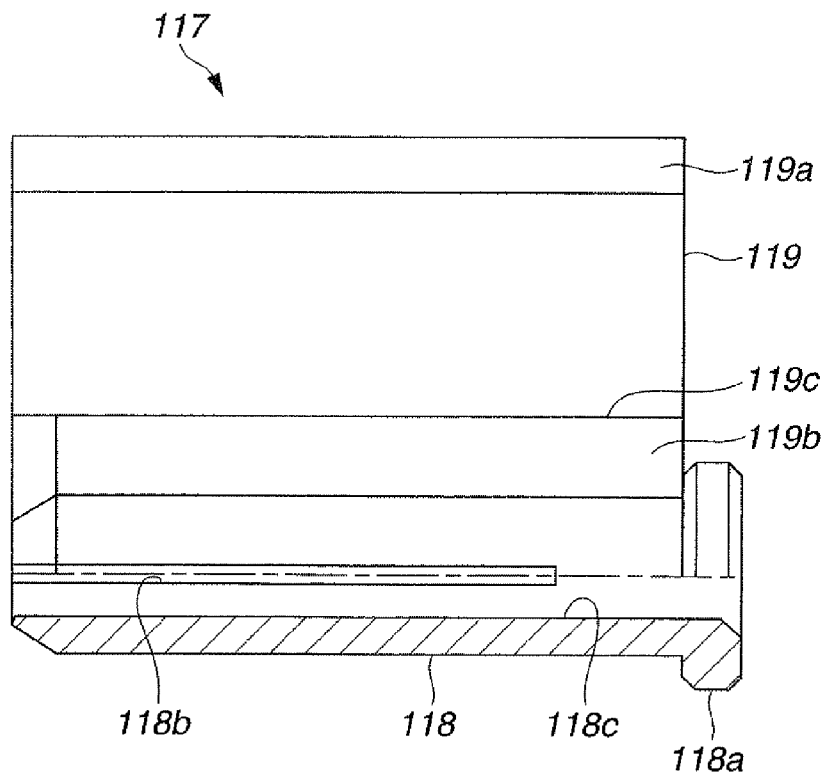
FIG. 41 is a partial sectional view showing a side of the wire anchor according to the embodiment.
Figure 42:
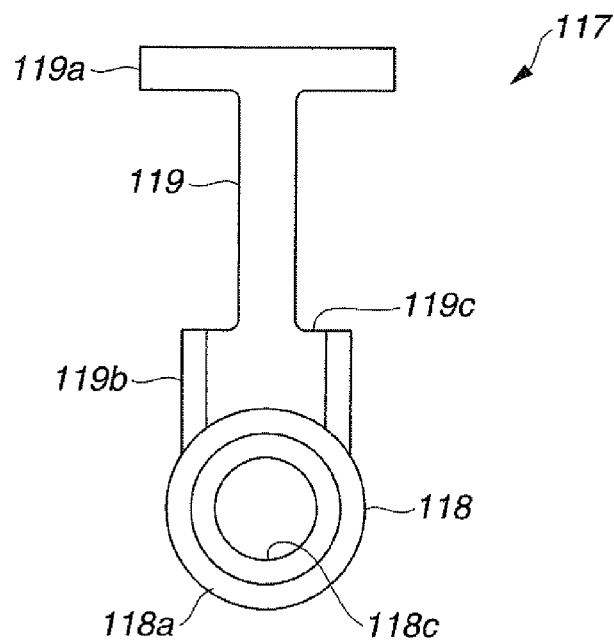
FIG. 42 is a plan view of the wire anchor viewed from a proximal end side thereof according to the embodiment.
Figure 43:
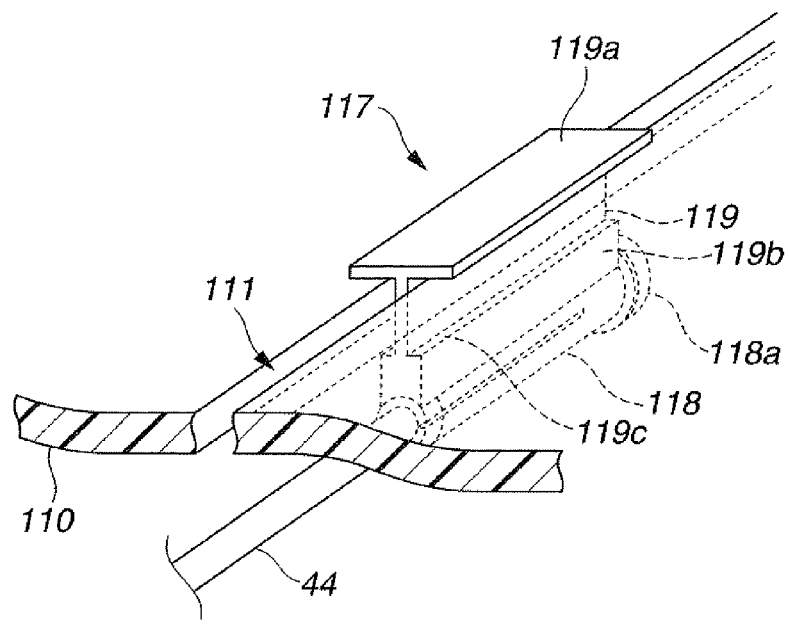
FIG. 43 is a diagram for explaining a state in which the wire anchor is disposed on the wire connection plate according to the embodiment.
Figure 44:
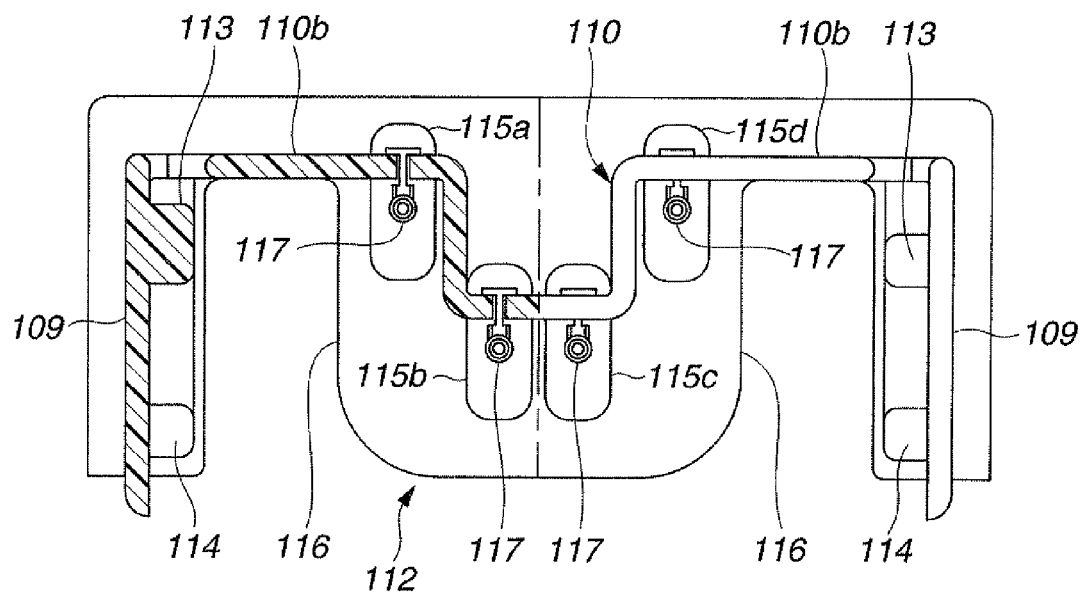
FIG. 44 is a plan view of the wire connection plate having the wire anchor disposed thereon viewed from a proximal end direction of the wire connection plate according to the embodiment.
Figure 45:
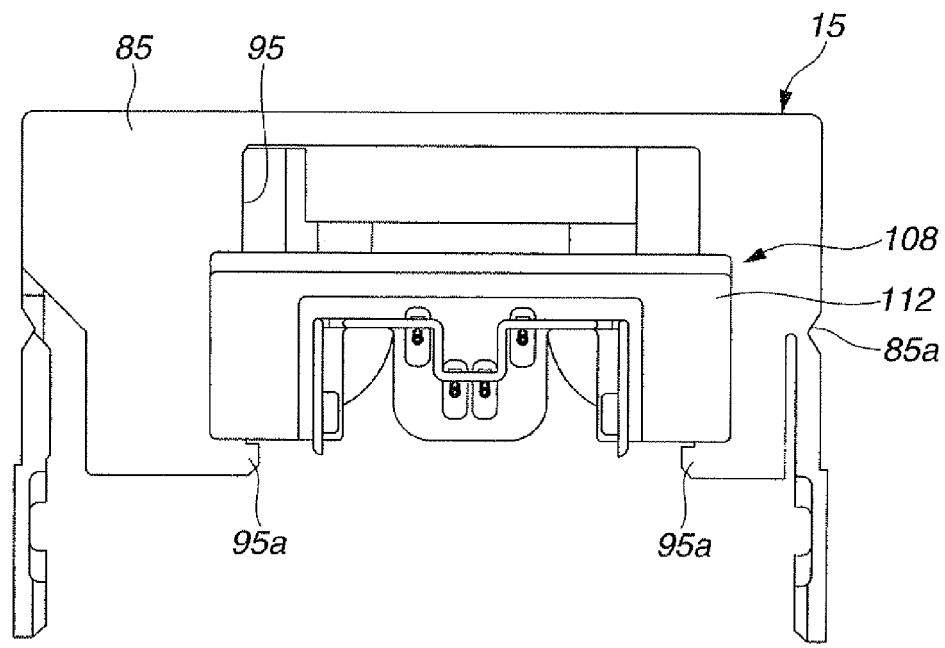
FIG. 45 is a diagram showing a state in which the wire connection plate is attached to the connector main body according to the embodiment.
Figure 46:
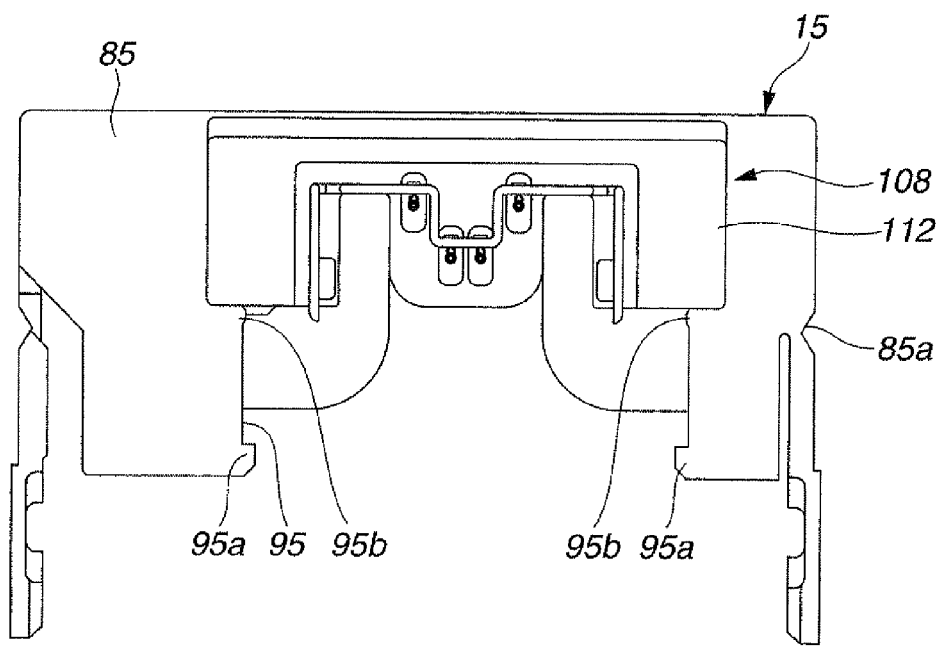
FIG. 46 is a diagram for explaining a state in which the wire connection plate is moved with respect to the connector main body according to the embodiment.
Figure 47:
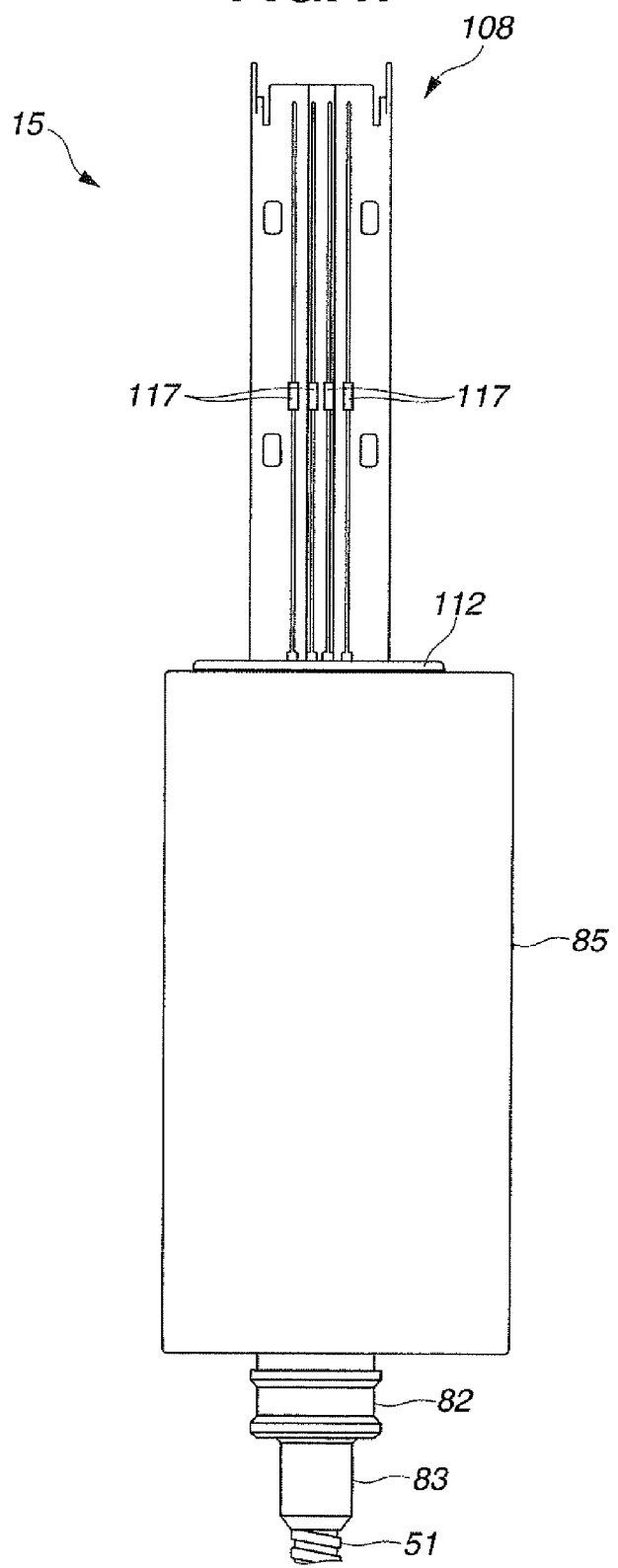
FIG. 47 is a top view of the connector cover according to the embodiment.
Figure 48:
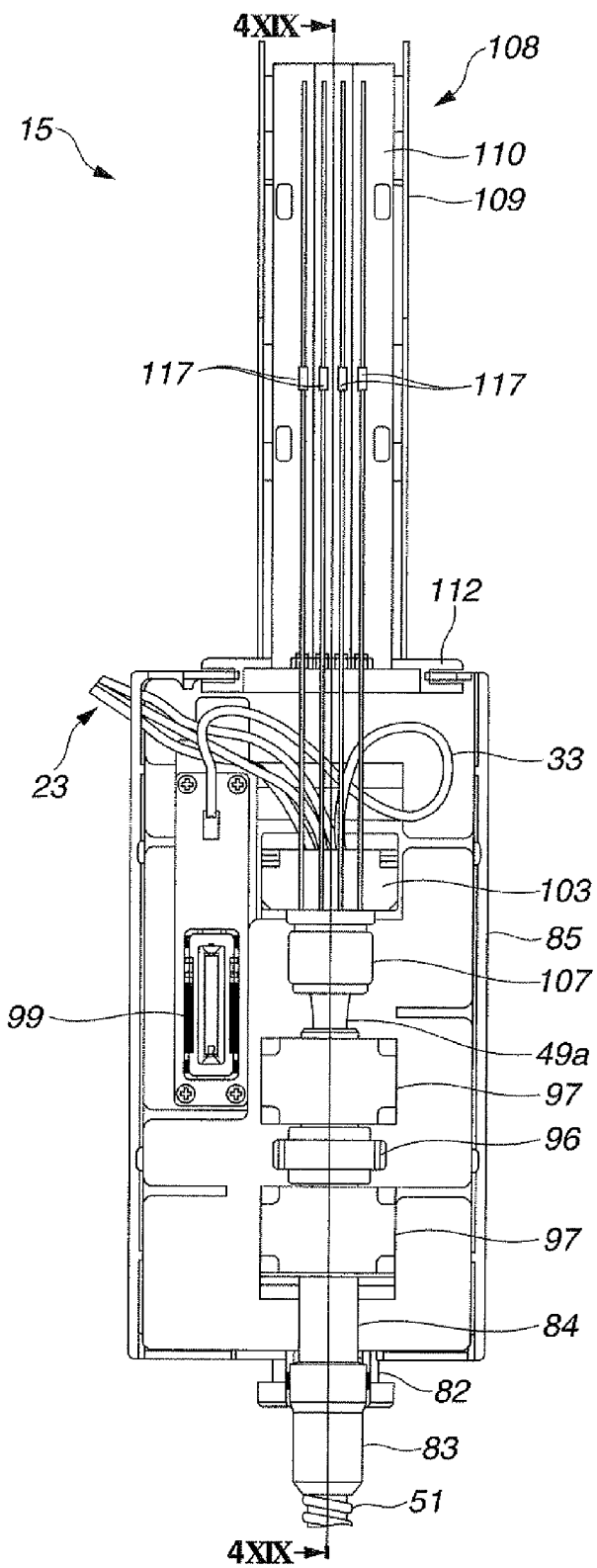
FIG. 48 is a rear view of the connector cover according to the embodiment.
Figure 49:
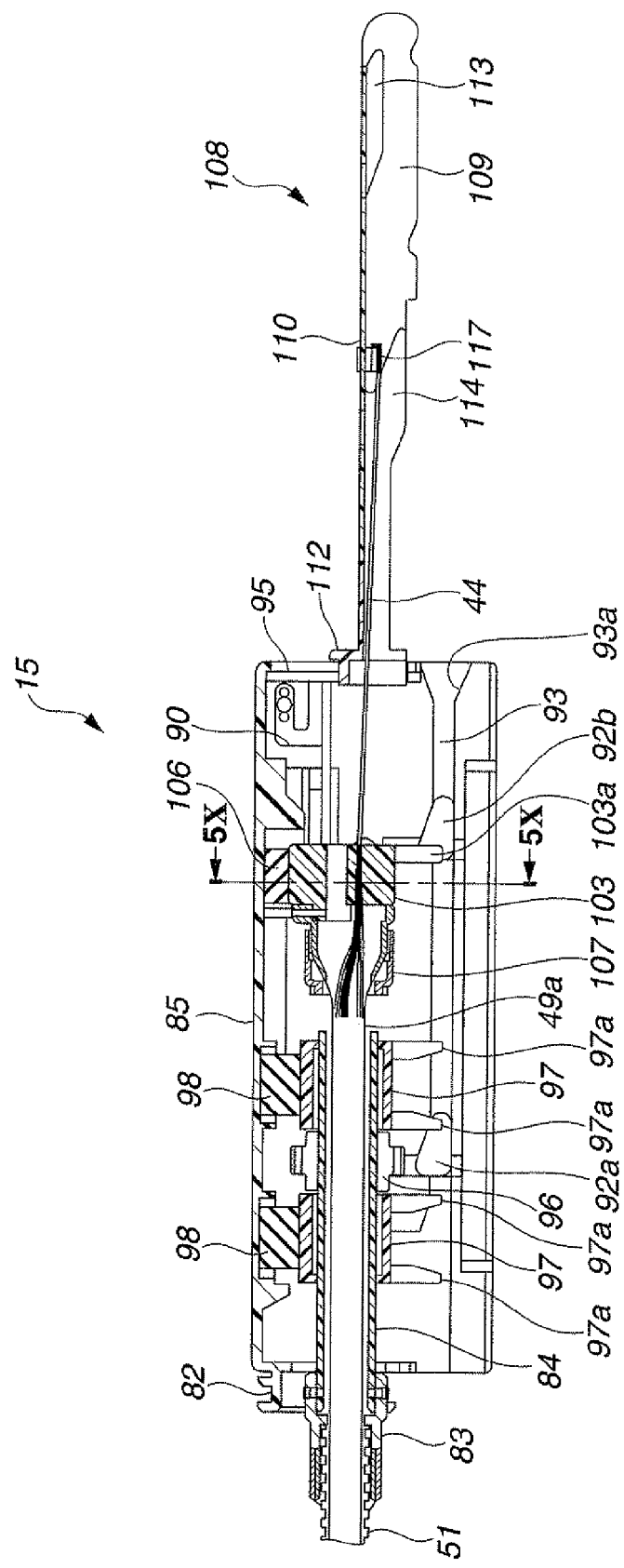
FIG. 49 is a sectional view of the connector cover along 4XIX-4XIX line in FIG. 48 according to the embodiment.
Figure 50:
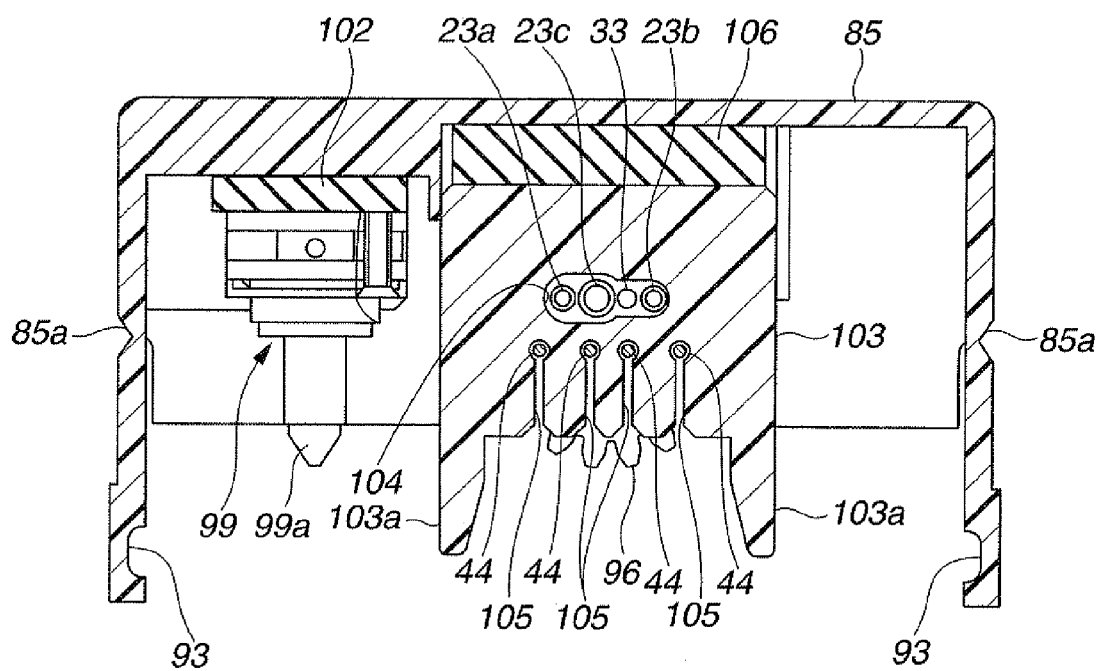
FIG. 50 is a sectional view of the connector cover along 5X-5X line in FIG. 49 according to the embodiment.
Figure 51:
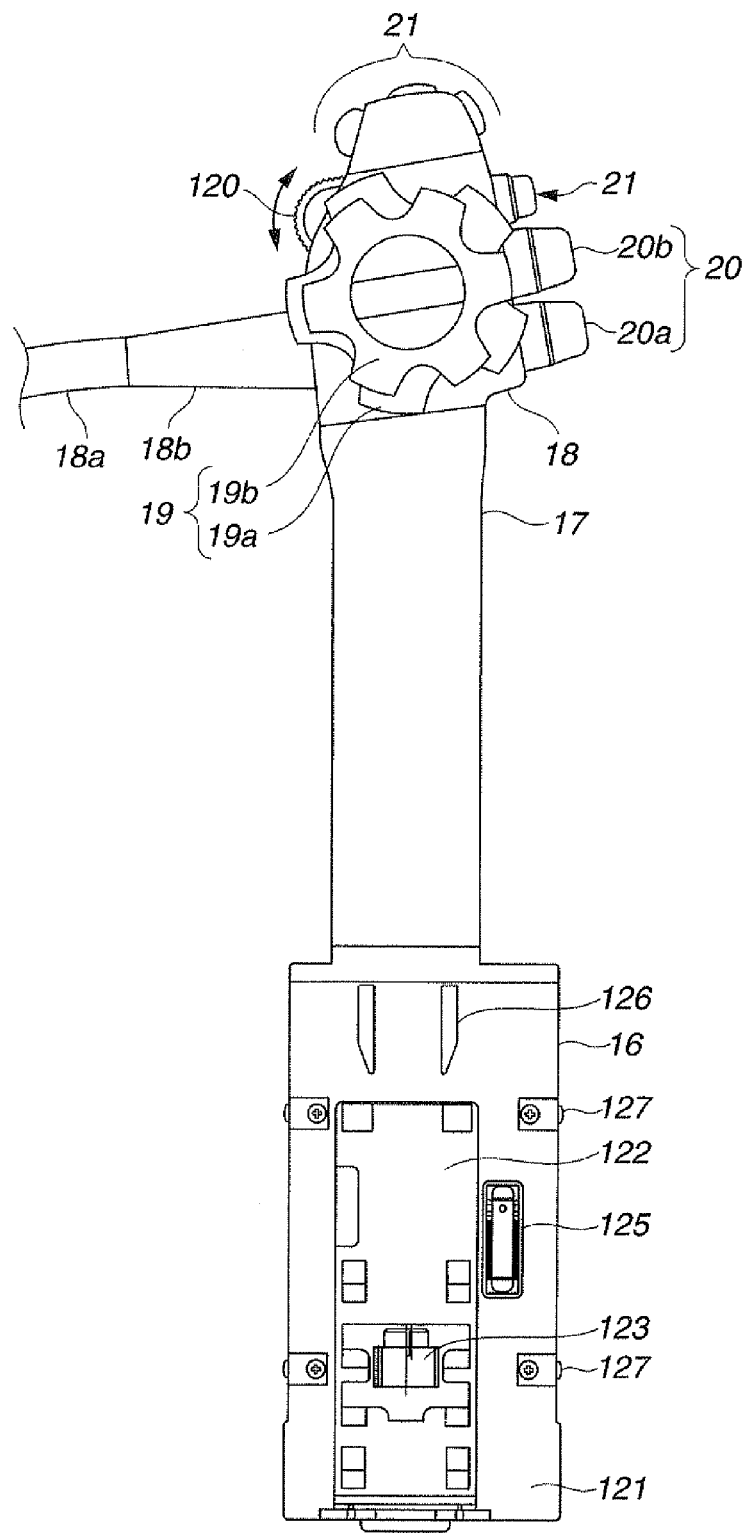
FIG. 51 is a top view showing the operation portion according to the embodiment.
Figure 52:
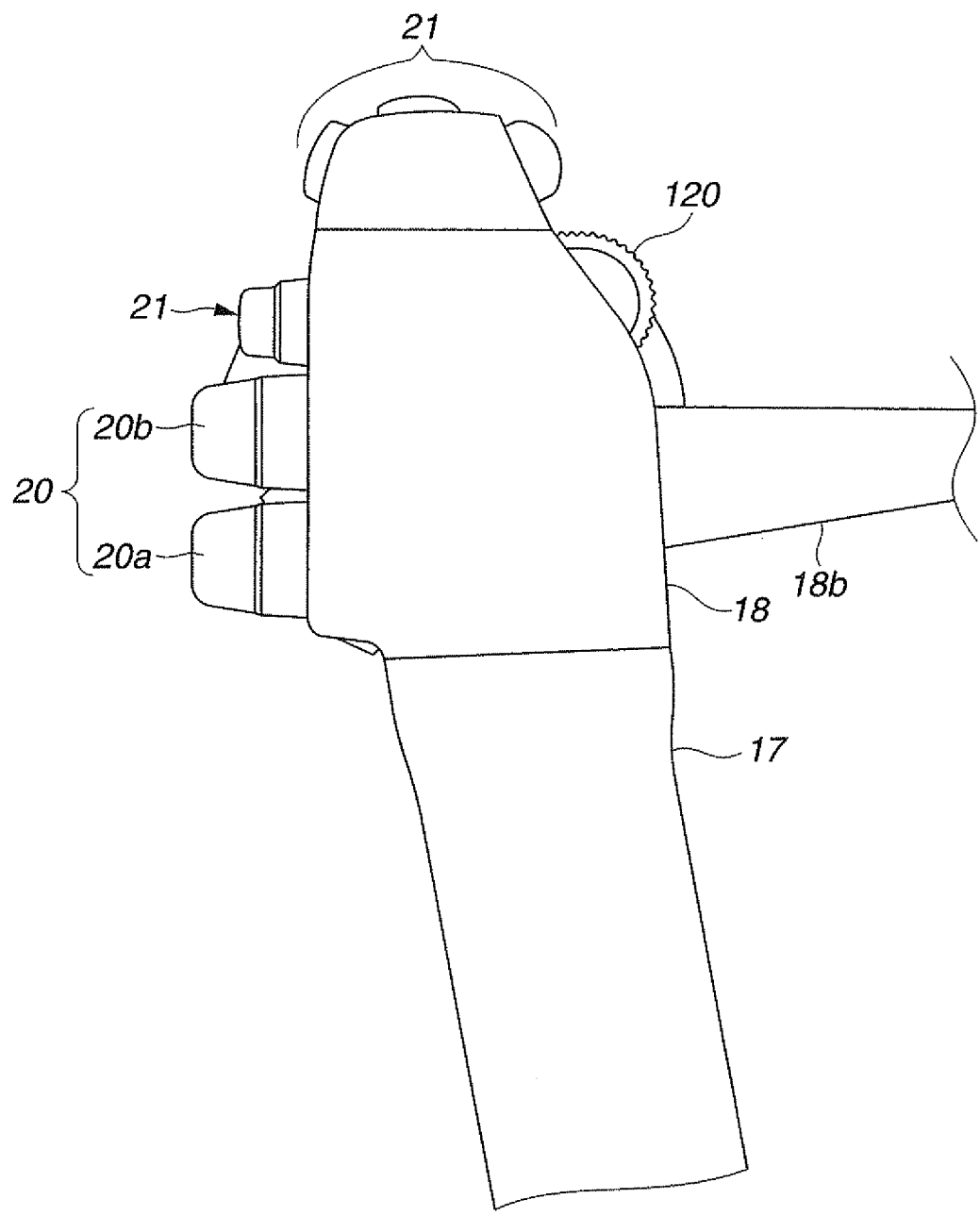
FIG. 52 is a plan view showing a rear surface of a main operation portion according to the embodiment.
Figure 53:
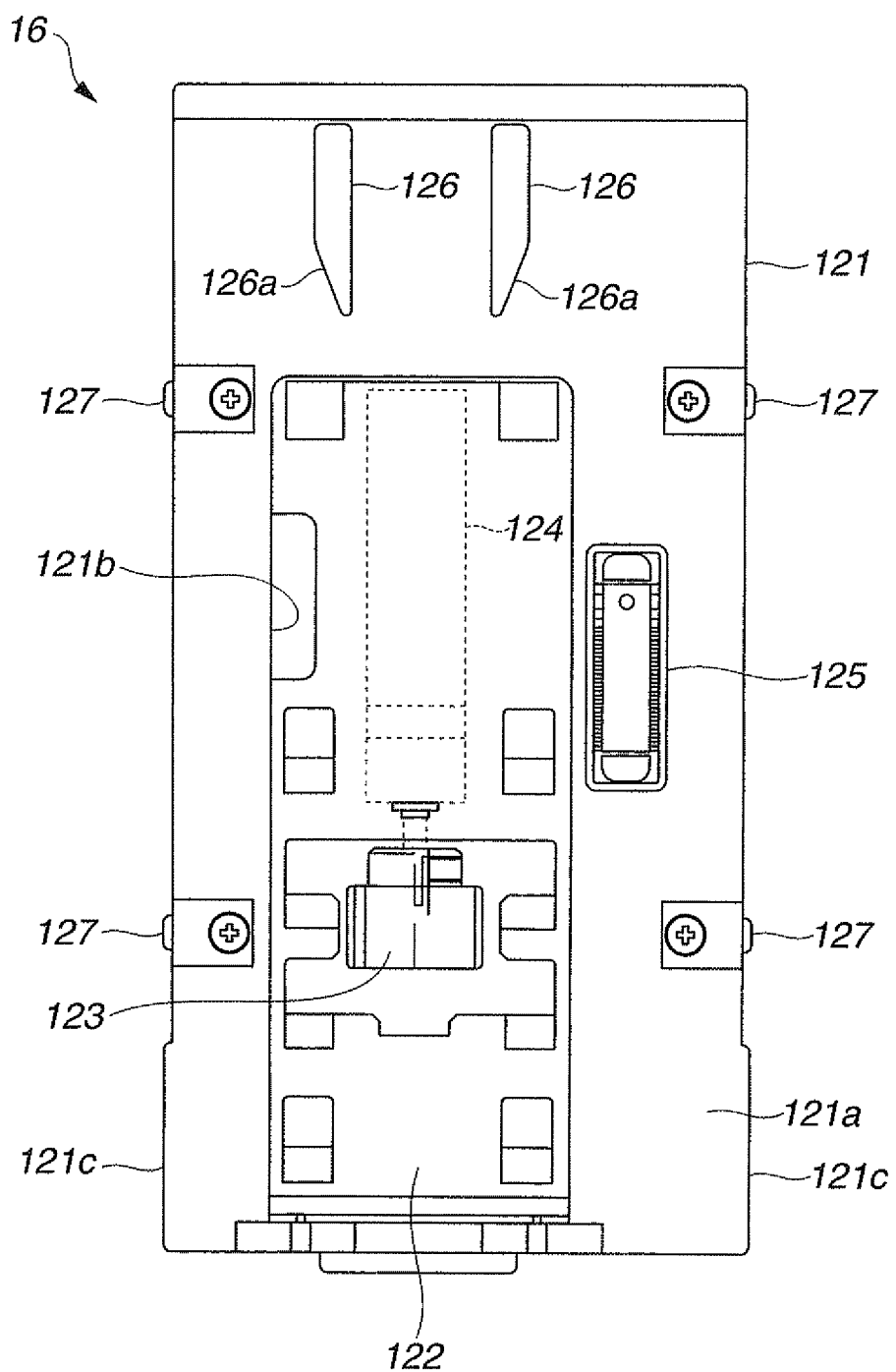
FIG. 53 is a top view showing a motor box according to the embodiment.
Figure 54:
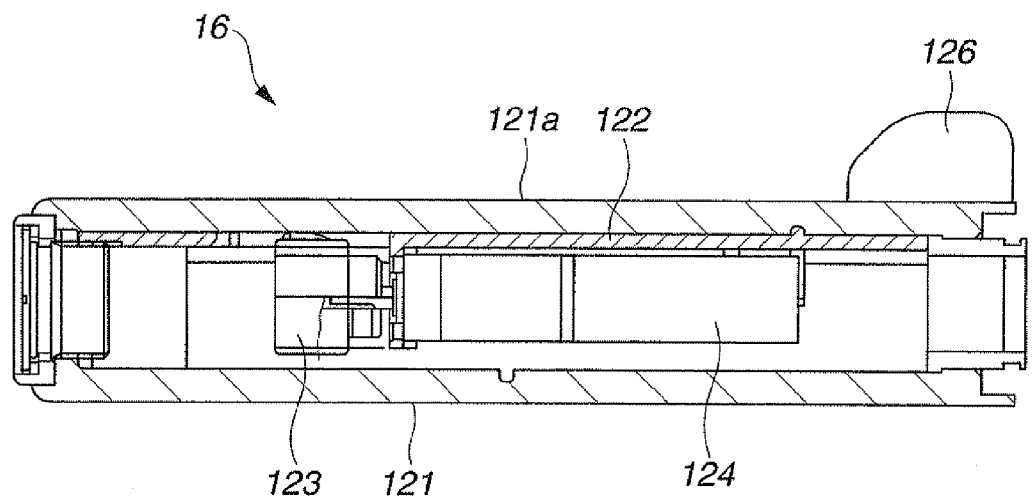
FIG. 54 is a sectional view of the motor box according to the embodiment.
Figure 55:
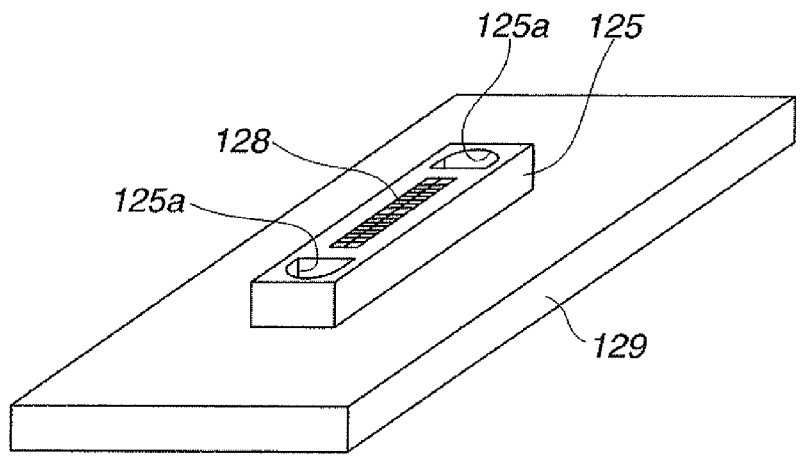
FIG. 55 is a perspective view showing an electric connector on a female side according to the embodiment.
Figure 56:
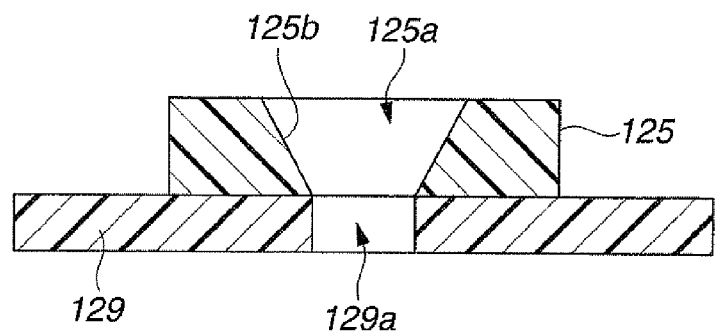
FIG. 56 is a sectional view in a lateral direction of the electric connector according to the embodiment.
Figure 57:
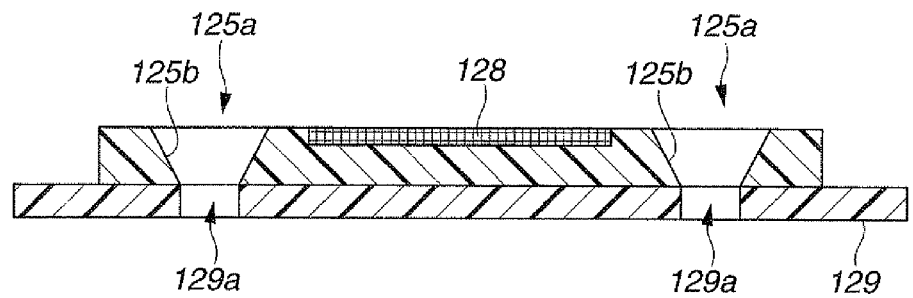
FIG. 57 is a sectional view in a longitudinal direction of the electric connector according to the embodiment.
Figure 58:
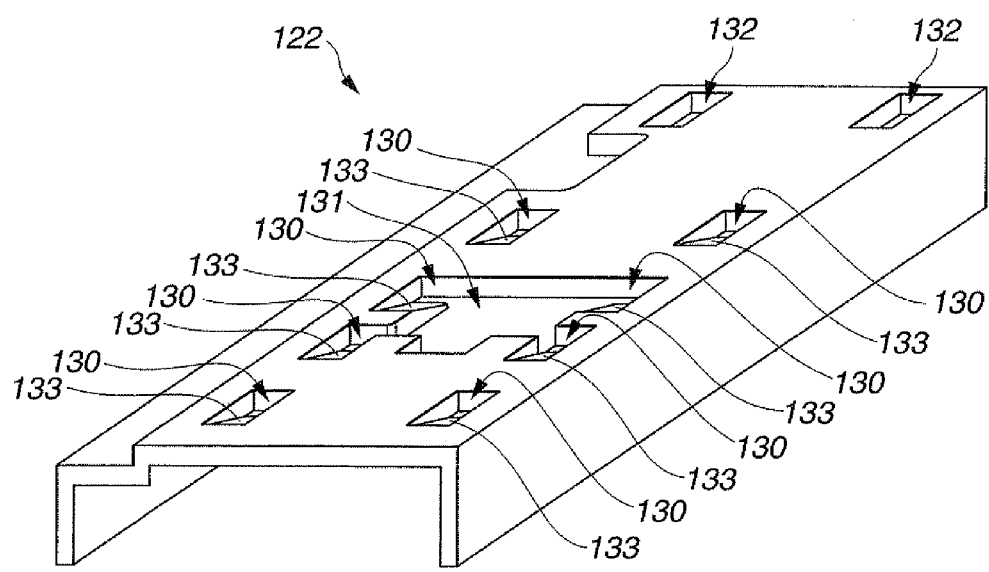
FIG. 58 is a perspective view showing a motor cover according to the embodiment.
Figure 59:
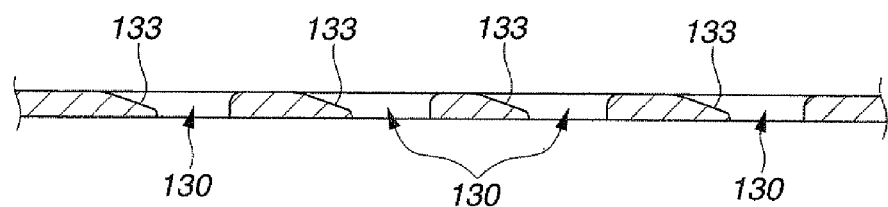
FIG. 59 is a sectional view for explaining an engaging hole of the motor cover according to the embodiment.
Figure 60:
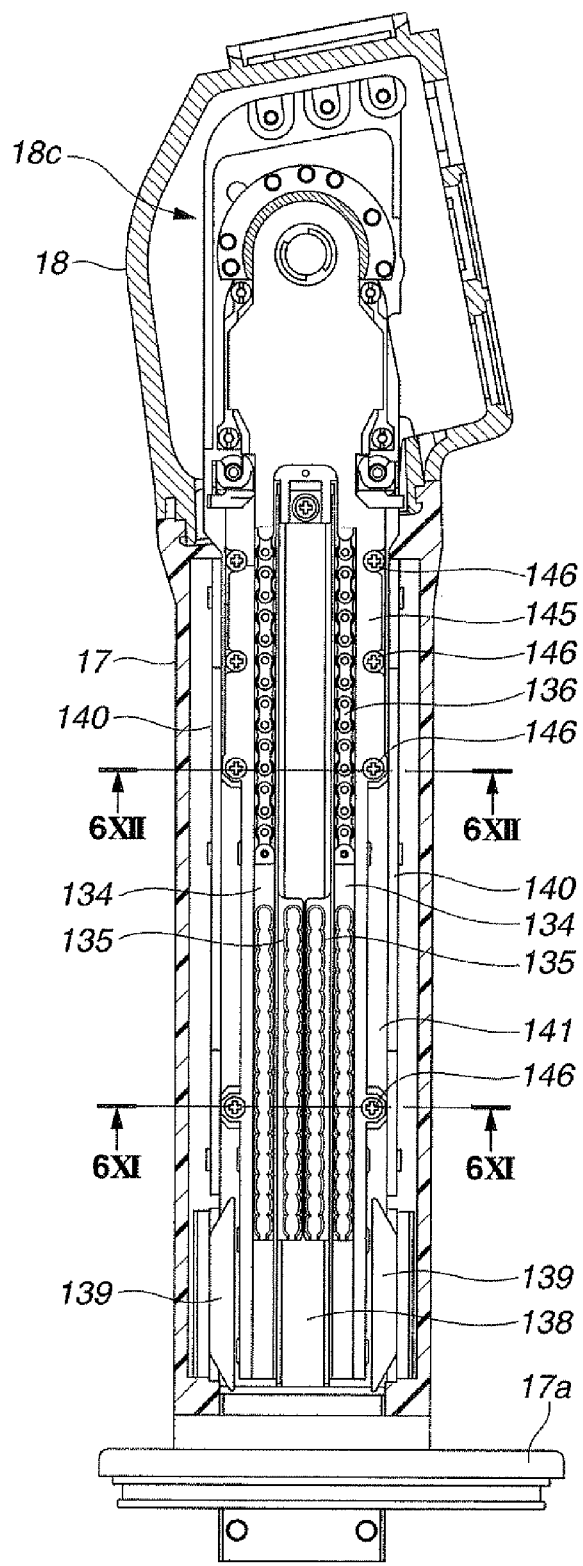
FIG. 60 is a diagram showing the internal structure of a grasping portion and the main operation portion according to the embodiment.
Figure 61:
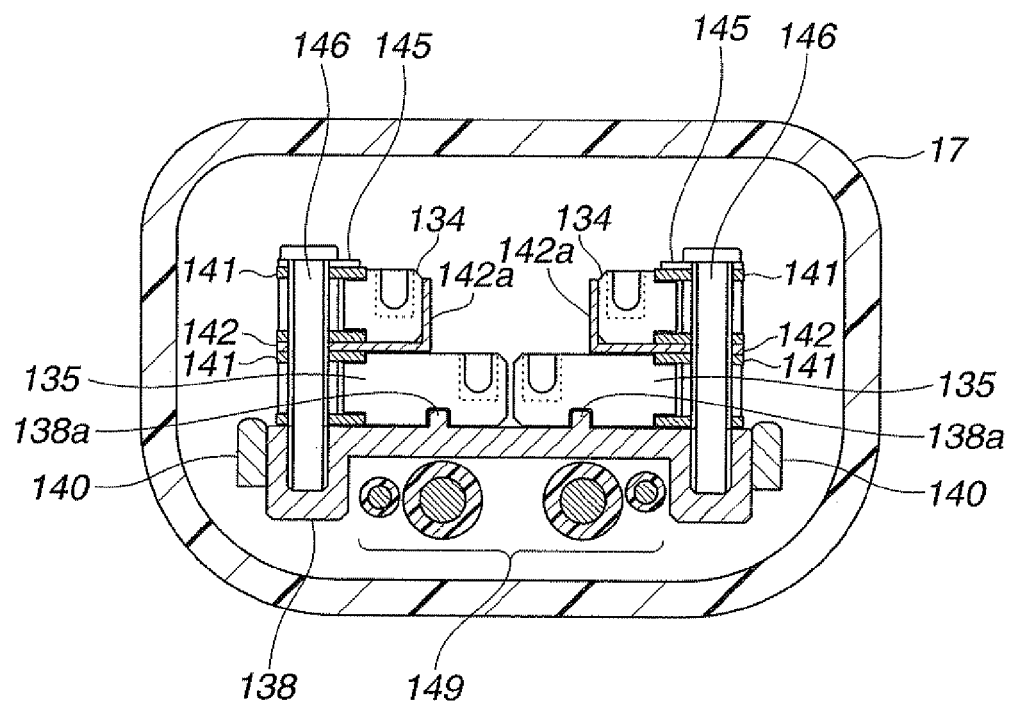
FIG. 61 is a sectional view of the grasping portion along 6XI-6XI line in FIG. 60 according to the embodiment.
Figure 62:
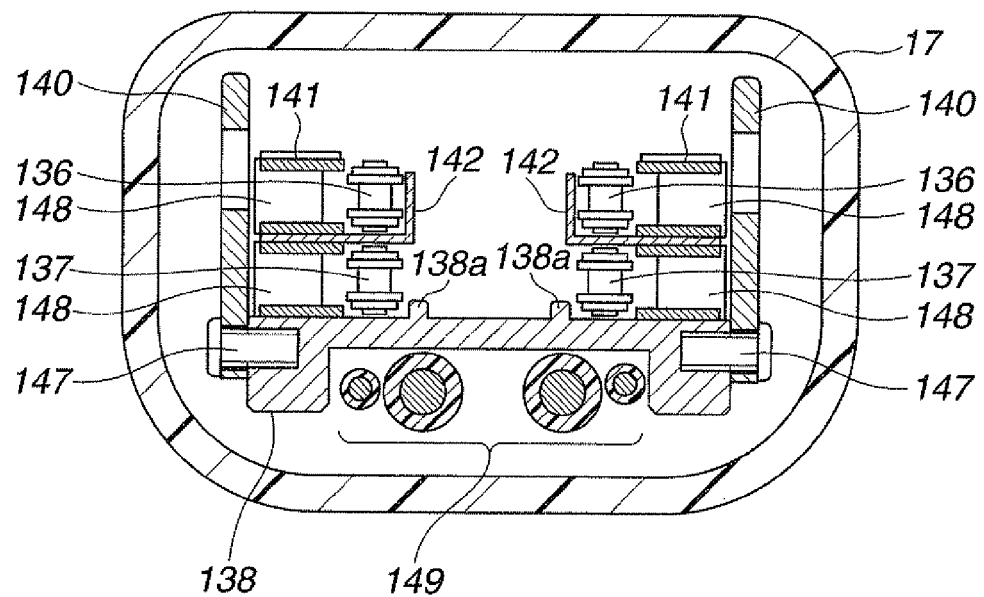
FIG. 62 is a sectional view of the grasping portion along 6XII-6XII line in FIG. 60 according to the embodiment.
Figure 63:
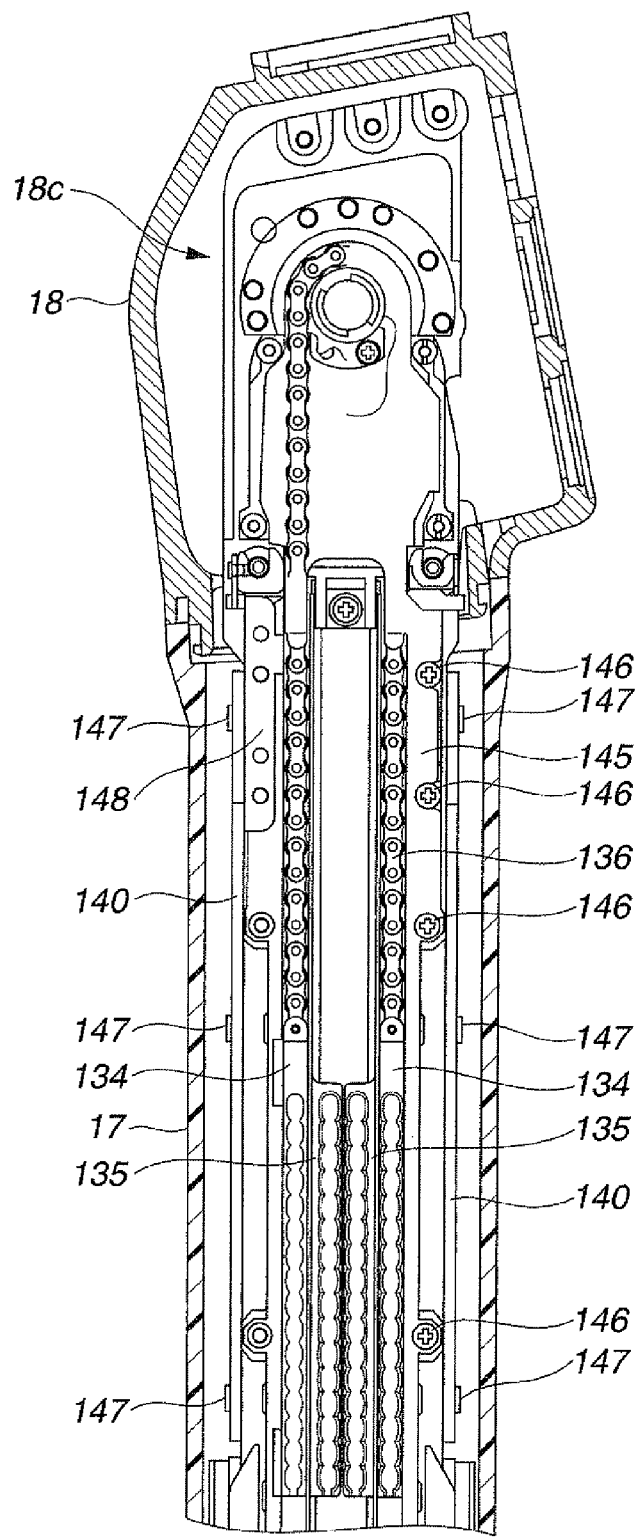
FIG. 63 is a diagram showing the internal structure of the grasping portion and the main operation portion according to the embodiment.
Figure 64:
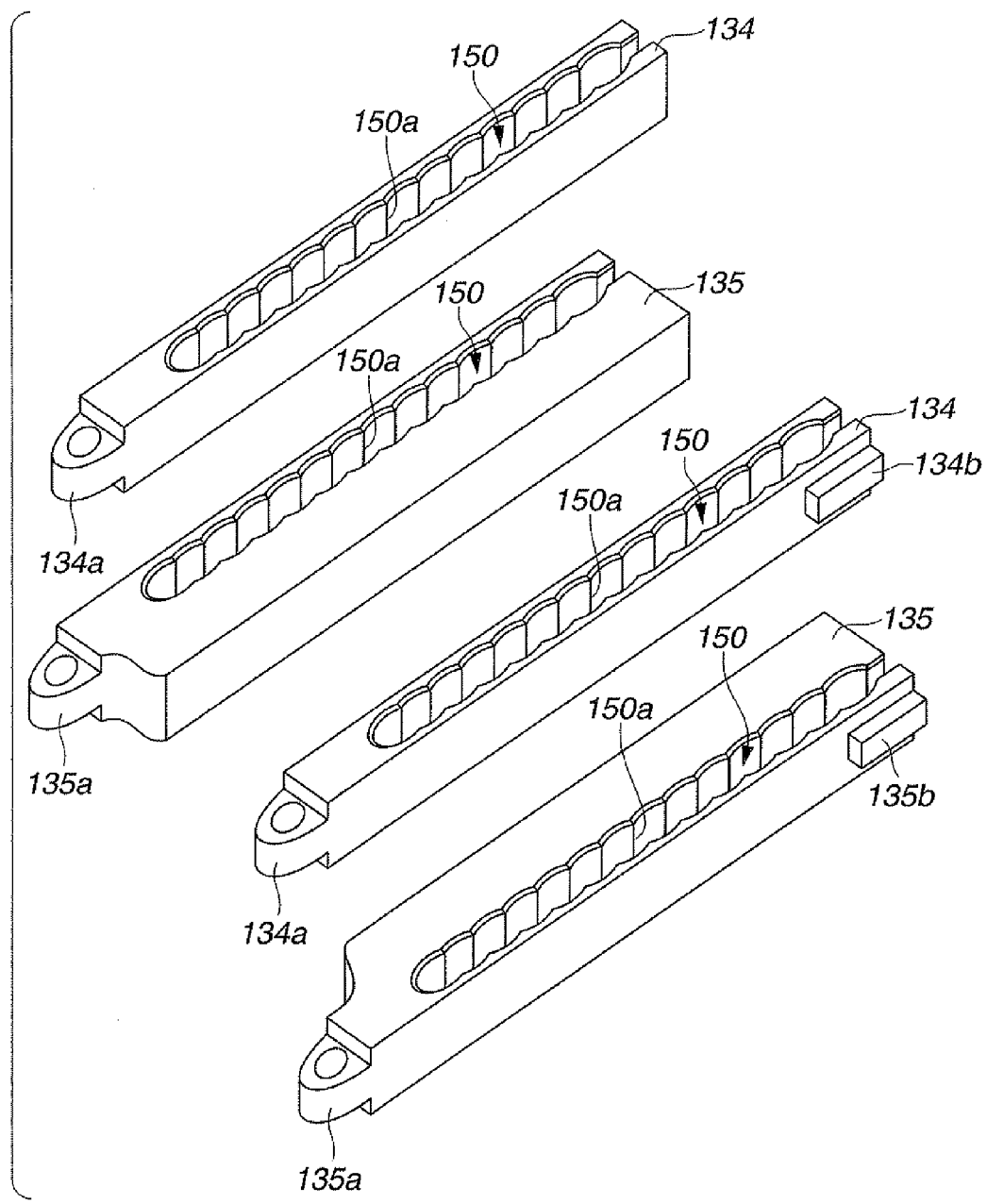
FIG. 64 is a perspective view showing a coupling member according to the embodiment.
Figure 65:
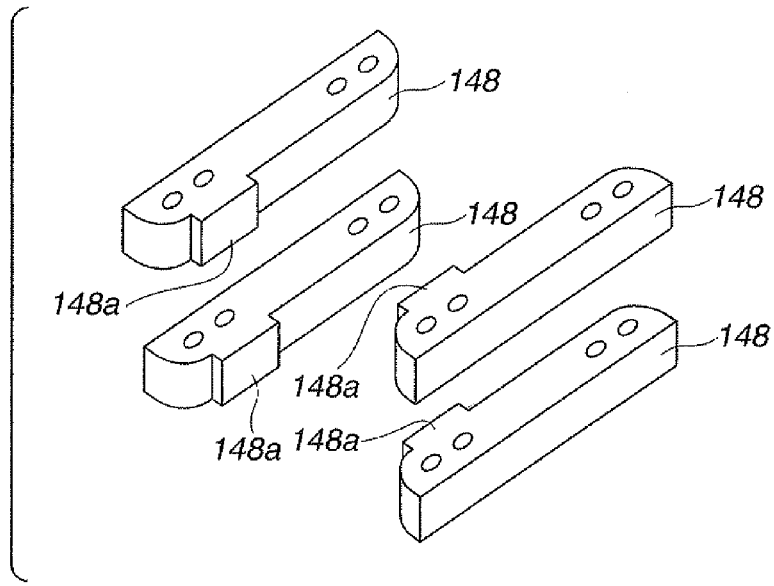
FIG. 65 is a perspective view showing a stopper according to the embodiment.
Figure 66:
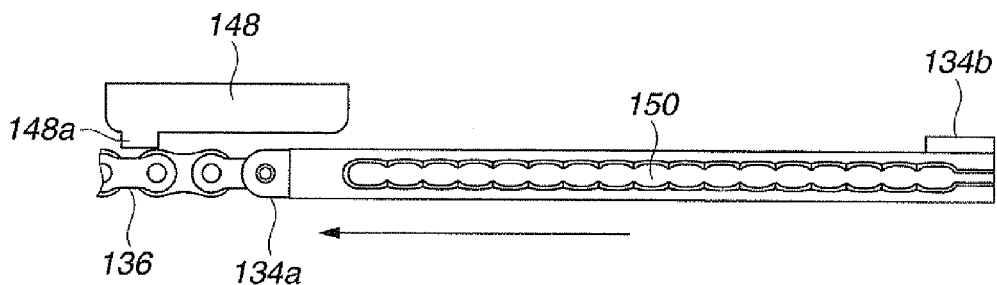
FIG. 66 is a diagram for explaining a state in which the coupling member comes into contact with the stopper according to the embodiment.
Figure 67:
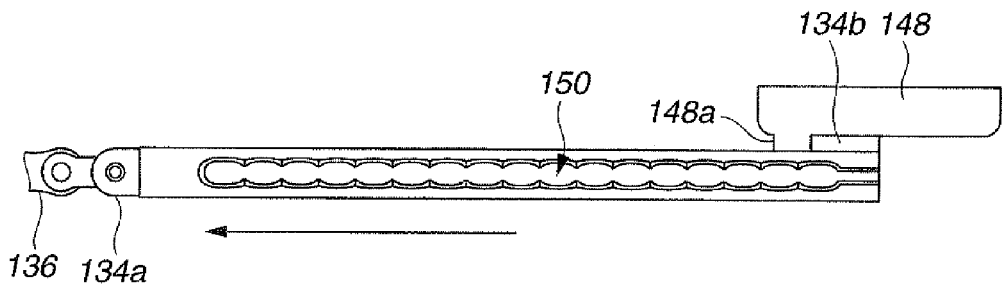
FIG. 67 is a diagram for explaining the state in which the coupling member comes into contact with the stopper according to the embodiment.
Figure 68:
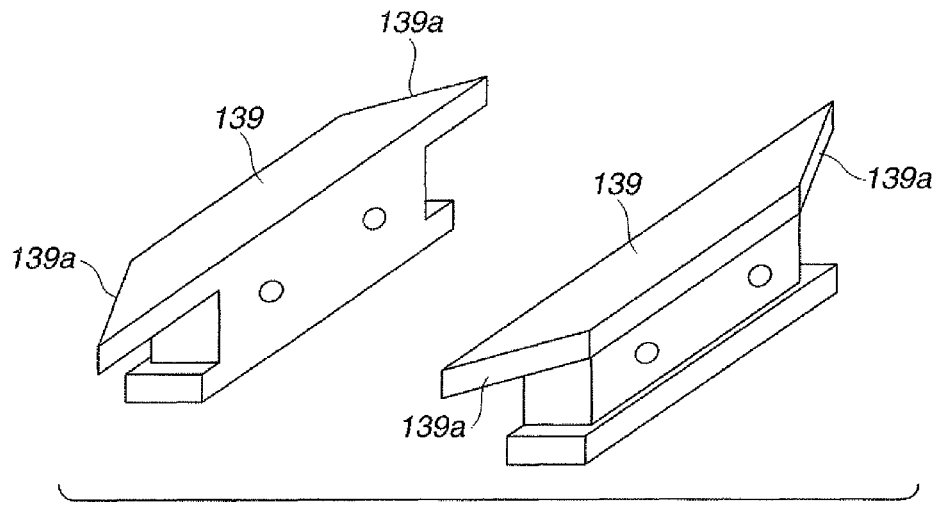
FIG. 68 is a perspective view showing a first guide plate according to the embodiment.
Figure 69:
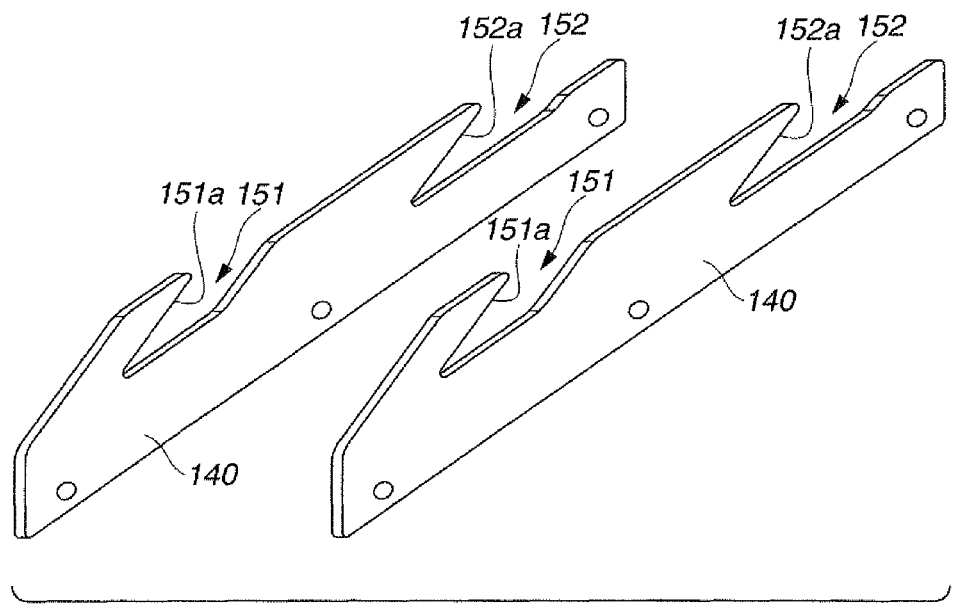
FIG. 69 is a perspective view showing a second guide plate according to the embodiment.
Figure 70:
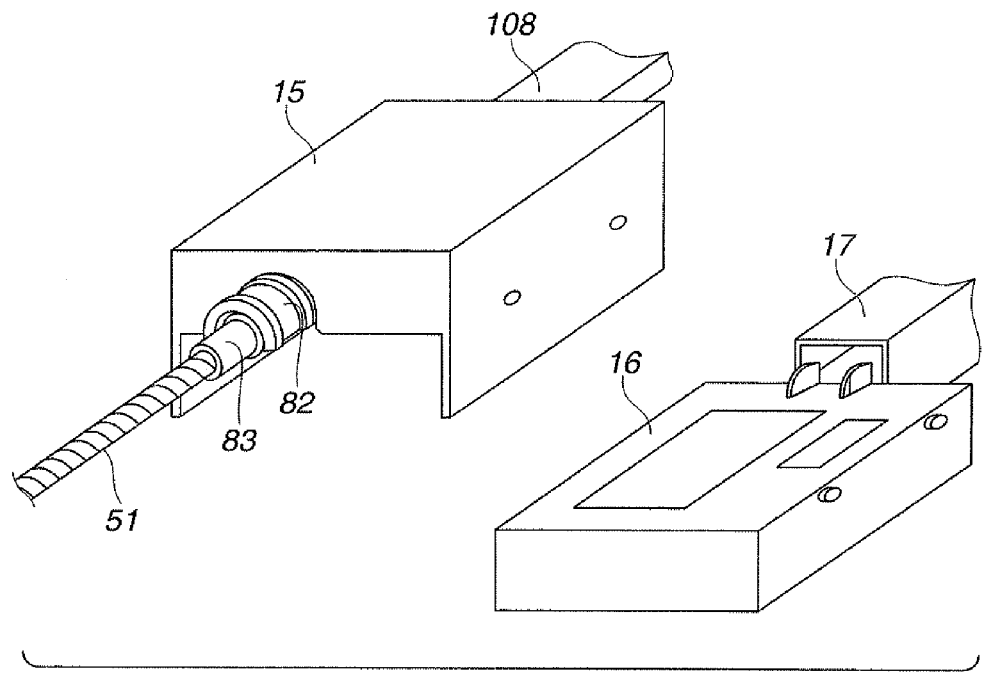
FIG. 70 is a perspective view showing a state before the connector cover docks with the motor box according to the embodiment.
Figure 71:
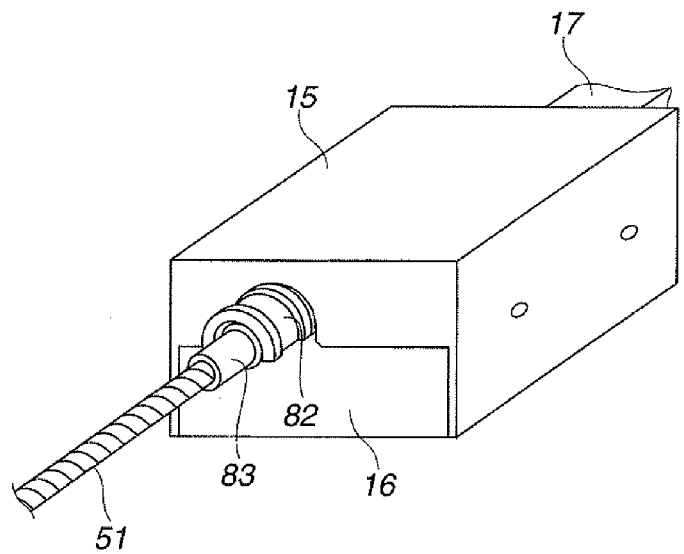
FIG. 71 is a perspective view showing a state in which the connector cover docks with the motor box according to the embodiment.
Figure 72:
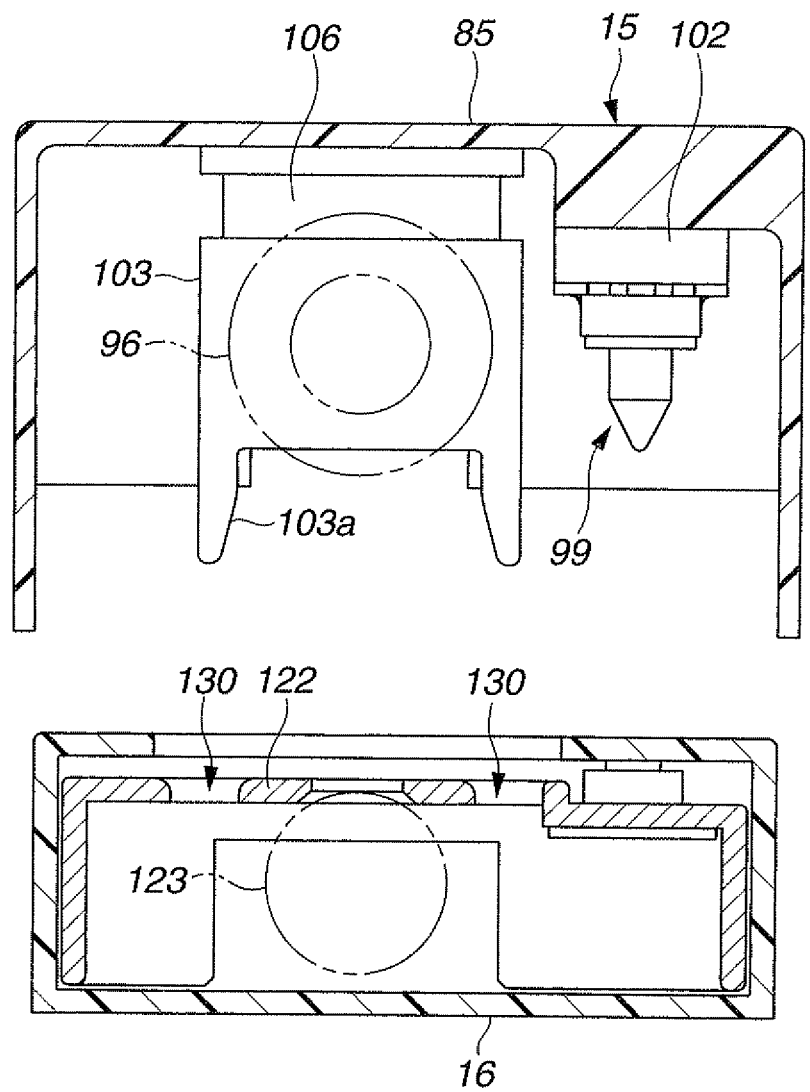
FIG. 72 is a sectional view showing the state before the connector cover docks with the motor box according to the embodiment.
Figure 73:
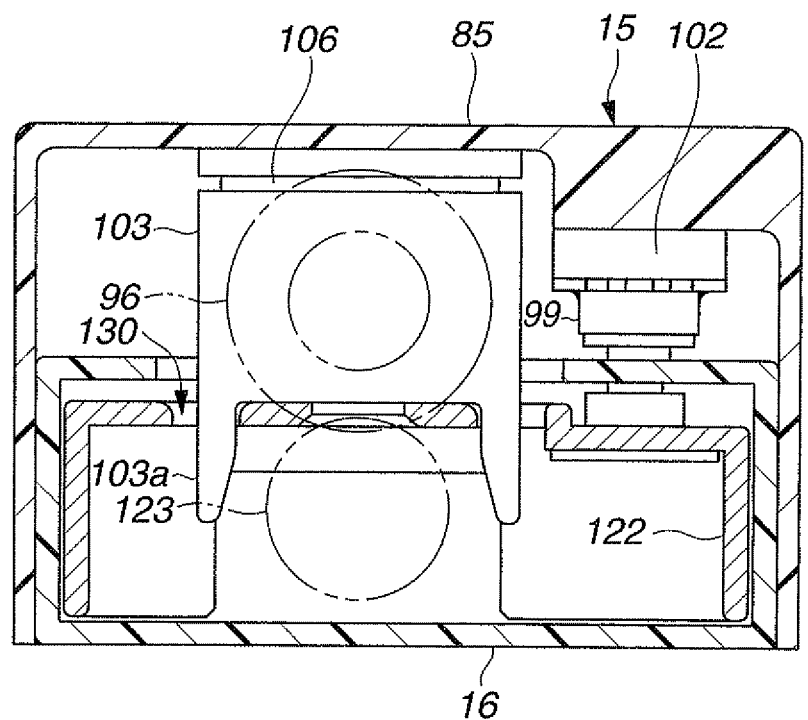
FIG. 73 is a sectional view showing the state in which the connector cover docks with the motor box according to the embodiment.
Figure 74:
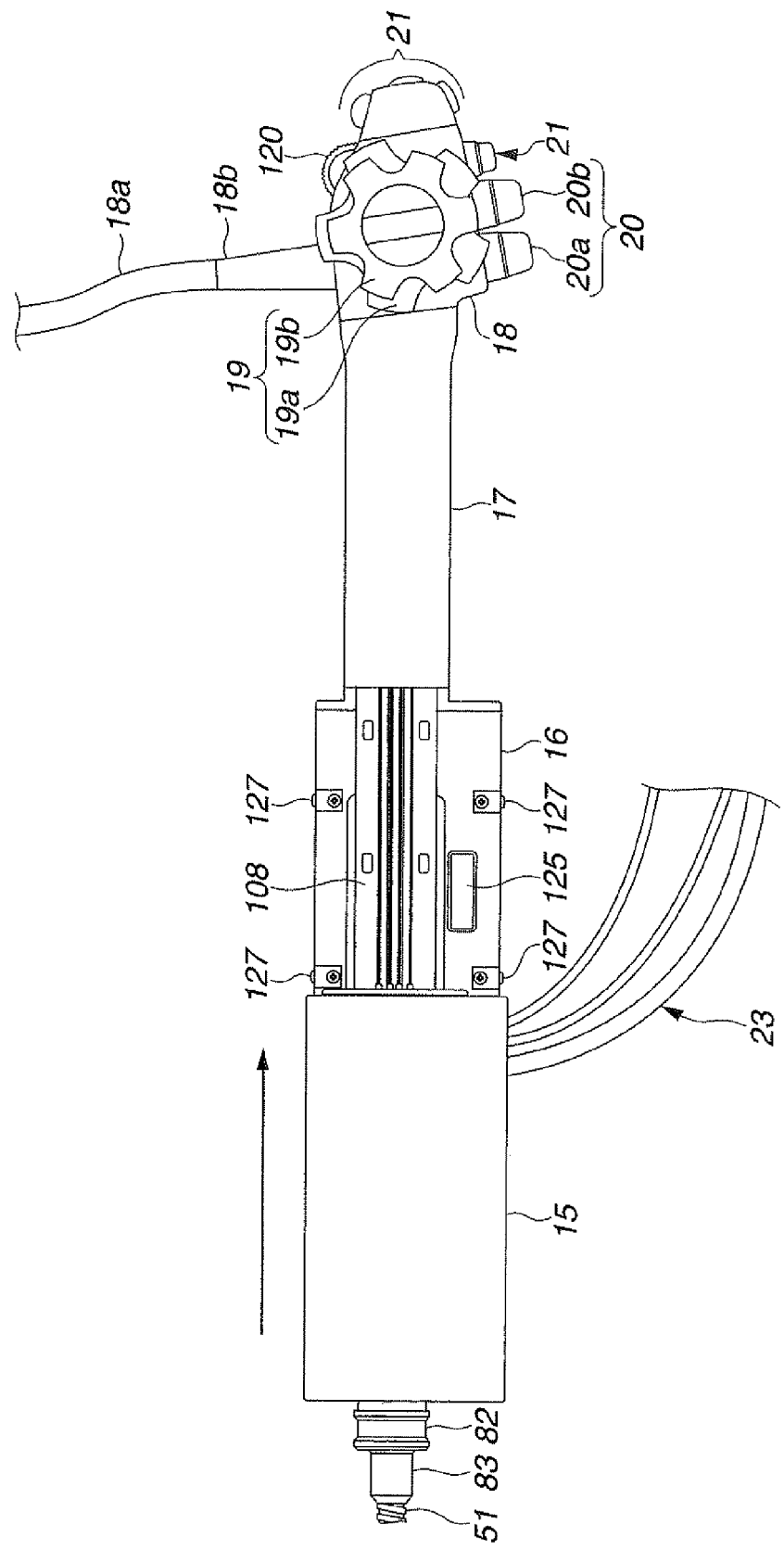
FIG. 74 is a top view showing the state before the connector cover docks with the motor box according to the embodiment.
Figure 75:
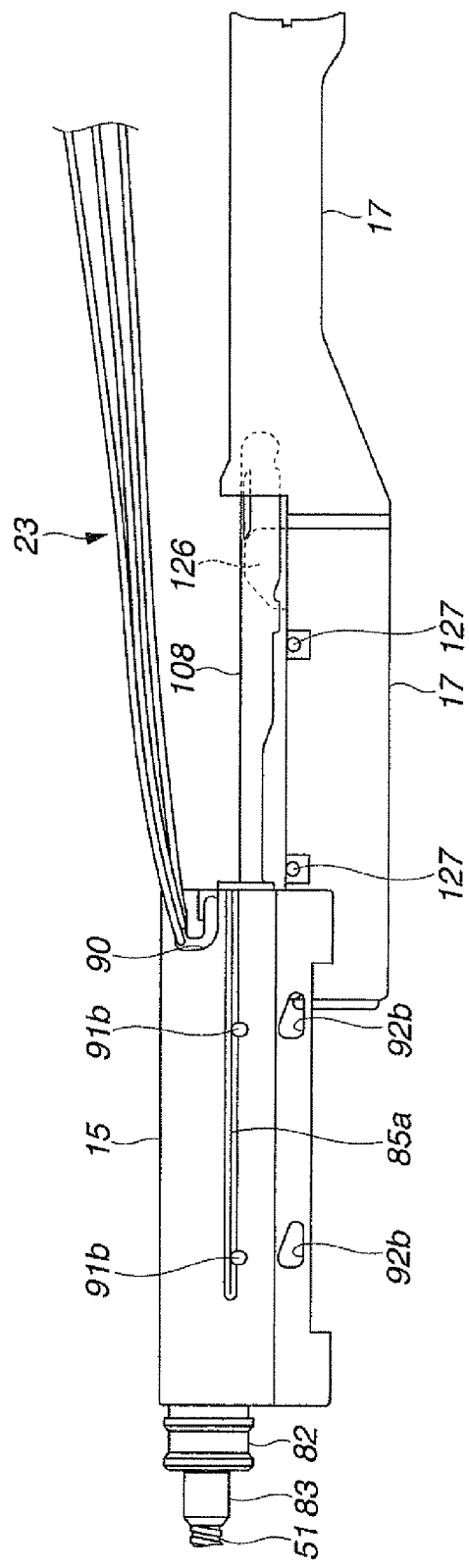
FIG. 75 is a side view showing the state before the connector cover docks with the motor box according to the embodiment.
Figure 76:
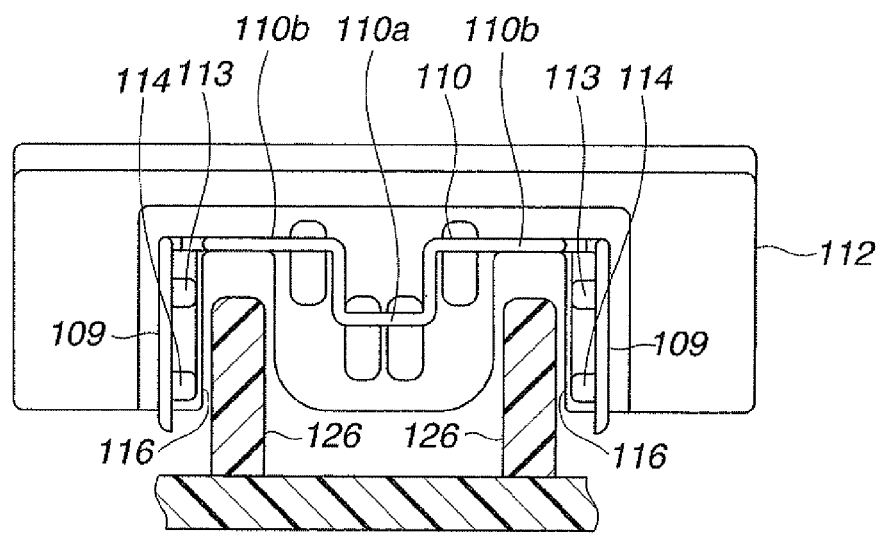
FIG. 76 is a partial sectional view showing a state in which the wire connection plate is guided by a guide plate according to the embodiment.
Figure 77:
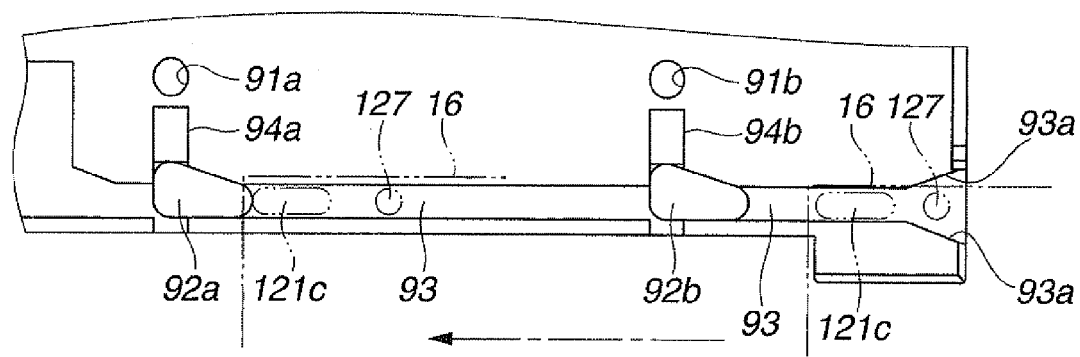
FIG. 77 is a diagram for explaining a state in which an engaging convex portion of the motor box is guided by a linear groove of the connector cover according to the embodiment.
Figure 78:
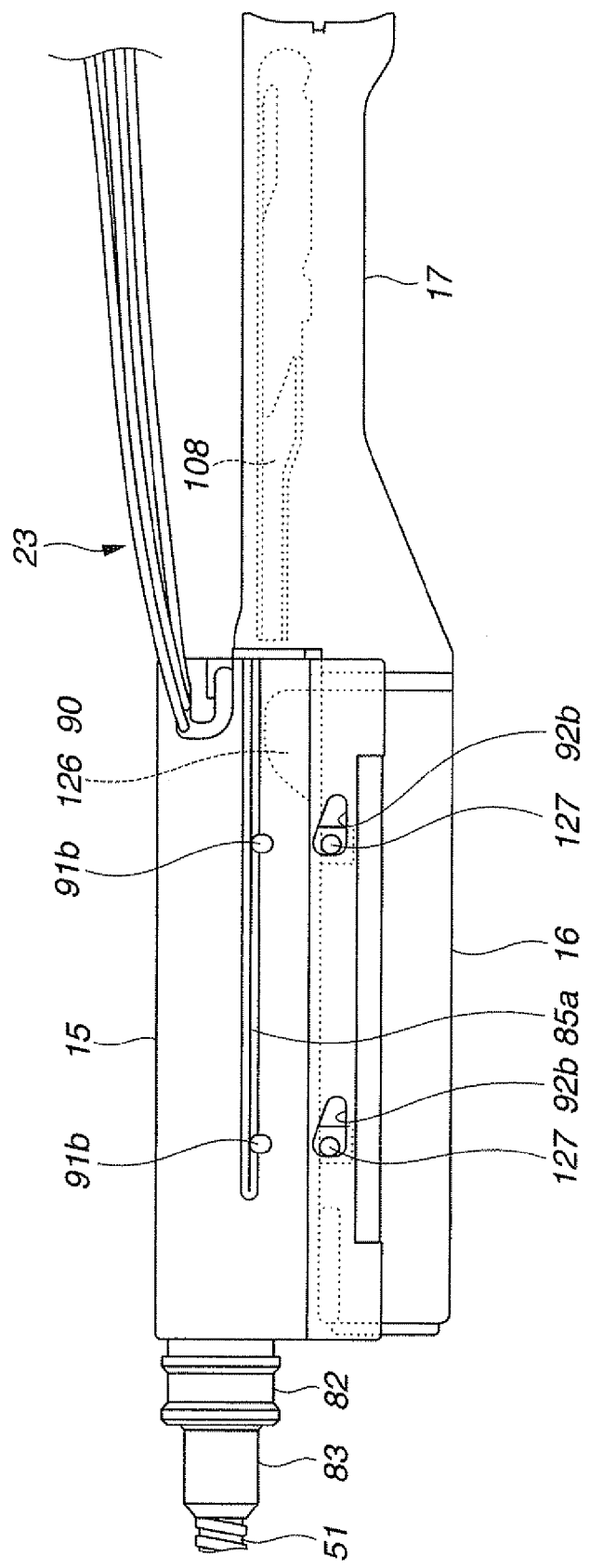
FIG. 78 is a side view showing a state immediately before the connector cover docks with the motor box according to the embodiment.
Figure 79:
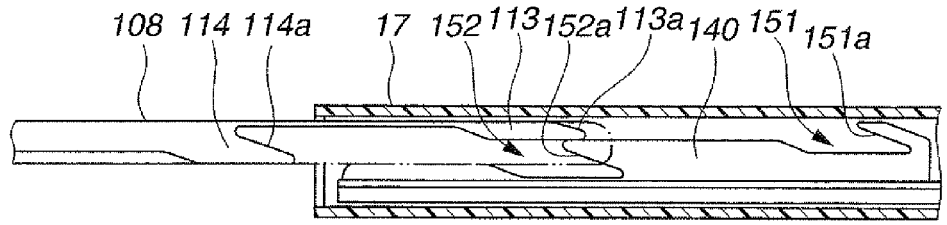
FIG. 79 is a diagram for explaining a state in which the wire connection plate is guided by a second guide plate according to the embodiment.
Figure 80:
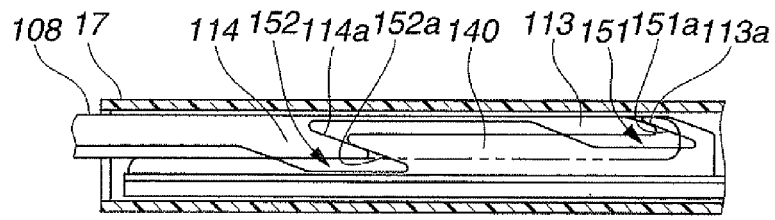
FIG. 80 is a diagram for explaining the state in which the wire connection plate is guided by the second guide plate according to the embodiment.
Figure 81:
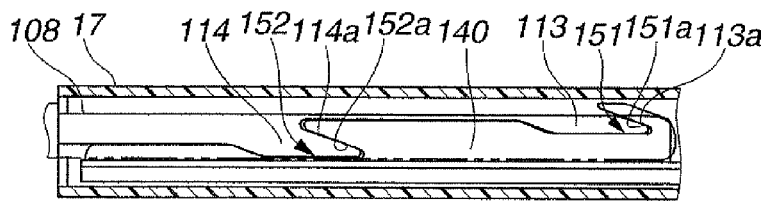
FIG. 81 is a diagram for explaining the state in which the wire connection plate is guided by the second guide plate according to the embodiment.
Figure 89:
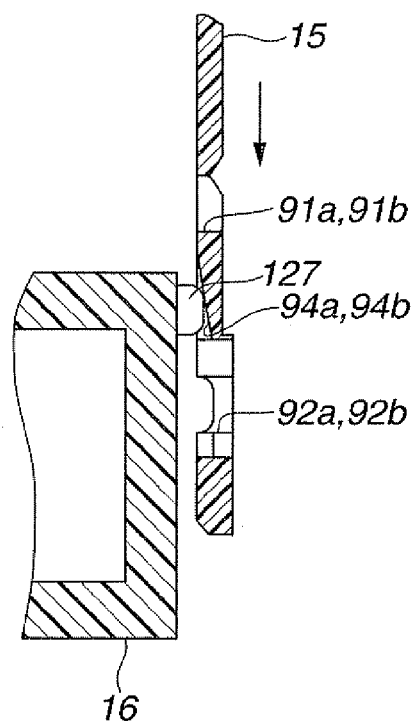
FIG. 89 is a diagram for explaining the state in which the engaging convex portion of the motor box is inserted in the engaging hole while being guided by the guide groove of the connector cover and the inclined surface according to the embodiment.
Figure 90:
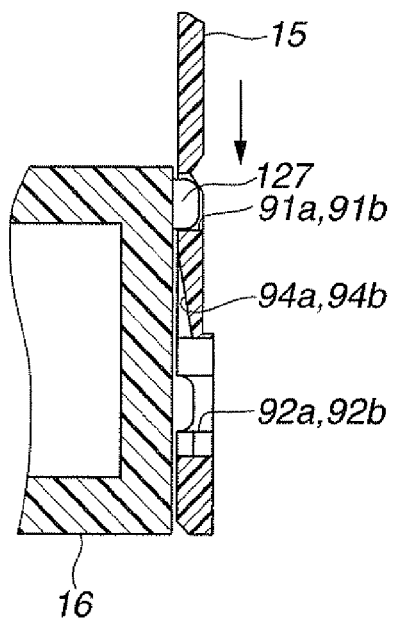
FIG. 90 is a diagram for explaining the state in which the engaging convex portion of the motor box is inserted in the engaging hole while being guided by the guide groove of the connector cover and the inclined surface according to the embodiment.
Figure 91:
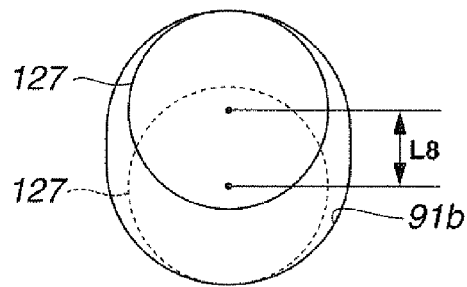
FIG. 91 is an enlarged plan view showing a state in which the engaging convex portion is inserted in the engaging hole according to the embodiment.
Figure 92:
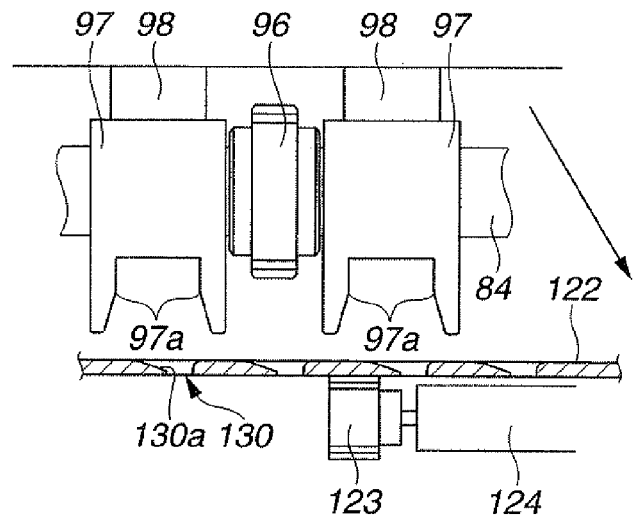
FIG. 92 is a diagram for explaining a state in which an engaging leg portion of the bearing is inserted in the engaging hole of the motor cover according to the embodiment.
Figure 93:
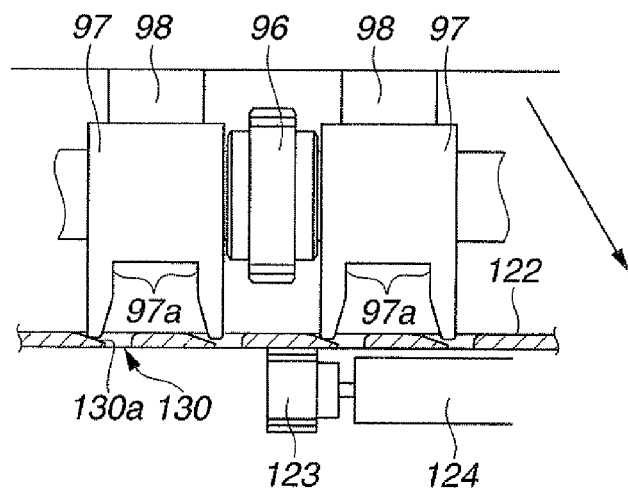
FIG. 93 is a diagram for explaining the state in which the engaging leg portion of the bearing is inserted in the engaging hole of the motor cover according to the embodiment.
Figure 94:
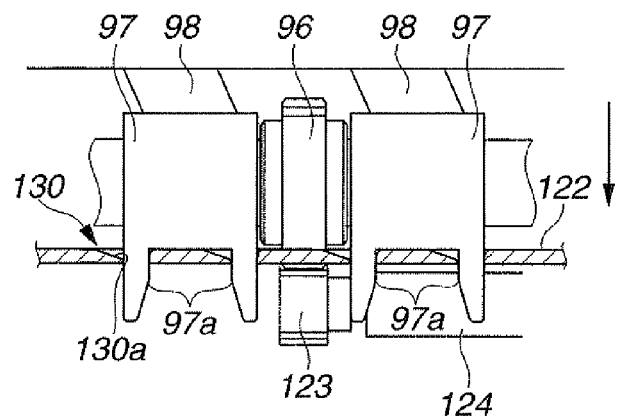
FIG. 94 is a diagram for explaining the state in which the engaging leg portion of the bearing is inserted in the engaging hole of the motor cover according to the embodiment.
Figure 95:
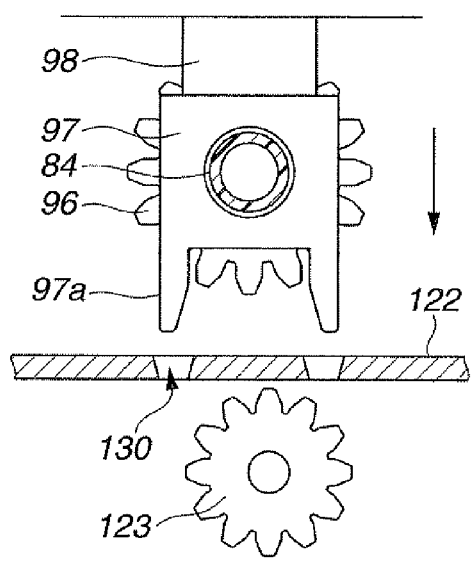
FIG. 95 is a diagram for explaining a state in which the engaging leg portion of the bearing is inserted in the engaging hole of the motor cover and an insertion portion side gear and a motor gear mesh with each other according to the embodiment.
Figure 96:
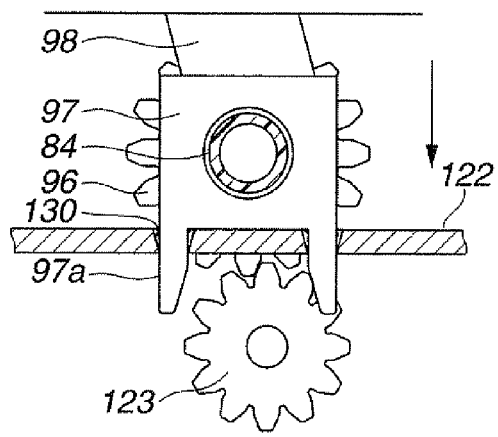
FIG. 96 is a diagram for explaining the state in which the engaging leg portion of the bearing is inserted in the engaging hole of the motor cover and the insertion portion side gear and the motor gear mesh with each other according to the embodiment.
Figure 97:
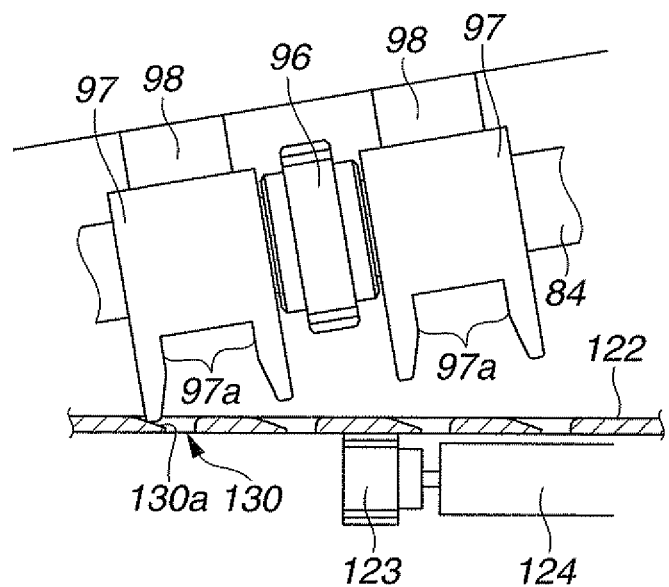
FIG. 97 is a diagram for explaining an action of an elastic member fastened to the bearing according to the embodiment.
Figure 98:
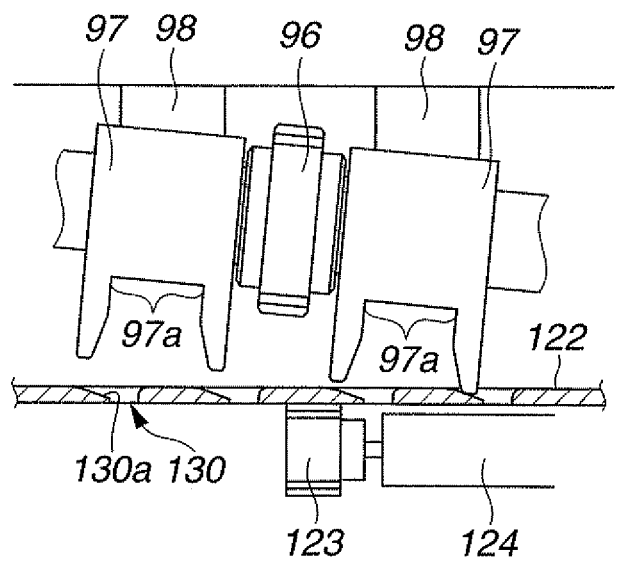
FIG. 98 is a diagram for explaining the action of the elastic member fastened to the bearing according to the embodiment.
Figure 99:
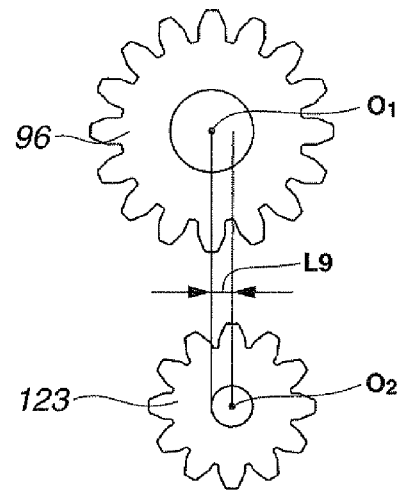
FIG. 99 is a diagram for explaining an action in the meshing of the insertion portion side gear and the motor gear according to the embodiment.
Figure 100:
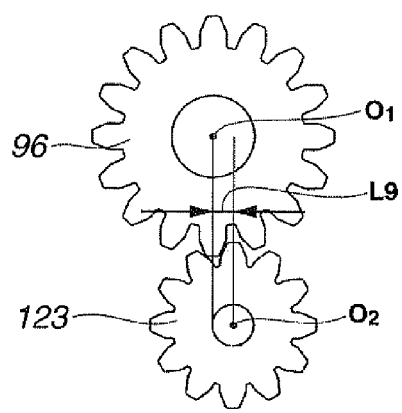
FIG. 100 is a diagram for explaining the action in the meshing of the insertion portion side gear and the motor gear according to the embodiment.
Figure 101:
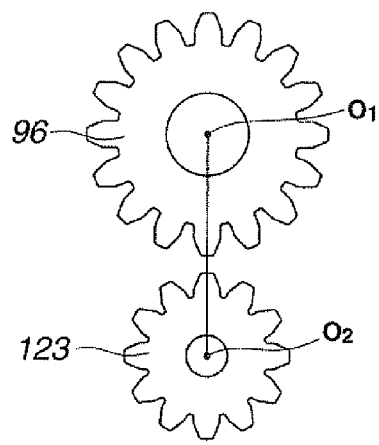
FIG. 101 is a diagram for explaining the action in the meshing of the insertion portion side gear and the motor gear according to the embodiment.
Figure 106:
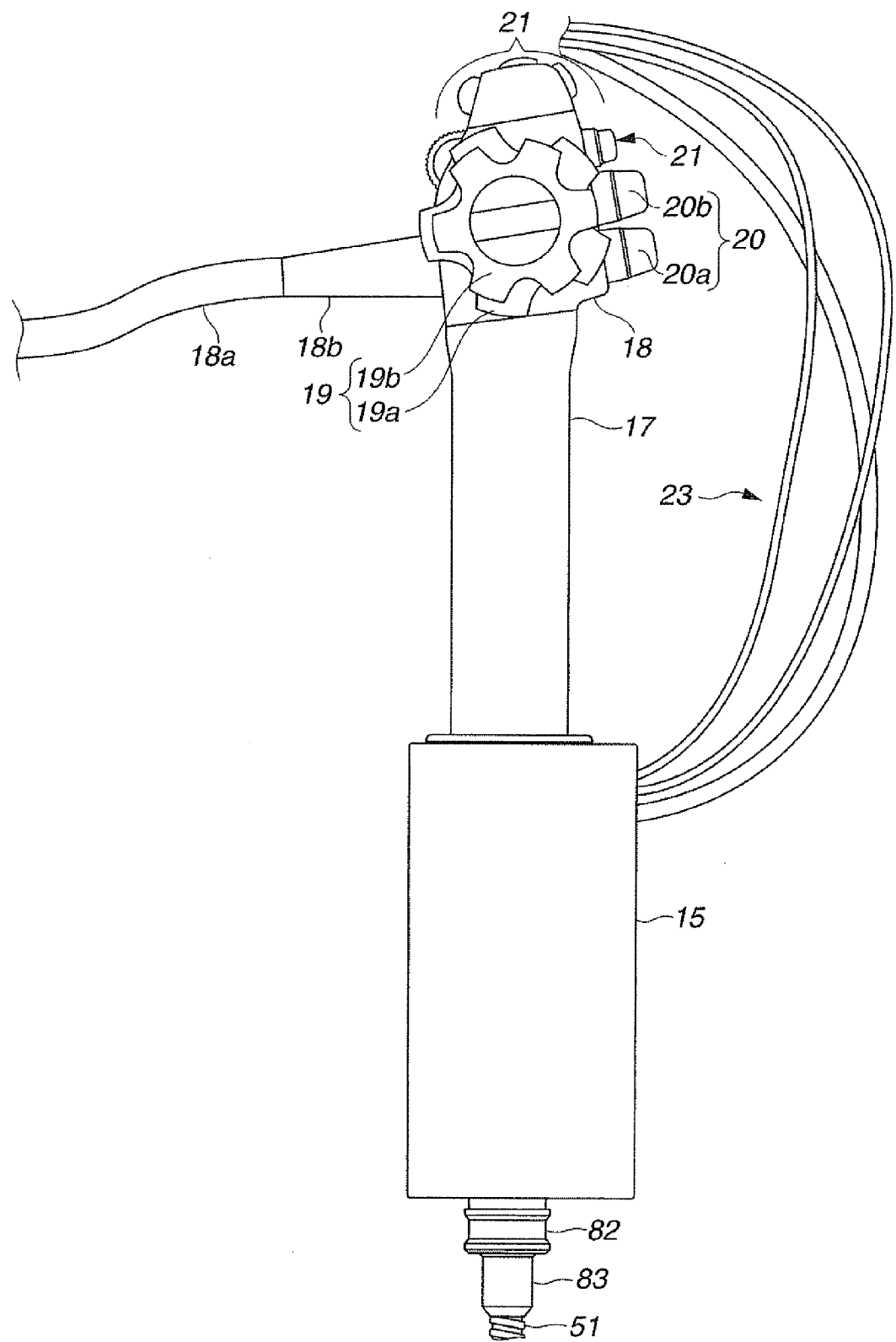
FIG. 106 is a top view showing a state in which the connector cover docks with the motor box according to the embodiment.
Figure 107:
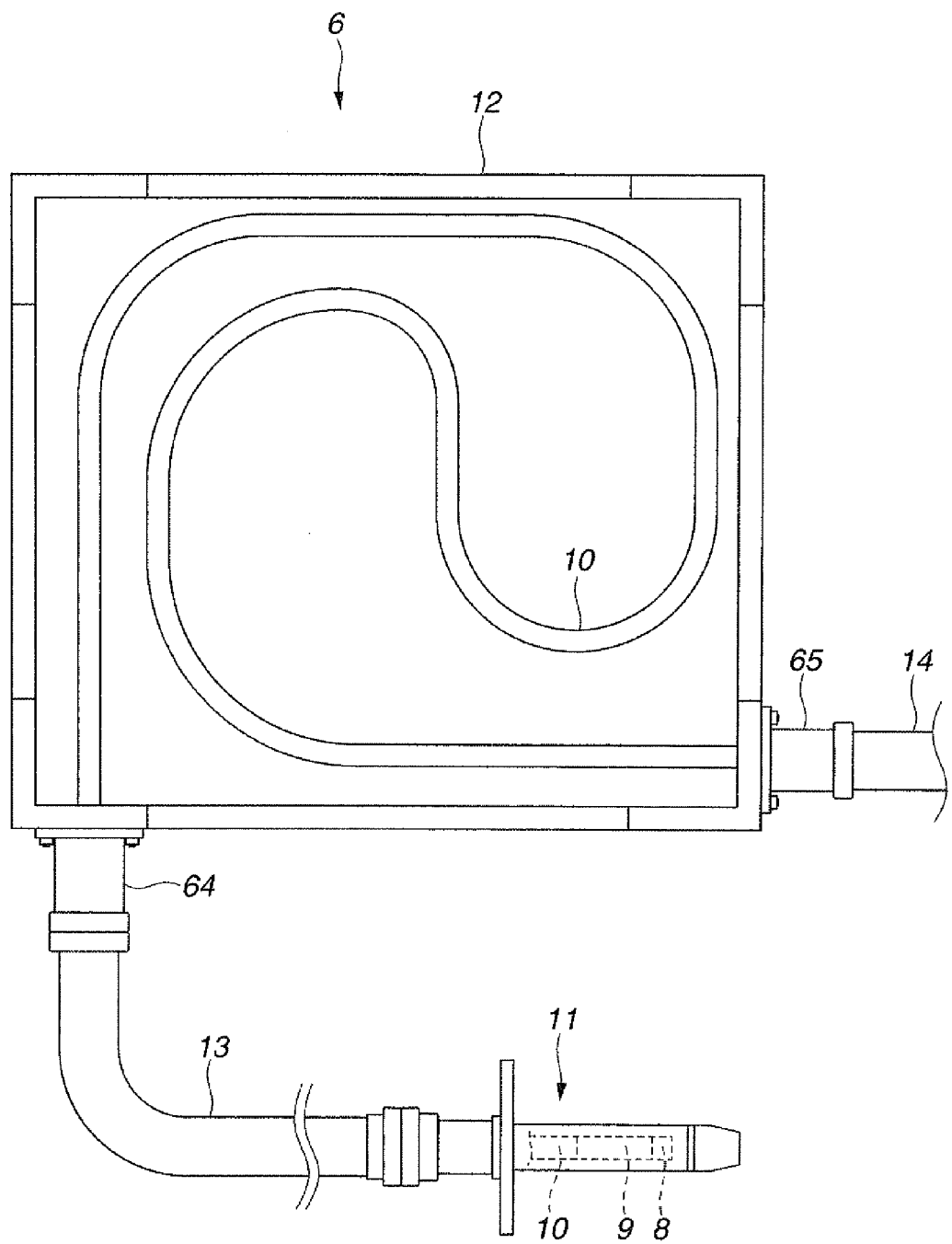
FIG. 107 is a plan view of the housing case viewed from an upper surface thereof according to the embodiment.
Figure 108:
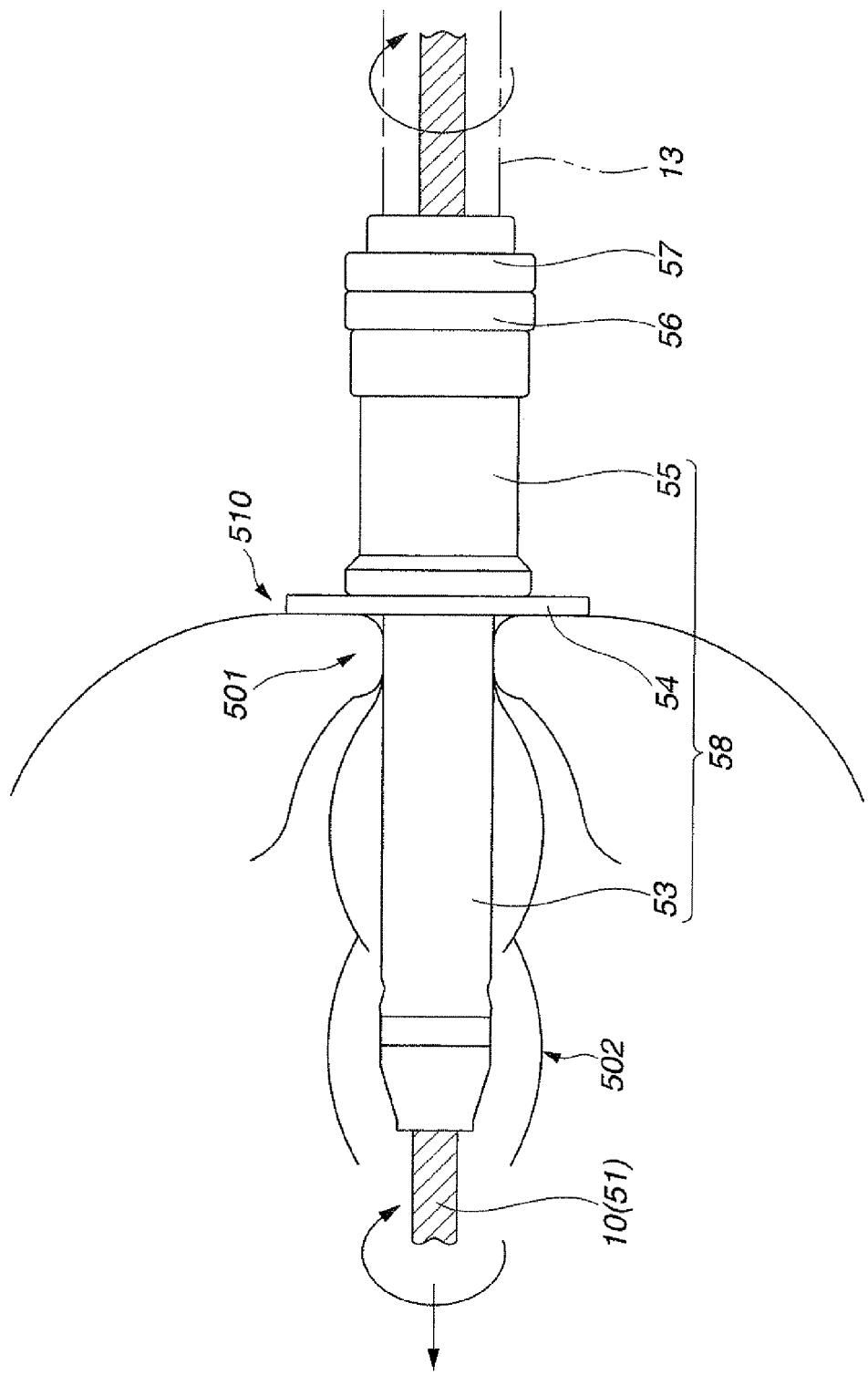
FIG. 108 is a diagram for action explanation showing a state in which the insertion assisting tool is inserted into the intestinum rectum from the anus of a patient according to the embodiment.
Figure 109:
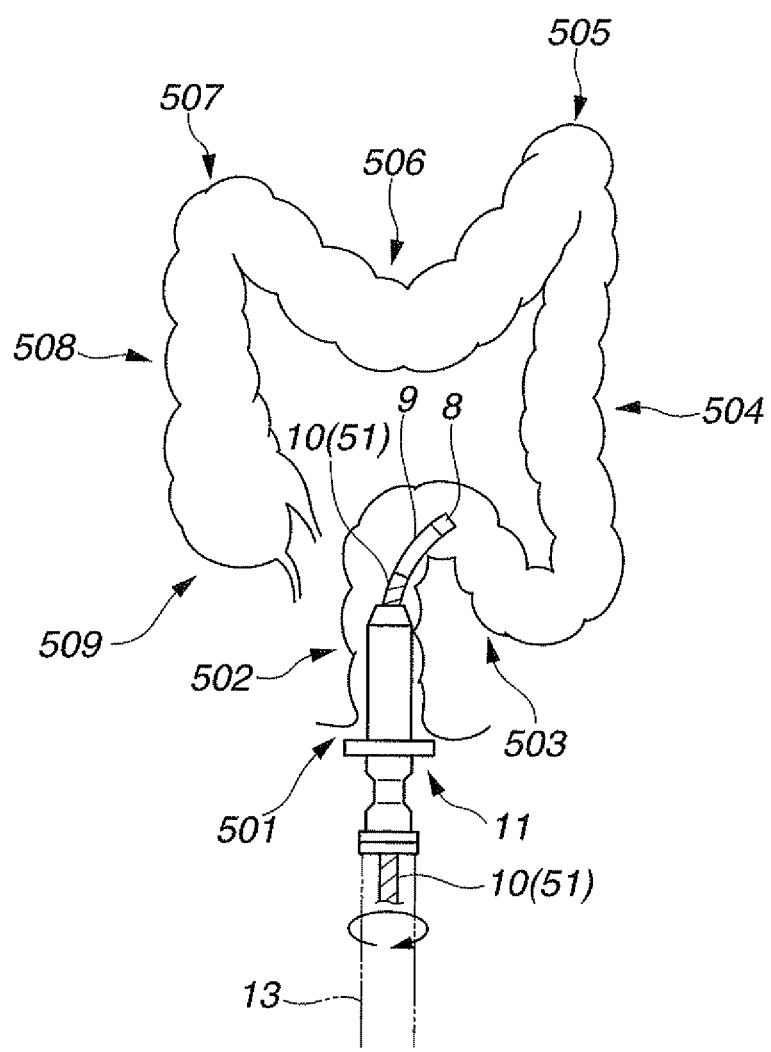
FIG. 109 is a diagram for action explanation showing a state in which the insertion portion main body inserted in the large intestine reaches the sigmoid colon according to the embodiment.
Figure 110:
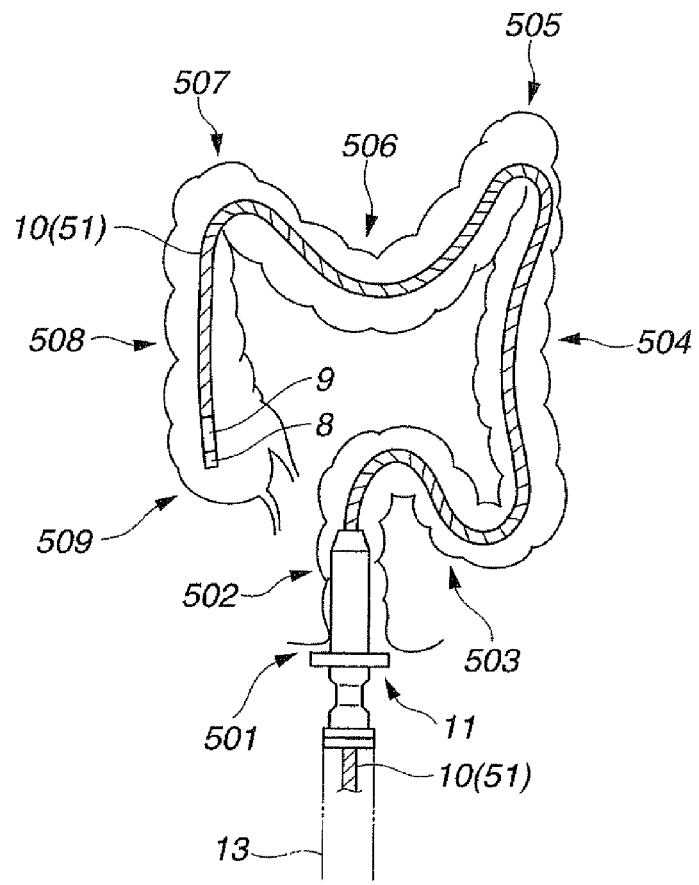
FIG. 110 is a diagram for action explanation showing a state in which the insertion portion main body inserted in the large intestine reaches in the vicinity of the cecum according to the embodiment.
Figure 111:
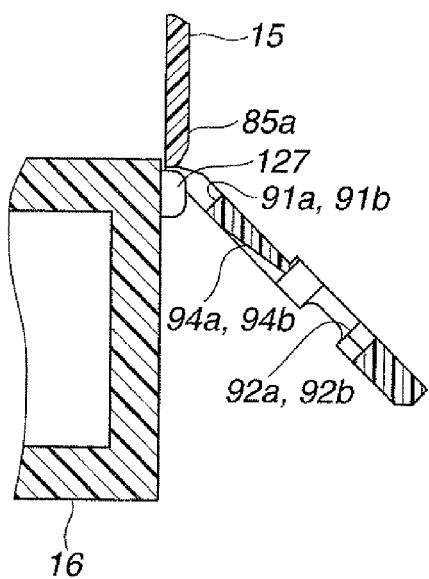
FIG. 111 is a diagram for explaining an operation in disengaging the connector cover from the motor box according to the embodiment.
Figure 112:
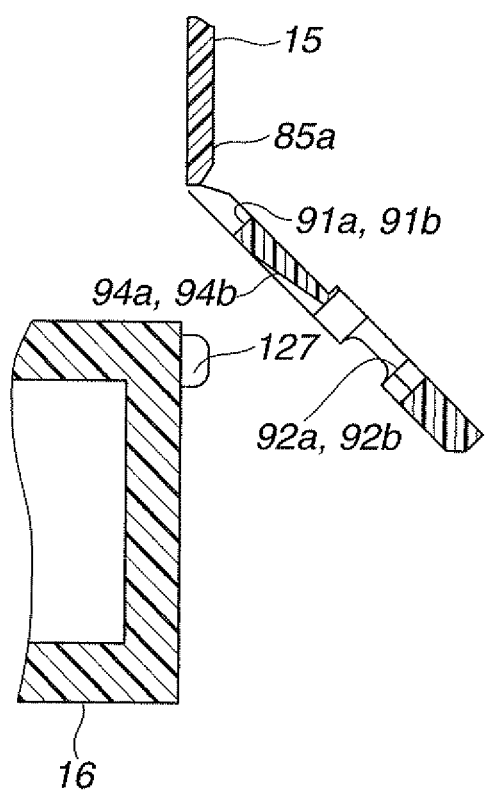
FIG. 112 is a diagram for explaining the operation in disengaging the connector cover from the motor box according to the embodiment.

FIGS. 1 to 112 relate to an embodiment of the present invention. FIG. 1 is an overall diagram of a rotary self-propelled endoscope system. FIG. 2 is a sectional view showing a distal end portion, a bending portion, and a part of a rotating cylinder of the endoscope. FIG. 3 is a perspective view showing an insertion assisting tool. FIG. 4 is a disassembled perspective view of the insertion assisting tool to which a guide tube is connected. FIG. 5 is a sectional view of the insertion assisting tool with the guide tube connected thereto. FIG. 6 is a sectional view showing a proximal end portion of the insertion assisting tool with the guide tube connected thereto. FIG. 7 is a sectional view of the insertion assisting tool along VII-VII line in FIG. 6. FIG. 8 is a disassembled perspective view of a housing case. FIG. 9 is a sectional view of the housing case. FIG. 10 is a plan view of the housing case viewed from one side. FIG. 11 is an enlarged view showing one side of the housing case to which a guide tube fixing member is attached. FIG. 12 is an enlarged plan view showing a state in which the guide tube fixing member is attached to one side of the housing case shown in FIG. 11. FIG. 13 is a disassembled perspective view of the guide tube fixing member in which a thrust generating member is disposed. FIG. 14 is a partial sectional view of the guide tube fixing member in which the thrust generating member is disposed viewed from an up to down direction of the housing case. FIG. 15 is a partial sectional view of the guide tube fixing member in which the thrust generating member is disposed viewed from a left to right direction of the housing case. FIG. 16 is a plan view showing the thrust generating member. FIG. 17 is a sectional view for explaining an action of the thrust generating member in the guide tube fixing member through which the rotating cylinder is inserted. FIG. 18 is a partial sectional view of the guide tube fixing member on the operation portion side. FIG. 19 is a sectional view showing a state of connection between an operation portion side guide tube and a connector cover. FIG. 20 is a sectional view showing a part of the connector cover to which the operation portion side guide tube is connected. FIG. 21 is a plan view of a connector box showing a section along XXI-XXI line in FIG. 20. FIG. 22 is a sectional view showing a state in which the rotating cylinder of an insertion portion main body is inserted through the guide tube. FIG. 23 is a sectional view of the rotating cylinder of the insertion portion main body in the housing case viewed from one side. FIG. 24 is a plan view of the connector cover viewed from a surface on an opening side. FIG. 25 is a sectional view of the connector cover along XXV-XXV line in FIG. 24. FIG. 26 is a sectional view of the connector cover along XXVI-XXVI line in FIG. 25. FIG. 27 is a plan view of a connector main body of the connector cover viewed from a proximal end side. FIG. 28 is a diagram for explaining a locking convex portion in an enlarged circle XXVIII in FIG. 27. FIG. 29 is a disassembled perspective view for explaining an insertion portion side gear, a rotating shaft, a bearing, and an elastic member disposed in the connector main body. FIG. 30 is a diagram for explaining an electric connector and the elastic member. FIG. 31 is a diagram for explaining a content holding body and the elastic member. FIG. 32 is a perspective view of an assembled connector main body with a rear side thereof set upward. FIG. 33 is a plan view showing an upper surface of a wire connection plate. FIG. 34 is a plan view showing a rear surface of the wire connection plate. FIG. 35 is a sectional view of the wire connection plate along XXXV-XXXV line in FIGS. 33 and 34. FIG. 36 is a side view of the wire connection plate. FIG. 37 is a plan view of the wire connection plate viewed from a proximal end side thereof. FIG. 38 is a plan view of the wire connection plate viewed from a distal end side thereof. FIG. 39 is a perspective view of a wire anchor connected to a bending operation wire. FIG. 40 is a plan view of the wire anchor viewed from a distal end side thereof. FIG. 41 is a partial sectional view showing a side of the wire anchor. FIG. 42 is a plan view of the wire anchor viewed from a proximal end side thereof. FIG. 43 is a diagram for explaining a state in which the wire anchor is disposed on the wire connection plate. FIG. 44 is a plan view of the wire connection plate having the wire anchor disposed thereon viewed from a proximal end direction of the wire connection plate. FIG. 45 is a diagram showing a state in which the wire connection plate is attached to the connector main body. FIG. 46 is a diagram for explaining a state in which the wire connection plate is moved with respect to the connector main body. FIG. 47 is a top view of the connector cover. FIG. 48 is a rear view of the connector cover. FIG. 49 is a sectional view of the connector cover along 4XIX-4XIX line in FIG. 48. FIG. 50 is a sectional view of the connector cover along 5X-5X line in FIG. 49. FIG. 51 is a top view showing the operation portion. FIG. 52 is a plan view showing a rear surface of a main operation portion. FIG. 53 is a top view showing a motor box. FIG. 54 is a sectional view of the motor box. FIG. 55 is a perspective view showing an electric connector on a female side. FIG. 56 is a sectional view in a lateral direction of the electric connector. FIG. 57 is a sectional view in a longitudinal direction of the electric connector. FIG. 58 is a perspective view showing a motor cover. FIG. 59 is a sectional view for explaining an engaging hole of the motor cover. FIG. 60 is a diagram showing the internal structure of a grasping portion and the main operation portion. FIG. 61 is a sectional view of the grasping portion along 6XI-6XI line in FIG. 60. FIG. 62 is a sectional view of the grasping portion along 6XII-6XII line in FIG. 60. FIG. 63 is a diagram showing the internal structure of the grasping portion and the main operation portion. FIG. 64 is a perspective view showing a coupling member. FIG. 65 is a perspective view showing a stopper. FIGS. 66 and 67 are diagrams for explaining a state in which the coupling member comes into contact with the stopper. FIG. 68 is a perspective view showing a first guide plate. FIG. 69 is a perspective view showing a second guide plate. FIG. 70 is a perspective view showing a state before the connector cover docks with the motor box. FIG. 71 is a perspective view showing a state in which the connector cover docks with the motor box. FIG. 72 is a sectional view showing the state before the connector cover docks with the motor box. FIG. 73 is a sectional view showing the state in which the connector cover docks with the motor box. FIG. 74 is a top view showing the state before the connector cover docks with the motor box. FIG. 75 is a side view showing the state before the connector cover docks with the motor box. FIG. 76 is a partial sectional view showing a state in which the wire connection plate is guided by a guide plate. FIG. 77 is a diagram for explaining a state in which an engaging convex portion of the motor box is guided by a linear groove of the connector cover. FIG. 78 is a side view showing a state immediately before the connector cover docks with the motor box. FIGS. 79 to 81 are diagrams for explaining a state in which the wire connection plate is guided by a second guide plate. FIGS. 82 to 85 are diagrams for explaining a state in which the wire anchor of the wire connection plate is inserted in an anchor locking hole of the coupling member. FIG. 86 is a side view showing a state in which the connector cover docks with the motor box. FIGS. 87 to 90 are diagrams for explaining a state in which the engaging convex portion of the motor box is inserted in an engaging hole while being guided by a guide groove of the connector cover and an inclined surface. FIG. 91 is an enlarged plan view showing a state in which the engaging convex portion is inserted in the engaging hole. FIGS. 92 to 94 are diagrams for explaining a state in which an engaging leg portion of the bearing is inserted in the engaging hole of the motor cover. FIGS. 95 and 96 are diagrams for explaining a state in which the engaging leg portion of the bearing is inserted in the engaging hole of the motor cover and an insertion portion side gear and a motor gear mesh with each other FIGS. 97 and 98 are diagrams for explaining an action of an elastic member fastened to the bearing. FIGS. 99 to 101 are diagrams for explaining an action in the meshing of the insertion portion side gear and the motor gear. FIGS. 102 to 105 are diagrams for explaining actions of a projecting portion of an electric connector on a male side and the fastened elastic member in connection of the electric connector on the male side and the electric connector on the female side. FIG. 106 is a top view showing a state in which the connector cover docks with the motor box according to the embodiment. FIG. 107 is a plan view of the housing case viewed from an upper surface thereof. FIG. 108 is a diagram for action explanation showing a state in which the insertion assisting tool is inserted into the intestinum rectum from the anus of a patient. FIG. 109 is a diagram for action explanation showing a state in which the insertion portion main body inserted in the large intestine reaches the sigmoid colon. FIG. 110 is a diagram for action explanation showing a state in which the insertion portion main body inserted in the large intestine reaches in the vicinity of the cecum. FIGS. 111 and 112 are diagrams for explaining an operation in disengaging the connector cover from the motor box.

First, an overall configuration of a rotary self-propelled endoscope system 1 is explained on the basis of FIG. 1.

As shown in FIG. 1, the rotary self-propelled endoscope system (hereinafter abbreviated as endoscope system) 1 mainly includes a rotary self-propelled endoscope (hereinafter simply abbreviated as endoscope) 2, a control device 3, a monitor 4, and an aspirator 5.

The endoscope 2 mainly includes an endoscope insertion portion with housing case 6 and an operation portion 7.

The endoscope insertion portion with housing case 6 mainly includes, in order from a distal end thereof, a distal end rigid portion (hereinafter simply abbreviated as distal end portion) 8, a bending portion 9, an insertion portion main body 10, a rotating cylinder 51, an insertion assisting tool 11, an insertion portion housing case main body (hereinafter abbreviated as housing case main body) 12, a distal end side guide tube 13 as a corrugated tube interposed between the insertion assisting tool 11 and the housing case main body 12, an operation portion side guide tube 14 as a corrugated tube interposed between the operation portion 7 and the housing case main body 12, and a connector cover 15 to which one end of the operation portion side guide tube 14 is coupled.

The operation portion 7 mainly includes a motor box 16 as rotating means to which a connector cover 15 configuring a part of the endoscope insertion portion with housing case 6 is detachably attachable, a grasping portion 17, and a main operation portion 18. A coupling portion of the endoscope 2 according to the present embodiment is configured by the connector cover 15 and the motor box 16. A first functional connection, a second functional connection, and a third functional connection described later for enabling respective functions of the endoscope 2 are performed by coupling (docking) of the connector cover 15 and the motor box 16.

In the main operation portion 18, a bending operation knob 19 as an operation lever that bends the bending portion 9 of the endoscope insertion portion with housing case 6 in four directions (up, down, left, and right directions corresponding to an endoscopic image taken by the endoscope 2), buttons 20 for subjecting fluid to feeding operation or aspiration operation, and switches 21 for operating devices such as various optical systems for image pickup, illumination, and the like and a printer are disposed.

The bending operation knob 19 is disposed on one surface of the main operation portion 18 of the operation portion 7 such that substantially disc-shaped two knobs are superimposed. The two knobs are rotatably disposed and include an U(UP)/D(DOWN) bending operation knob 19a, which is provided on the main operation portion 18 side, for operating the up to down direction of the bending portion 9 and an R(RIGHT)/L(LEFT) bending operation knob 19b, which is provided on the U/D bending operation knob 19a, for operating the left to right direction of the bending portion 9.

A universal cord 18a as an electric cable is extended from one side of the main operation portion 18. In the main operation portion 18, a bend preventing portion 18b is provided in a root portion from which the universal cord 18a is extended.

A connector portion 22 is disposed at an extending end of the universal cord 18a. The connector portion 22 is connected to the control device 3.

The buttons 20 disposed on one side of the main operation portion 18 include an air feed/water feed button 20a operated when the gas or liquid is fed from the distal end portion 8 of the endoscope 2 into a subject and an aspiration button 20b operated when liquid such as soil in the subject is aspirated from the distal end portion 8 of the endoscope 2.

Three tubes 23 inserted through the endoscope insertion portion with housing case 6 are extended out from the connector cover 15 attached to and detached from the motor box 16. The three tubes 23 include an air feed tube 23a, a water feed tube 23b, and an aspiration tube 23c. Extend-out ends of the three tubes 23 are connected in a predetermined position on a front portion of the control device 3 via detachably attachable connectors, respectively.

A water feed tank 24 is provided in the control device 3. Distilled water or physiological saline is stored in the water feed tank 24. When the air feed/water feed button 20a of the main operation portion 18 is subjected to predetermined operation, the distilled water or the physiological saline is fed to the water feed tube 23b by the control device 3 and blows out from the distal end portion 8 of the endoscope 2. When the air feed/water feed button 20a of the main operation portion 18 is subjected to predetermined operation, the air is fed to the air feed tube 23a from a not-shown compressor in the control device 3. The air blows out from the distal end portion 8 of the endoscope 2.

When the aspiration button 20b is operated, soil and the like are aspirated from the distal end portion 8 of the endoscope 2. The soil and the like are fed from the control device 3 into the aspirator 5 via the aspiration tube 23c. In the rotary self-propelled endoscope system 1 according to the present embodiment, the aspirator 5 is used. However, an aspiration system provided in a hospital may be used.

A foot switch 25 is connected to the control device 3 via an electric cable 25a. The foot switch 25 is a switch for rotating the insertion portion main body 10 of the endoscope 2 in a predetermined direction and stops the insertion portion main body 10. An advancing and retracting switch for operating the insertion portion main body 10 in a rotating direction and stopping the insertion portion main body 10 is also disposed in the main operation portion 18 of the operation portion 7 described later, although not shown in the figure.

A power supply switch, a dial for changing rotation speed of the insertion portion of the endoscope 2, and the like are disposed in the front portion of the control device 3. A not-shown motor that gives torque to the insertion portion is built in the motor box 16 of the operation portion 7.

The control device 3 is electrically connected to the monitor 4. The monitor 4 displays an endoscopic image captured by the endoscope 2.

Next, the distal end portion 8, the bending portion 9, the insertion portion main body 10, and the rotating cylinder 51 configuring the insertion portion of the endoscope 2 are explained with reference to FIG. 2.

First, the distal end portion 8 is explained.

The distal end portion 8 mainly includes a rigid substantially annular main body ring 26 including synthetic resin having biocompatibility and an image pickup unit 27.

An external shape of the image pickup unit 27 is formed by a substantially annular holding ring 28a including synthetic resin housed in the main body ring 26, a substantially annular cover ring 28b including metal fit on a proximal end side of the holding ring 28a, and a cover body 29 fit to hermetically seal a distal end opening of the holding ring 28a and formed in a dome shape by transparent synthetic resin having biocompatibility.

In a space of the image pickup unit 27 formed by the members, an object lens group 30, an image pickup device 31 such as a CCD or a CMOS arranged in a position where photographing light made incident on the object lens group 30 is condensed, and a flexible printed board (FPC) 32 to which an image signal photoelectrically converted by the image pickup device 31 is inputted are disposed.

A communication cable 33 is connected to the FPC 32. The communication cable 33 is inserted through the bending portion 9 and the insertion portion main body 10 and connected to a not-shown connector disposed in the connector cover 15 (see FIG. 1).

In a plate body 35 that fixes a holding ring for holding the object lens group 30, plural LEDs 34 as illuminating members are disposed to surround the object lens group 30. The plate body 35 is formed in a substantially circular shape such that the plate body 35 can adhere to an inner surface on an extended line in a portion passing through the substantially center of the cover body 29. The object lens group 30 is arranged such that an optical axis passes substantially the center position on a plate surface of the plate body 35.

The image pickup unit 27 thus configured is arranged in a position eccentric with respect to the center of the main body ring 26 and fixed to the main body ring 26 by a distal end cap 36 disposed in a distal end side opening of the main body ring 26.

In a space formed between the holding ring 28a of the image pickup unit 27 and the main body ring 26, a distal end portion of the aspiration tube 23c and an aspiration tube 37, to a proximal end side of which the aspiration tube 23c is connected, are arranged. A distal end portion of the aspiration tube 37 is fastened to the distal end cap 36.

An opening 38 for aspiration is formed in the distal end cap 36. Although not shown in the figure, conduit lines communicating with the air feed tube 23a and the water feed tube 23b are disposed by using the space formed between the holding ring 28a and the main body ring 26. Openings of those conduit lines are also formed in the distal end cap 36.

Next, the bending portion 9 is explained.

In the bending portion 9, a rigid distal end bending piece 39 fit in the proximal end opening of the main body ring 26 of the distal end portion 8 and rigid plural bending pieces 40 (also referred to as bending node ring) are continuously provided to be freely rotated by a pivotably supporting portion 40a. The pieces 39 and 40 are coated with a bending skin 41 including an elastic member such as fluororubber having biocompatibility. A distal end portion of the bending skin 41 is fastened to the proximal end portion of the main body ring 26 of the distal end portion 8 by a bobbin bonding portion 42.

The plural bending pieces 40 have a wire guide that projects in a center direction from an inner peripheral surface thereof. Bending operation wires 44 (also referred to as angle wires) are inserted through the wire guide 43.

There are four distal end portions of the bending operation wires 44 in the bending portion 9 (only two are shown in FIG. 2). Cylindrical locking members 45 are welded to the distal end portions by soldering or the like, respectively. The locking members 45 of the bending operation wires 44 are fastened to four locking holes 39a formed in the distal end bending piece 39, respectively.

The four locking holes 39a are formed in equally divided four positions at substantially equal intervals on a surface orthogonal to an axis of the distal end bending piece 39. A direction around the axis of the distal end bending piece 39 is determined such that the respective locking holes 39a are located in association with the up, down, left, and right directions of the endoscopic image. Therefore, the four bending operation wires 44 are held and fixed at four points spaced apart at substantially equal intervals in the up, down, left, and right directions.

The bending operation wires 44 are inserted through the insertion portion main body 10 and disposed to the connector cover 15. In respective proximal end portions of the bending operation wires 44, not-shown wire anchors described later are provided. The wire anchors of the respective bending operation wires 44 are coupled to not-shown coupling members, which are bending wire locking members, described later provided in the grasping portion 17 in a state in which the connector cover 15 is integral with the motor box 16.

The respective coupling members are coupled to a not-shown bending operation mechanism described later, which operates in association with the bending operation knob 19 disposed in the main operation portion 18, by a not-shown chain described later. In other words, when the bending operation knob 19 is rotated, the respective coupling members are alternately tugged or loosened by the bending operation mechanism. The respective bending operation wires 44 are alternately tugged or loosened in association of the movement of the coupling members.

Therefore, when the four bending operation wires 44 are tugged or loosened back and forth, respectively, the plural bending pieces 40 rotate in association with the movement of the bending operation wires 44. Thus, the bending portion 9 is bent in the four directions.

In the proximal end portion of the bending portion 9, a first mouthpiece 46 including metal for coil pipe fixing fit in the bending piece 40 provided at a most proximal end, a second mouthpiece 47 including metal for inner layer tube fixing fit on an outer peripheral side of the bending piece 40 provided at the most proximal end, and a third mouthpiece 48 including synthetic resin for rotatably engaging a rotating cylinder fit on an outer peripheral side of the second mouthpiece 47 are disposed. The mouthpieces 46 to 48 are firmly fastened by an adhesive or the like.

The bending skin 41 is also fastened with the third mouthpiece 48 by the bobbin bonding portion 42.

Proximal end sides of the bending operation wires 44 are inserted through coil sheaths 49 from the first mouthpiece 46, respectively. Distal end portions of the coil sheaths 49 are inserted and fixed in a hole formed in the first mouthpiece 46. The coil sheaths 49 used in the present embodiment has an incompressible configuration formed by closely attaching and winding a wire.

A distal end portion of a flexible inner layer tube 49a inserted through the insertion portion is fixed to a proximal end portion of the second mouthpiece 47. The inner layer tube 49a may be a tube body imparted with flexibility by knitting a thin wire or the like in a cylindrical shape.

A projecting portion 48a is provided in a proximal end portion of the third mouthpiece 48. The third mouthpiece 48 is completely covered with the bending skin 41 such that a space can be formed on an outer peripheral side of the projecting portion 48a. Actions of the projecting portion 48a are explained later.

Next, the insertion portion main body 10 is explained.

The insertion portion main body 10 mainly includes, in a distal end portion thereof, a mouthpiece 50 including synthetic resin for coupling, and a rotating cylinder 51 as a spiral tube forming a skin, a distal end portion of which is fastened to the mouthpiece 50 by an adhesive 52.

In the insertion portion main body 10, the inner layer tube 49a, the four coil sheaths 49 through which the bending operation wires 44 are inserted, respectively, the communication cable 33, and the not-shown various tubes 23 are disposed. In other words, as is seen from the figure, the inner layer tube 49a is provided on an outermost side and protects the respective components in the inside.

The mouthpiece 50 including synthetic resin for coupling is fastened to a distal end portion of the rotating cylinder 51. The distal end portion is fastened by the adhesive 52.

In the mouthpiece 50, a convexo-concave portion 50a that engages with the projecting portion 48a of the third mouthpiece 48 of the bending portion 9 is formed in a distal end portion thereof. In other words, the mouthpiece 50 and the third mouthpiece 48 are rotatable around axes thereof. In other words, the rotating cylinder 51 externally fit in the insertion portion main body 10 rotates around an axis of the inner layer tube 49a thereof as described later and the insertion portion main body 10 itself does not rotate.

The rotating cylinder 51 coupled to the mouthpiece 50 is a cylinder having flexibility formed by spirally winding a metal plate body having biocompatibility processed to have an irregular sectional shape. In the rotating cylinder 51, concaves and convexes are engaged without a gap. A spiral shape portion 51a as a spiral convex portion (or a spiral concave portion, a convex portion projected to be continuously provided along a spiral, etc.) is formed on an outer peripheral surface thereof.

Specifically, the rotating cylinder 51 is a spiral tube formed by taking into account insertability into the body cavity and made of stainless steel, for example. A predetermined diameter dimension thereof is set. In the rotating cylinder 51, a pitch of the concaves and the convexes, an angle of the spiral, and the like can be set in various ways by changing the dimension of concaves and convexes formed in a plate body. The width of the convex portions forming the spiral shape portion 51a is set larger than the width of the concave portions. Consequently, even if the rotating cylinder 51 forming the outer shape of the insertion portion overlaps in a bent state, the convex portions are prevented from entering the concave portions.

The rotating cylinder 51 is configured to be rotatable around an axis in an insertion direction. When the rotating cylinder 51 rotates, the spiral shape portion 51a on the outer peripheral surface comes into contact with a body cavity inner wall of the subject, thrust is generated, and the rotating cylinder 51 itself is about to advance in the insertion direction.

At the point, the mouthpiece 50 fastened to the distal end portion of the rotating cylinder 51 comes into contact with the third mouthpiece 48 present in the proximal end portion of the bending portion 9 to press the bending portion 9. Thrust for advancing the entire insertion portion including the distal end portion 8 toward the depth of the body cavity is given.

Torque is given to the rotating cylinder 51 by a motor (not shown) configuring a part of rotating means disposed in the motor box 16 (see FIG. 1) of the operation portion 7. In the present embodiment, the insertion portion of the rotary self-propelled endoscope 2 is configured by the distal end portion 8, the bending portion 9, the insertion portion main body 10, and the rotating cylinder 51.

Next, the insertion assisting tool 11 is explained with reference to FIGS. 3 to 7.

As shown in FIG. 3, the insertion assisting tool 11 mainly includes an insertion tube 53, an aberration preventing portion 54 as aberration preventing means, a holding tube 55, a first fixing ring 56, and a second fixing ring 57.

The insertion tube 53, the aberration preventing portion 54, and the holding tube 55 are integrated to configure a tube main body 58 in the insertion assisting tool 11.

The holding tube 55 is a substantially cylindrical metal ring having a shape projecting in an outer diameter direction in both end outer peripheral portions thereof. The holding tube 55 is not limited to a metal cylinder and may be a rigid cylinder including synthetic resin or plastic. In the holding tube 55, as shown in FIG. 4, a female screw portion 55a is formed in an inner peripheral surface on a proximal end side.

The first fixing ring 56 is a substantially cylindrical metal ring having a shape projecting in the outer diameter direction in a proximal end outer peripheral portion thereof. The first fixing ring 56 is not limited to a metal cylinder and may be a rigid cylinder including synthetic resin or plastic. A male screw portion 56a is formed in an outpour peripheral surface side and a female screw portion 56b is formed on an inner peripheral surface side in a proximal end portion of the first fixing ring 56.

The second fixing ring 57 is a substantially cylindrical metal ring having a shape projecting in the outer diameter direction in a halfway outer peripheral portion thereof. The second fixing ring 57 is not limited to a metal cylinder and may be a rigid cylinder including synthetic resin or plastic. A male screw portion 57a is formed on an outer peripheral surface side in a distal end portion of the second fixing ring 57.

The distal end side guide tube 13 is inserted in the second fixing ring 57. The distal end side guide tube 13 is inserted to project on the distal end side of the second fixing ring 57. A holding ring 59 separated into two is fit in from an outer peripheral direction of the projecting distal end portion. Detailed explanation concerning the distal end side guide tube 13 and detailed explanation concerning the fixing to the insertion assisting tool 11 by the holding ring 59 are made later.

As shown in FIG. 5, the insertion tube 53 includes a distal end insertion tube 53a of a substantially annular shape including synthetic resin having flexibility such as silicon, on an outer periphery of which a taper surface is formed to be tapered, an insertion cylinder 53b forming a main body, and a connecting ring 53c that couples the distal end insertion tube 53a and the insertion cylinder 53b on an inner peripheral side.

The insertion cylinder 53b includes, in order from an outer surface side, an outer tube 53d formed of synthetic resin such as polyurethane, a blade 53e formed in a cylindrical shape by knitting a metal wire in a mesh shape, a flex tube 53f as a metallic spiral tube, and an inner tube 53g formed of synthetic resin such as polyurethane.

The outer tube 53d, the blade 53e, the flex tube 53f, and the inner tube 53g are formed in a four-layer structure and fastened such that the members corresponding to each other are integral by bonding, welding, or the like, respectively. Consequently, the insertion cylinder 53b is formed as a tube body having flexibility for which predetermined rigidity is set.

The insertion cylinder 53b may be formed as a cylinder including a single member when the predetermined rigidity and predetermined flexibility are sufficiently obtained. Moreover, coating such as Teflon (registered trademark) treatment for improving smoothness may be applied to an outer peripheral surface and an inner peripheral surface thereof. The aberration preventing portion 54, which is a hollow disc including synthetic resin such as silicon, is disposed in a proximal end portion of the insertion cylinder 53b.

A hole diameter of the aberration preventing portion 54 is set smaller than an outer shape of the insertion cylinder 54b. The aberration preventing portion 54 is fastened and fixed to the insertion cylinder 53b with predetermined holding intensity by elastic deformation thereof. Consequently, it is possible to set desired insertion length into the body cavity from a distal end to a proximal end of the insertion tube 53 by changing a position of the aberration preventing portion 54.

The proximal end portion of the insertion cylinder 53b has, as shown in FIG. 5, three-layer structure including the blade 53e, the flex tube 53f and the inner tube 53g and is fastened to an annular mouthpiece 60 by bonding or the like. The holding tube 55 is screwed to the mouthpiece 60, which is the proximal end of the insertion cylinder 53b of the insertion tube 53.

The tube main body 58 has an opening 58a, which is a distal end opening of the distal end insertion tube 53a, at a distal end thereof. The opening 58a forms an opening in the insertion assisting tool 11 through which the insertion portion projects.

The male screw portion 56a of the first fixing ring 56 is screwed to the female screw portion 55a of the holding tube 55, which is the proximal end of the tube main body 58, whereby the first fixing ring 56 is fixed to the holding tube 55.

The holding ring 59, through which the distal end side guide tube 13 is inserted, is fit in the first fixing ring 56. The second fixing ring 57 is fixed to the first fixing ring 56. In other words, the female screw portion 56b of the first fixing ring 56 and the male screw portion 57a of the second fixing ring 57 are screwed, whereby the second fixing ring 57 is fixed to the first fixing ring 56.

At the point, both end faces of the holding ring 59 are fit and fixed by an end face in the first fixing ring 56 and an end face in the second fixing ring opposed thereto, respectively. In the holding ring 59, inward flanges 59a and 59b are formed around an axis toward an inner peripheral direction in the center and the proximal end portion of the inner peripheral surface of the holding ring 59.

As shown in FIGS. 6 and 7, the inward flanges 59a and 59b lock the corrugated concaves and convexes of the distal end side guide tube 13. Consequently, the distal end side guide tube 13 is connected to the insertion assisting tool 11. In the distal end portion of the distal end side guide tube 13, i.e., a portion indicated by reference sign F in FIG. 6, the distal end side guide tube 13 comes into a state in which the distal end side guide tube 13 is compressed against a surface on a proximal end side of a step formed in the first fixing ring 56, whereby the distal end side guide tube 13 is connected to the insertion assisting tool 11 while keeping water-tightness. In other words, a conduit line having the opening 58a of the tube main body 58 as a distal end opening is formed by the insertion assisting tool 11 and the distal end guide tube 13.

Next, the housing case main body 12 is explained with reference to FIGS. 8 to 12.

As shown in FIG. 8, the housing case main body 12 mainly includes transparent or semitransparent rectangular two plate bodies 61 and 62 having light transmission properties such as acrylic plates, plural frame bodies 63a for fastening one surfaces of the respective two plate bodies 61 and 62 to be opposed to each other with a predetermined distance apart from each other, and two guide tube fixing members 64 and 65.

By adopting colored plates that is semitransparent or has light transmission properties as the plate bodies 61 and 62, it is possible to make soil adhering to the rotating cylinder 51 less conspicuous and allow the user to visually recognize the rotation of the rotating cylinder 51.

In the two plate bodies 61 and 62, L-shaped leg portions 66 are fixed at corners of surfaces on the opposite side of surfaces opposed to each other. The leg portions 66 are fastened to the respective surfaces of the plate bodies 61 and 62 by bonding or the like to match any one of the four corners of the respective plate bodies 61 and 62.

In the plate bodies 61 and 62, frame bodies 63a to 63f having equal dimensions in the thickness direction are fastened, by bonding or the like, on respective edge portions of the surfaces on the opposite side of the surfaces on which the leg portions 66 are fixed. In other words, as described above, the two plate bodies 61 and 62 are fixed such that the respective plate surfaces are parallel at a distance apart from each other by the thickness of the respective frame bodies 63a to 63f.

The frame bodies 63a to 63f have a substantially square pole shape set to predetermined lengths, respectively. As shown in FIG. 9, the frame bodies 63a to 63f are provided in the four directions on edge portions along the four sides of the plate bodies 61 and 62. In other words, in the housing case main body 12, an inner space is formed by the two plate bodies 61 and 62 and the respective frame bodies 63a to 63f.

Spaces 68 predetermined intervals apart from one another are formed between one end of the frame body 63a and one end of the frame body 63b and between one end of the frame body 63c and one end of the frame body 63d such that the insertion portion can be inserted through the spaces. At corners on the inner side of the frame bodies 63a to 63d forming the spaces 68, smooth curved surfaces 69 are formed to allow the insertion portion to pass smoothly.

The respective guide tube fixing members 64 and 65 are fixed to one side of the housing case main body 12 by fixing members 67 including bolts and nuts to lay over the frame bodies 63a and 63b or the frame bodies 63c and 63d in positions matching the spaces 68.

Specifically, as shown in FIG. 10, the respective guide tube fixing members 64 and 65 have a shape in which rectangular plate members 64b and 65b made of metal are fixed to one ends of cylinders 64a and 65a. The respective guide tube fixing members 64 and 65 are not limited to metal members and may be rigid cylinders including synthetic resin, plastic, or the like.

The guide tube fixing members 64 and 65 are fixed as shown in FIGS. 10 and 12 by the fixing members 67 inserted through the holes 67a (in FIG. 1, only the screw holes 67a of the frame bodies 63a and 63b are shown) formed in the respective frame bodies 63a to 63d.

The respective guide tube fixing members 64 and 65 are fixed, with the centers of the respective spaces 68 thereof matched with the holes of the cylinders 64a and 65a, to communicate with the inner space of the housing case main body 12. Arrangement positions of the spaces 68 and the respective guide tube fixing members 64 and 65 are set on sides in the vicinity of the corners of the housing case main body 12 such that longitudinal axes of the cylinders 64a and 65 of the respective guide tube fixing members 64 and 65 are orthogonal to the spaces 68 and the respective guide tube fixing members 64 and 65. Moreover, the respective guide tube fixing members 64 and 65 are set not to be arranged in the vicinity of the identical corners of the housing case 12.

In other words, as shown in FIG. 9, when the guide tube fixing member (hereinafter referred to as first guide tube fixing member as well) 64 is fixed in the vicinity of the corner on the lower left in the side facing downward of the housing case main body 12 viewed on the paper surface, the guide tube fixing portion (hereinafter referred to as second guide tube fixing member as well) 65 is fixed in the vicinity of the corner on the lower right on the side facing the left direction of the housing case main body 12 viewed on the paper surface.

Rubber plates 76 (see FIGS. 14, 15, and 17) for keeping water-tightness are interposed between the respective plate members 64b and 65b of the respective guide tube fixing members 64 and 65 and the respective frame bodies 63a and 63d.

The other side of the distal end side guide tube 13, one end of which is connected to the insertion assisting tool 11, is connected to the first guide tube fixing member 64.

Specifically, as shown in FIG. 13, a female screw portion 64c is formed on an inner peripheral surface on a proximal end side of the cylinder 64a of the first guide tube fixing member 64, which is a coupling portion for coupling the housing case main body 12 and the distal end side guide tube 13. In the cylinder 64a, a first thrust generating member 70a, a first pressing ring 72, a second thrust generating member 70b, and a second pressing ring 73 are arranged in a row in order. A male screw portion 73a formed on an outer peripheral surface in the middle between the female screw portion 64c and the third fixing ring 73 is screwed to the cylinder 64a.

The third fixing ring 73 is a substantially cylindrical metal ring having a shape projecting in the outer diameter direction in a proximal end outer peripheral portion thereof. The third fixing ring 73 is not limited to the metal ring and may be a rigid cylinder including synthetic resin or plastic. A female screw portion 73b is formed in an inner peripheral surface on a proximal end side of the third fixing ring 73.

A holding ring 74, through which the distal end side guide tube 13 is inserted, is fit in the third fixing ring 73. A fourth fixing ring 75 is fixed to the third fixing ring 73. In other words, the fourth fixing ring 75 is fixed to the third fixing ring 73 by screwing the female screw portion 73b of the third fixing ring 73 and a male screw portion 75a of the fourth fixing ring 75.

At the point, both end faces of the holding ring 74 are fit and fixed in the third fixing ring 73 by an end face in the third fixing ring 73 and an end face in the fourth fixing ring 75 opposed thereto, respectively. In the holding ring 74, inward flanges 74a and 74b are formed around an axis toward an inner peripheral direction in the center and the proximal end portion of the inner peripheral surface of the holding ring 74.

As shown in FIGS. 14 and 15, the inward flanges 74a and 74b lock the corrugated concaves and convexes of the distal end side guide tube 13. Consequently, the distal end side guide tube 13 is connected to the guide tube fixing member 64 via the third fixing ring 73 and the fourth fixing ring 75. In the distal end portion of the distal end side guide tube 13, i.e., a portion indicated by reference sign G in FIG. 15, the distal end side guide tube 13 comes into a state in which the distal end side guide tube 13 is compressed against a surface on a distal end side of a step formed in the third fixing ring 73, whereby the guide tube fixing member 64 and the third fixing ring 73 are connected in a state in which water-tightness is maintained.

The two thrust generating members 70a and 70b serving as thrust generating means disposed in the first guide tube fixing member 64 include plate members in a substantially disc shape having predetermined thickness.

As shown in FIG. 16, holes 77 are drilled in substantially the center of the respective thrust generating members 70a and 70b. The holes 77 have a shape obtained by forming corners of a substantially rectangle in a curved line shape. The formation in the curved line shape is performed for preventing the thrust generating members 70a and 70b from being split.

The thrust generating members 70a and 70b are formed of, for example, synthetic natural rubber, silicon rubber, or the like. For example, a material thereof is an elastic body having a hardness range of A20 to A90 according to a spring type durometer hardness test type A (standard number: JIS-K-6253, International Standardization Organization: ISO7619).

Arrangements of the two thrust generating members 70a and 70b, the two pressing rings 71 and 72, and the third fixing ring 73 in the first guide tube fixing member 64 are explained in detail with reference to FIGS. 14, 15, and 17.

First, the first thrust generating member 70a is arranged to be in contact with an end face of the plate member 64b in a connection position of the cylinder 64a and the plate member 64b of the first guide tube fixing member 64. Subsequently, the pressing ring 71, the second thrust generating member 70b, and the pressing ring 72 are housed in the order in the cylinder 64a of the first guide tube fixing member 64. In other words, in the state, in the cylinder 64a, the first thrust generating member 70a, the pressing ring 71, the second thrust generating member 70b, and the pressing ring 72 are arranged in order from the proximal end side thereof.

The third fixing ring 73 is inserted into a proximal end opening of the cylinder 64a and the male screw portion 73a of the third fixing ring 73 and the female screw portion 64c of the cylinder 64a are screwed. In the state, a circumferential portion of the first thrust generating member 70a comes into contact with the end face of the plate member 64b and a proximal end circumferential portion of the pressing ring 71 and is held between both the members.

A circumferential portion of the second thrust generating member 70b comes into contact with a distal end circumferential portion of the pressing ring 71 and a proximal end circumferential portion of the pressing ring 72 and is held between both the members. A distal end circumferential portion of the pressing ring 72 is pressed against a proximal end circumferential portion of the third fixing ring 73.

The lengths in axial directions of the cylinder 64a, the two pressing rings 71 and 72, and the third fixing ring 73 are set such that the first and second thrust generating members 70a and 70b can be held with predetermined pressing forces, respectively. A distance between opposed surfaces of the first thrust generating member 70a and the second thrust generating member 70b is the same as the length in an axial direction of the pressing ring 71. Therefore, the first thrust generating member 70a and the second thrust generating member 70b are set to be a predetermined distance apart from each other according to the length in the axial direction of the pressing ring 71.

The distance the first thrust generating member 70a and the second thrust generating member 70b are apart from each other is set to a distance substantially equal to one pitch of the concaves and convexes formed on the spiral shape portion 51a of the rotating cylinder 51. In other words, the length in the axial direction of the pressing ring 71 and the thickness lengths of the respective thrust generating members 70a and 70b are set according to one pitch of the concaves and convexes formed on the spiral shape portion 51a.

Roughened surfaces as shift preventing means such as concave and convex surfaces for shift prevention may be formed on end faces in the circumferential portions of the two pressing rings 71 and 72 for pressing the respective thrust generating members 70a and 70b in order to maintain sure holdability when the first and second thrust generating members 70a and 70b are in contact with each other. In other words, when the pressed end faces of the two pressing rings 71 and 72 are formed as roughened surfaces, a large frictional force is generated on contact surfaces with the roughened surfaces, the first and second thrust generating members 70a and 70b are prevented from shifting against an external force and surely held in the guide tube fixing member 64 corresponding thereto.

In the holes 77 of the first and second thrust generating members 70a and 70b thus set in the guide tube fixing member 64, as shown in FIG. 17, the insertion portion main body 10 in the housing case main body 12 is inserted. At the point, the first and second thrust generating members 70a and 70b press the rotating cylinder 51 with a part of inner peripheral surfaces forming the respective holes 77 using an elastic force thereof.

As shown in FIG. 16, when the length of the long side is represented as L1 and the length of the short side is represented as L2, it goes without saying that the respective holes 77 of the first and second thrust generating members 70a and 70b have a relation L1<L2. When the length of a diameter in a concave portion is represented as L3 and the length of a diameter in a convex portion is represented as L4, it goes without saying that the rotating cylinder 51 forming the external shape portion of the insertion portion main body 10 inserted through the holes 77 has a relation L3<L4 because of the concaves and convexes of the spiral shape portion 51a.

In the present embodiment, as dimensions of the respective holes 77 and the concaves and convexes of the spiral shape portion 51a of the rotating cylinder 51 are set slightly shorter than the length L2 of the short side of the holes 77 and the length L3 of the diameter of the concave portion of the spiral shape portion 51a (L2<L3). The length L1 of the long side of the holes 77 is set longer than the length L4 of the diameter of the convex portion of the spiral shape portion 51a (L1>L4).

In other words, the first and second thrust generating members 70a and 70b elastically deform to press the concave portion of the spiral shape portion 51a on about two surfaces, with which the rotating cylinder 51 comes into contact, in the short side direction of the respective holes 77. When the rotating cylinder 51 rotates around the axis, the rotating cylinder 51 is subjected to a frictional force of the first and second thrust generating members 70a and 70b. The spiral shape portion 51a of the rotating cylinder 51 is moved forward and backward in the axial direction by a screw action in the respective holes 77 of the first and second thrust generating members 70a and 70b. The rotating cylinder 51 may be moved forward and backward by the screw action by setting a dimensional relation among the length L2 of the short side of the holes 77, the length L3 of the diameter of the concave portion of the spiral shape portion 51a, and the length L4 of the diameter of the convex portion of the spiral shape portion 51a as L3<L2<L4.

When the insertion portion main body 10 receives resistance equal to or larger than a predetermined amount in a test region, for example, from the intestinal wall of the body cavity, the rotating cylinder 51 is idly rotated with respect to the first and second thrust generating members 70a and 70b by the resistance to be prevented from moving forward in the depth direction of the test region.

In other words, as described above, the length L1 of the long side of the respective holes 77 of the first and second thrust generating members 70a and 70b is set longer than the length L4 of the diameter of the convex portion of the spiral shape portion 51a (L1>L4) and the rotating cylinder 51 is inserted through the holes 77 with the clearance with respect to the long side direction of the holes 77. Therefore, when a predetermined force (a frictional force in the forward direction) is applied to the rotating cylinder 51, the rotating cylinder 51 is idly rotated in the position of the holes 77 and cannot move forward in the depth direction of the test region.

Consequently, the rotating cylinder 51 is prevented from being excessively pushed in by generated thrust so as not to give a load to the test region, for example, the body cavity because of insertion more than necessary by the insertion portion main body 10 inserted by the rotating cylinder 51.

In the second guide tube fixing member 65, the thrust generating members 70a and 70b are not disposed. The second guide tube fixing member 65 has substantially the same configuration as the first guide tube fixing member 64 and is connected to the operation portion side guide tube 14.

Specifically, as shown in FIG. 18, the fourth fixing ring 75 is directly connected to the second guide tube fixing member 65. In other words, like the third fixing ring 73, the second guide tube fixing member 65 is connected to the operation portion side guide tube 14 by holding the holding ring 74, which locks the operation portion side guide tube 14, together with the fourth fixing ring 75.

The female screw portion 65c that screws with the male screw portion 75a of the fourth fixing ring 75 is formed on the proximal end inner peripheral surface of the cylinder 65a of the second guide tube fixing member 65.

Here, again, the end of the operation portion side guide tube 14 is pressed in a compressed state on the end face of the second guide tube fixing member 65 with which the holding ring 74 comes into contact. Water-tightness between the second guide tube fixing member 65 and the operation portion side guide tube 14 is maintained. The other end of the operation portion side guide tube 14, one end of which is connected to the second guide tube fixing member 65, is connected to the connector cover 15.

Next, connection of the operation portion side guide tube 14 and the connector cover 15 is explained with reference to FIGS. 19 to 21.

As shown in FIGS. 19 and 20, a holding ring 81 that locks, by screwing a fifth fixing ring 78 including a substantially cylindrical metal ring and a connection cylinder 79 including synthetic resin or plastic, the outer periphery of the proximal end portion of the operation portion side guide tube 14 is fit and held in the operation portion side guide tube 14. The holding ring 81 has a configuration same as that of the respective holding rings 59 and 74 that lock both the ends of the distal end side guide tube 13 and the distal end portion of the operation portion side guide tube 14. Therefore, detailed explanation of the configuration is omitted.

The fifth fixing ring 78 has a shape projecting in the outer diameter direction in a halfway portion thereof. A male screw portion 78a is formed in an outer periphery of a proximal end portion. The fifth fixing ring 78 is not limited to the metal cylinder and may be a rigid cylinder including synthetic resin or plastic.

The connection cylinder 79 has a shape projecting in the outer diameter direction in a distal end portion thereof. A female screw portion 79a is formed on an inner peripheral surface of the distal end portion. The connection cylinder 79 is extended toward a proximal end side thereof to draw circles at substantially equal intervals and has plural locking portions 80 for making the connector cover 15 detachably attachable.

In other words, the male screw portion 78a and the female screw portion 79a are screwed, whereby the fifth fixing ring 78 and the connection cylinder 79 are connected. The holding ring 81 are internally fit and held in a connection portion of the fifth fixing ring 78 and the connection cylinder 79. In the state, the proximal end portion of the operation portion side guide tube 14 is compressed and the proximal end outer peripheral portion is pressed against the end face with which the connection cylinder 79 comes into contact. Consequently, the operation portion side guide tube 14 is connected in a state in which water-tightness between the fifth fixing ring 78 and the connection cylinder 79 is maintained.

The locking portions 80 of the connection cylinder 79 connected to the connector cover 15 are connected to the connector cover 15. Specifically, the connector cover 15 has a connection portion 82 in which a cutout 82b (see FIG. 21) along the axial direction is formed in a cylinder in which outward flanges 82a are formed in distal end and proximal end portions thereof.

The plural locking portions 80 of the connection cylinder 79 are connected to the connection portion 82 to externally fit therein. The plural locking portions 80 have, in proximal end portions thereof, projecting portions 80a that project in an inner peripheral direction of the connection cylinder 79. Therefore, the projecting portions 80a lock the outward flanges 82a in the proximal end portion of the connection portion 82, whereby the connection cylinder 79 and the connector cover 15 are detachably connected.

Since the respective projecting portions 80a of the respective locking portions 80 simply catch the outward flanges 82a of the connection cylinder 79, the connection cylinder 79 is rotatable around the axis with respect to the connector cover 15. Therefore, the operation portion side guide tube 14 coupled to the connection cylinder 79 is also rotatably connected to the connector cover 15.

As shown in FIG. 20, a proximal end portion of the rotating cylinder 51 is fastened to the mouthpiece 83 by an adhesive or the like. The mouthpiece 83 is connected to a distal end portion of a rotating shaft 84 by a machine screw. Although not shown in the figure, the rotating shaft 84 is rotatably supported in the connector cover 15 as described later.

When the connector cover 15 is connected to the motor box 16 (see FIG. 1), a not-shown insertion portion side gear described later, which is provided in the rotating shaft 84, and a not-shown motor gear described later, which is provided in the motor box 16, mesh with each other. A driving force of the motor is transmitted to the respective gears. The rotating cylinder 51 rotates around the axis via the rotating shaft 84 and the mouthpiece 83.

Next, the respective guide tubes 13 and 14 are explained with reference to FIG. 22.

As described above, the guide tubes 13 and 14 are tube bodies including a so-called corrugated transparent or semi-transparent synthetic resin having light transmission properties, which are bellows tubes, on outer peripheral surfaces and inner peripheral surfaces of which concaves and convexes are formed. The guide tubes 13 and 14 have flexibility because of the concaves and convexes. Even if the guide tubes 13 and 14 are bent, the guide tubes 13 and 14 do not buckle and an inner diameter dimension thereof does not generally change.

In the guide tubes 13 and 14, the length as a minimum inner diameter dimension in a convex portion position projecting in an inner diameter direction thereof is represented as L4. The length L6 of a minimum inner diameter of the guide tubes is set larger than the length L5 as the outer diameter dimension in a convex portion position forming the spiral shape portion 51a of the rotating cylinder 51 (L6>L5). In other words, the guide tubes 13 and 14 are tube bodies through which the rotating cylinders 51 can be sufficiently inserted.

When torque around the axis is given to the rotating cylinder 51, slip change and shearing stress is generated in the inside of a material in the rotating cylinder 51 and twist stress is generated. Depending on the twist stress, the rotating cylinder 51 may change to a ring shape because of flexibility thereof.

Therefore, the length L6 of the minimum inner diameter of the guide tubes 13 and 14 is set to be smaller than two times of the length L5 as the outer diameter dimension in the convex portion position forming the spiral shape portion 51a of the rotating cylinder 51 (L6<2L5). The guide tubes 13 and 14 have predetermined hardness that allows the guide tubes 13 and 14 to endure deformed movement (fluctuation) due to the twist stress of the rotating cylinder 51.

The same applies to the housing case main body 12. As shown in FIG. 23, the distance L7 between the plate bodies 61 and 62 is set to be smaller than two times of the length L5 as the outer diameter dimension in the convex portion position forming the spiral shape portion 51a of the rotating cylinder 51 (L7<2L5) to prevent the rotating cylinder 51 from changing to a ring shape because of the twist stress. In other words, the length in the height direction of the respective frame bodies 63a to 63f fixing the two plate bodies 61 and 62 on the surfaces parallel to each other separated by the distance of L7 shown in FIG. 8 is set to L7. It goes without saying that the distance L7 between the plate bodies 61 and 62 is longer than the length L5 that is the outer diameter dimension in the convex portion position forming the spiral shape portion 51a of the rotating cylinder 51 (L7>L5).

In the insertion portion main body 10, an outer diameter of the length L5 in the convex portion position forming the spiral shape portion 51a of the rotating cylinder 51 is maximum outer diameter dimension.

Next, the connector main body 85 of the connector cover 15 is explained in detail with reference to FIGS. 24 to 32.

As shown in FIGS. 24 and 25, the connector cover 15 is made of rigid synthetic resin, and has the substantially box-shaped connector main body 85 that has the connection portion 82 described above located on a distal end side thereof, and is opened on one surface thereof. The connector main body 85 has plural beam portions to lay over both sides for improvement of rigidity.

On a bottom surface of the connector main body 85, as shown in FIG. 24, two bearing attaching surfaces 86 and 87, a content holding body attaching surface 88, and an electric connector attaching surface 89 are formed in a concave portion shape. The two bearing attaching surfaces 86 and 87 and the content holding body attaching surface 88 are located linearly along the center axis of the connection portion 82.

On both sides of the connector main body 85, tube through holes 90 of a substantially C shape for allowing the respective tubes 23 described above to extend from the inside to the outside and two engaging holes 91a and 91b of a long hole nearly substantially circle are formed. On inner surfaces on both the sides of the connector main body, as shown in FIG. 25, two guide grooves 92a and 92b in a substantially triangle shape and a linear groove 93 in which a tilt portion 93a is formed to widen in a proximal end portion thereof are formed in edge portions thereof.

The two guide grooves 92a and 92b are formed on the linear groove 93 and in a position where the two engaging holes 91a and 91b corresponding thereto are arranged on an axis orthogonal to a groove axis of the linear groove 93. On inner surfaces on both sides of the connector main body 85, inclined surfaces 94a and 94b (see FIG. 26) are formed between the guide grooves 92a and 92b and the engaging holes 91a and 92b.

As shown in FIG. 26, on both outer side surfaces of the connector main body 85, linear folding grooves 85a are formed in the forward/backward direction to connect the two engaging holes 91a and 91b.

As shown in FIG. 27, a cutout 95 to which a wire connection plate described later is detachably locked is formed in a proximal end face of the connector main body 85 of the connector cover 15. In a lower end (in FIG. 27, shown at an upper end) in the proximal end surface of the connector main body 85 in which the cutout 95 is formed, a locking projecting portion 95a projecting in the lateral direction is formed. In a halfway portion in the proximal end surface of the connector main body 85 in which the cutout 95 is formed, as shown in FIG. 28, a locking convex portion 95b slightly projecting in the lateral direction is formed.

In the connector main body 85, two bearing portions (hereinafter simply referred to as bearing) 97 that rotatably support the rotating shaft 84 shown in FIG. 29, an active side electric connector (hereinafter simply referred to as electric connector) 99 on a male side shown in FIG. 30, and a content holding body 103 shown in FIG. 31 are disposed.

As shown in FIG. 29, an insertion portion side gear 96 serving as a second gear is fit in a halfway portion of the rotating shaft 84. The rotating shaft 84 and the insertion portion side gear 96 may be integrally formed. As described above, the mouthpiece 83 to which the rotating cylinder 51 is fastened is fixed to a distal end of the rotating shaft 84 by a screw 83a.

The rotating shaft 84 is rotatably supported by two bearings 97. Specifically, one bearing 97 rotatably supports the distal end side of the rotating shaft 84 between the mouthpiece 83 and the insertion portion side gear 96. On the other hand, the other bearing 97 rotatably supports the rotating shaft 84 further on a proximal end side than the insertion portion side gear 96.

The bearings 97 are formed in a substantially square pole shape in which holes for rotatably supporting the rotating shaft 84 are formed. The bearings 97 have engaging leg portions 97a projecting from four corners of one surface, respectively. In the bearings 97, bearing side elastic members 98 such as sponge are pasted to a surface side on the opposite side of one surface having the four engaging leg portions 97a. The bearings 97 are fastened to the bearing attaching surfaces 86 and 87 of the connector main body 85 via the bearing side elastic member 98.

As shown in FIG. 30, the electric connector 99 has a connector portion 100 and two projecting portions 99a projecting from surfaces at both ends, respectively. The communication cable 33 described above is extended from the electric connector 99. The electric connector 99 is fixed to a substrate 101.

In the electric connector 99, an elastic member 102 such as sponge is pasted to a rear surface of the substrate 101. The electric connector 99 is fastened to the connector attaching surface 89 of the connector main body 85. The two projecting portions 99a are formed in a substantially pyramid shape pointed in a projecting direction.

As shown in FIG. 31, the content holding body 103 is formed in a substantially square pole shape and has projecting portions 103a that project from four corners of one surface, respectively. In the content holding body 103, four guide grooves 105 through which the respective bending operation wires 44, which are one of contents in the endoscope insertion portion with housing case 6, are inserted, respectively, are formed. Holes 104 through which the respective tubes 23 and the communication cable 33, which are contents of the endoscope insertion portion with housing case 6 are pierced through the content holding body 103.

In the content holding body 103, a connector side elastic member 106 such as sponge is pasted to a surface side on the opposite side of the surface in which the two projecting portions 103a is provided. The content holding body 103 is fastened to the content holding body attaching surface 88 of the connector main body 85 via the connector side elastic member 106. An inner layer tube fixing tube 107 is coupled to a surface on a distal end side of the content holding body 103.

The two bearings 97, the electric connector 99, and the content holding body 103 explained above are disposed in the inside of the connector main body 85 of the connector cover 15 as shown in FIG. 32 via the respective bearing side elastic members 98, 102, and 106. The two bearings 97 and the content holding body 103 are linearly arranged.

Next, a wire connection plate 108 that is a part of the connector cover 15 and locked to the cutout 95 formed in the proximal end surface of the connector main body 85 is explained.

As shown in FIGS. 33 and 34, the wire connection plate 108 is a plate body of a substantially C shape in a lateral cross sectional shape mainly including two side plates 109, a wire anchor holding plate 110, and a coupling plate body 112.

The two side plates 109 are vertically fixed to a plate surface of the wire anchor holding plate 10 on both sides of the wire anchor holding plate 110. On respective opposed surfaces of the side plates 109, as shown in FIGS. 35 and 36, two engaging convex portions 113 and 114 of a substantially diamond shape are protrudingly provided. In other words, the two engaging convex portions 113 and 114 form a step projecting to the center of the wire connection plate 108.

The first engaging convex portion 113 is disposed on a proximal end side of the side plate 109 in a direction away from the coupling plate body 112. The second engaging convex portion 114 is disposed on a distal end side of the side plate 109 in the vicinity of the coupling plate body 112.

In the first engaging convex portion 113, compared with the second engaging convex portion 114, the lengths in the up, down, left, and right directions along the plate surface of the side plate 109 are set small. In the first engaging convex portion 113, a tilt portion 113a tilting upward (in an upward direction viewed on the paper surface of FIGS. 35 and 36) is formed in the proximal end portion in a distal end direction.

On the other hand, in the second engaging convex portion 114, a tilt portion 114a, a proximal end portion of which tilts upward from a lower end (a lower side viewed on the paper surface of FIGS. 35 and 36) of the side plate 109, is formed.

As shown in FIG. 37, the wire anchor holding plate (hereinafter simply abbreviated as holding plate) 110 is a vertically long plate body having concaves and convexes of a substantially hat shape in a cross section. Specifically, the wire anchor holding plate 110 includes a concave plate portion 110a formed in a concave shape, a cross section of which is a C shape, and collar plate portions 110b extending to side directions from both edge side portions of the concave plate portion 110a, respectively.

Referring back to FIGS. 33 and 34, fourth long grooves 111 having predetermined length are formed along a major axis direction in the wire anchor holding plate 110. Among the long grooves 111, two long grooves 111b and 111c are formed on a bottom surface of the concave plate portion 110a. The remaining two long grooves 111a and 111d are formed in the two collar plate portions 110b, respectively. In other words, the two long grooves 111a and 111d are arranged to sandwich the two long grooves 111b and 111c of the concave plate portion 110a, respectively, with one of the long grooves 111a and 111d formed on the respective collar plate portion 110b on the outer side of the concave plate portion 110a.

A coupling plate body 112 having a surface perpendicular to the respective plate surfaces is coupled to the distal end side of the side plates 109 and the wire anchor holding plate 110. The coupling plate body 112 has a concave locking groove 112a along respective sides on both the sides thereof. As shown in FIG. 38, the coupling plate body 112 has four wire inserting portions 115 that are plural holes formed in the center of a plate surface thereof and through which the four bending operation wires 44 are inserted.

The wire inserting portions 115 are positioned in the coupling plate body 112 such that the holes through which the respective bending operation wires 44 are inserted and held correspond to the respective four long grooves 111 formed in the wire anchor holding plate 110.

Specifically, among the four wire inserting portions 115, the two wire inserting portions 115a and 115d in an outer side direction are disposed in positions corresponding to the long grooves 111a and 111d formed in the respective collar plate portion 110b of the wire anchor holding plate 110 on the plate surface of the coupling plate body 112. The two wire inserting portions 115b and 115c are disposed in positions corresponding to the long grooves 111b and 111c formed in the concave plate portion 110a of the wire anchor holding plate 10 on the plate surface of the coupling plate body 112.

In other words, in the coupling plate body 112, the two wire inserting portions 115a and 115d are provided in parallel on a plate surface upper side of the coupling plate body 112. The two wire inserting portions 115b and 115c are disposed on a plate surface lower side of the coupling plate body 112 between the wire inserting portions 115a and 115d.

The coupling plate body 112 has two guide grooves 116 that are cutout formed, from below, from the center where the wire inserting portions 115 are provided to both side portions.

In the wire connection plate 108 configured as described above, a wire anchor 117 to which a distal end portion of each of the four bending operation wires 44 is connected as shown in FIGS. 39 to 42 is disposed in each of the long grooves 111 formed in the wire anchor holding plate 110.

The wire anchor 117 includes a locking plate portion 119 of a substantially T shape in a lateral cross section and a substantially cylindrical wire anchoring tube 118 to which the bending operation wire 44 is connected.

The wire anchoring tube 118 includes a substantially annular anchor side locking portion 118a of a flange shape projecting in an outer peripheral direction at a proximal end portion on the opposite side of a side to which the bending operation wire 44 is connected to extend out two slits 118b along a major axis formed in side peripheral surfaces, and a hole 118c through which the bending operation wire 44 is inserted.

The locking plate portion 119 includes an upper plate portion 119a and a coupling plate body 119b extended from the center of the upper plate portion 119a along a major axis and having a step 119c.

Respective major axis directions of the locking plate portion 119 and the wire anchoring tube 118 are matched. The coupling plate body 119b of the locking plate portion 119 is arranged on an outer peripheral portion of the wire anchoring tube 118.

The proximal end portion of the bending operation wire 44 is inserted through the hole 115c of the wire anchoring tube 118 of the wire anchor 117 as described above. The wire anchor 117 and the bending operation wire 44 are fastened by welding such as soldering. In the present embodiment, since there are the four bending operation wires 44, the wire anchors 117 are fastened to the proximal end portions of the respective bending operation wires 44, respectively.

The wire anchors 117 fastened to the proximal end portions of the bending operation wires 44 are, as shown in FIGS. 43 and 44, arranged in the respective long grooves 111 formed in the wire anchor holding plate 110 of the wire connection plate 108 described above.

Specifically, the respective wire anchors 117 are disposed in the long grooves 111 one by one such that the respective upper plate portions 119a and the steps 119c of the coupling plate bodies 119b are held sandwiching both the surfaces of the wire anchor holding plate 110. When the respective wire anchors 117 are disposed in the respective long grooves 111 of the wire anchor holding plate 110, an arranging direction thereof is determined such that a direction in which the respective bending operation wires 44 extend is on the coupling plate bodies 112 side of the wire connection plate 108 and the respective upper plate portions 119a are in an identical direction and on an upper side viewed on the respective paper surfaces that is the upper surface of the wire connection plate 108.

At the point, the two wire anchors 117 to which two bending operation wires 44 for bending the bending portion in the up to down direction among the four bending operation wires 44 are fastened are arranged in the two long grooves 111a and 111d formed in the collar plate portion 110b of the wire anchor holding plate 110, respectively.

The two wire anchors 117 to which the two bending operation wires 44 for bending the bending portion 9 in the left to right direction are fastened are arranged in the two long grooves 111b and 111c formed in the concave plate portion 110a of the wire anchor holding plate 110, respectively.

Thus, the four wire anchors 117 disposed in the long grooves 111 of the wire anchor holding plate 110, respectively, freely move forward and backward along the respective long grooves 111. In other words, the four wire anchors 117 are restricted from moving in directions other than a forward/backward tugging and loosening direction along the respective long grooves 111 of the wire anchor holding plate 110. Therefore, the respective bending operation wires 44 are substantially regulated from moving in directions other than the forward/backward tugging and loosening direction.

As shown in FIGS. 45 and 46, in the wire connection plate 108 configured as described above, the coupling plate body 112 is connected to the cutout 95 formed on the proximal end face of the connector main body 85 of the connector cover 15 such that the side plates 109 and the wire anchor holding plate 110 extend in the proximal end direction.

Specifically, the locking grooves 112*a* (see FIGS. 33 and 34) formed in the both side portions of the coupling plate body 112 of the wire connection plate 108 are inserted into the edge portions forming the cutout 95 of the connector main body 85. At the point, the coupling plate body 112 is caught by the locking projecting portion 95*a* disposed in the cutout 95 of the connector main body 85. The wire connection plate 108 is prevented from coming off the cutout 95 of the connector main body 85.

The coupling plate body 112 is arranged in the connector main body 85 to be movable in a range of formation of the cutout 95, i.e., a range of the length of the cutout 95 in the depth direction of the connector main body 85.

The coupling plate body 112 may be held in the vicinity of the edge portion of the connector main body 85 forming the cutout 95 facing an inserting direction (an upper end face of the connector main body 85 forming the cutout 95 on the paper surface of FIG. 45) by the locking convex portion 95*b* disposed in the cutout 95.

As shown in FIGS. 47 and 50, the connector cover 15 is completed by assembling the respective members configured as described above.

As shown in FIGS. 48 and 49, the inner layer tube 49*a* is held by the two annular members of the inner layer tube fixing tube 107 and fixed such that the proximal end portion thereof expands.

The respective bending operation wires 44, which are contents inserted through the inner layer tube 49*a*, are inserted through the guide grooves 105 of the content holding body 103 and divided as shown in FIG. 50.

As shown in FIGS. 48 and 49, the bending operation wires 44 are substantially linear from the content holding body 103 to the respective wire anchors 117 fastened to the proximal ends.

As shown in FIG. 50, the respective tubes 23 and the communication cable 33, which are contents inserted through the inner layer tube 49*a*, are inserted through the holes 104 of the content holding body 103, respectively. An outer diameter of the aspiration tube 23*c* among the respective tubes 23 is the largest. According to the outer diameter, the holes 104 have a shape of hole surfaces thereof in which steps of long holes are formed.

As shown in FIG. 50, the hole 104 has a hole surface of an elliptical shape in which a portion through which the aspiration tube 23*c* can be inserted and a portion through which the air feed tube 23*a*, the water feed tube 23*b*, and the communication cable 33 can be inserted are connected. In the present embodiment, the air feed tube 23*a*, the aspiration tube 23*c*, the communication cable 33, and the water feed tube 23*b* are inserted in parallel in holes 104 in order from the left on the paper surface of FIG. 50.

In the state, the aspiration tube 23*c* is restricted from moving from in the vicinity of the center on the left side to the right side by the step of the hole 104. Therefore, an excess load is not given to the respective tubes 23 and the communication cable 33 and the respective tubes 23 and the communication cable 33 do not overlap each other.

Next, the motor box 16, the grasping portion 17, and the main operation portion 18 of the operation portion 7 are explained in detail with reference to FIGS. 51 to 69.

Explanation of the respective components of the operation portion 7 explained with reference to FIG. 1 is omitted.

In the main operation portion 18 of the operation portion 7, as shown in FIGS. 51 and 52, on a surface from which the universal cord 18*a* extends, an advancing and retracting switch 120 for driving a motor disposed in the motor box 16 is disposed to be rotatable in a direction indicated by an arrow in the figure. Like the foot switch 25 described above, the advancing and retracting switch 120 is a switch for instructing rotating of the rotating cylinder 51 of the insertion portion main body 10.

First, the motor box 16 is explained with reference to FIGS. 53 to 59.

As shown in FIGS. 53 and 54, the motor box 16 mainly includes a housing 121 of a substantially box shape including metal or rigid synthetic resin covered with a lid body 121*a* in which a cutout is formed, a motor cover 122 as a cover body of a substantially box shape that closes a cutout 121*b* of the lid body 121*a* with one surface, a motor 124 as driving means including a motor gear 123 serving as a first gear, a passive side electric connector on a female side (hereinafter simply referred to as electric connector) 125, two guide portions 126 projecting from the lid body 121*a*, and four engaging convex portions 127 projecting from both sides of the housing 121. Guide convex portions 121*c* projecting from sides on a distal end side are formed in the motor box 16.

The two guide portions 126 are disposed in a proximal end portion of the lid body 121*a* of the housing 121 to be spaced apart from each other in both side directions at a predetermined distance from an extended line of a center line in a longitudinal direction of the motor cover 122 formed in the housing 121. The guide portions 126 are plates, on outer side surfaces on a distal end side of which taper surfaces 126*a* are formed and projecting sides of which draw arcs as shown in FIG. 54. The guide portions 126 are disposed in the lid body 121*a* such that longitudinal directions thereof are parallel to a longitudinal direction of the housing 121.

As shown in FIG. 55, the electric connector 125 is disposed on the substrate 129. The electric connector 125 has a connector portion 128 in substantially the center of an upper surface thereof and has two engaging holes 125*a* in the same upper surface on both sides of the connector portion 128.

The engaging holes 125*a* have a shape tapered downward as shown in FIGS. 56 and 57. In other words, the electric connector 125 has slope portions 125*b* on respective sides forming the respective engaging holes 125*a*. The engaging holes 125*a* communicate with holes 129*a* formed in the substrate 129.

The electric connector 125 is exposed on one surface of the lid body 121*a* of the motor box 16.

As shown in FIG. 54, the motor cover 122 fixedly holds the motor 124 on a rear surface thereof. As shown in FIG. 58, the motor cover 122 is formed substantially in a C shape in section. In one surface forming a bottom surface, plural engaging holes 130 and 132 and a hole 131 in which the engaging holes 130 are formed at four corners, respectively, and from which the motor gear 123 of the motor 124 is exposed are drilled.

Eight engaging holes 130 are formed in one surface of the motor cover 122. In the engaging holes 130, as described later, when the motor box 16 and the connector cover 15 are coupled, the engaging leg portions 97*a* of the bearings 97 of the connector cover 15 are inserted, respectively. As shown in FIG. 59, the engaging holes 130 respectively have inclined surfaces 133 inclined toward a direction in which the motor 124 is housed. In the motor cover 122, a chamfer for making it easy to forward the respective engaging leg portions 97a to edge portions where the respective engaging holes 130 is formed.

Next, the internal structure of the grasping portion 17 and the main operation portion 18 is explained with reference to FIGS. 60 to 68.

As shown in FIGS. 60 to 62, the grasping portion 17 is formed of metal or rigid synthetic resin. An external shape of the grasping portion 17 is formed by a hollow substantially prism having, in a distal end portion thereof, a coupling portion 17a for coupling the motor box 16.

In the grasping portion 17, four coupling members 134 and 135 that are bending wire locking members to which ends of the UD (UP/DOWN) chain 136 and the RL (RIGHT/LEFT) chain 137 are connected, respectively, a base plate 138 that guides the two RL side coupling members 135 to move linearly and functions as a framework of the grasping portion 17 and the main operation portion 18, two first guide plates 139 disposed on a distal end side of the base plate 138, and two second guide plates 140 that function as wire connection plate engaging portions fixed to both sides of the base plate 138 are disposed.

On both sides of an upper surface of the base plate 138, four spacers 141 that vertically divide and hold the coupling members 134 and 135 are placed. In the center of the spacers 141, a partition plate 142 integrally including L-shaped two arm portions 142a bent vertically to oppose to each other are disposed.

Specifically, as shown in FIG. 61, two rail portions 138a project along a major axis on the upper surface of the base plate 138. On bottom surface of the respective RL side coupling members 135, concave linear grooves that fit in the rail portion 138a corresponding thereto are formed. Ends in an outer side directions of the RL side coupling members 135 are held by the spacers 141 to freely move forward and backward.

The UD side coupling members 134 are superimposed on upper surfaces on outer side portions of the respective RL side coupling members 135 via the partition plate 142. The UD side coupling members 134 are held by the spacers 141 at ends in the outer side direction to freely move forward and backward and guided by the arm portions 142a of the partition plate 142 to move linearly. On upper surfaces of the spaces 141, a cover 145 that covers up to the inside of the main operation portion 18 is disposed. The respective members excluding the coupling members 134 and 135 are fixed to the base plate 138 by plural fixing screws 146.

As shown in FIG. 62, the two guide plates 140 are fixed to plural guide plate fixing screws 147 on both sides of the base plate 138. In the respective chains 136 and 137 connected to the respective coupling members 134 and 135, the UD chain 136 is disposed on the arm portions 142a of the partition plate 142 and the RL chain 137 is disposed on the base plate 138.

Reference numeral 149 shown in FIGS. 61 and 62 denotes electric cables. The electric cables 149 are a power supply cable for driving the motor 124 of the motor box 16 and a cable for supplying electric power to the image pickup device 31 and the LED 34 in the distal end portion 8 of the endoscope insertion portion with housing case 6 and supplying an instruction signal. The electric cables 149 are inserted through a rear surface side of the base plate 138.

As shown in FIG. 63, on both sides of a coupling portion of the grasping portion 17 and the main operation portion 18, stoppers 148 that stop the respective coupling members 134 and 135, which freely move forward and backward, are disposed.

Two sprockets are rotatably disposed to superimpose each other in the main operation portion 18. One of the sprockets is coupled to the UD bending operation knob 19a, although not shown in the figure, and the other is coupled to the RL bending operation knob 19b.

The sprockets are rotated in association with the rotating of the respective bending operation knobs 19 and the respective chains 136 and 137 are moved forward and backward according to the rotating of the sprockets. The bending operation mechanism 18c is configured by the sprockets, the respective chains 136 and 137, and the like.

Next, the four coupling members 134 and 135 are explained with reference to FIG. 64.

As shown in FIG. 64, in the four coupling members 134 and 135, the two UD side coupling members 134 form a pair and the two RL coupling members form a pair.

Each of the two UD side coupling members 134 is formed in a substantially square pole shape including metal and has a chain connection portion 134a, to a proximal end portion disposed on the main operation portion 18 side of which one end of the UD chain 136 is connected, an anchor locking hole 150 drilled from the center of one surface as an upper surface to a distal end along a longitudinal direction and formed such that plural concave portions continue, and a convex portion 134b that project from a distal end side surface on the opposite side of surface opposed to each other.

Each of the two RL side coupling members is formed in a substantially square pole shape having a dimension in the width direction twice as large as that of the UD side coupling members 134 and has a chain connection portion 135a, to a proximal end portion arranged on the main operation portion 18 side of which one end of the RL chain 137 is connected, the anchor locking hole 150 drilled from the center of one surface as an upper surface to a distal end along a longitudinal direction, and a convex portion 135b that projects from a distal end side surface on the opposite side of surfaces opposed to each other.

The anchor locking hole 150 formed in the respective coupling members 134 and 135 is a long hole, a surface of which is plural continuing ellipses, and formed to the depth of the substantially center of the respective coupling members 134 and 135. In the respective coupling members 134 and 135, coupling member side locking portions 150a projecting to be opposed to the center of the hole in portions where the ellipses cross viewed from the upper surface are formed on the hole surface forming the anchor locking hole 150.

As described above, the coupling members 134 and 135 move forward and backward according to tugging and loosening of the respective chains 136 and 137 with the sprockets in association with the rotating of the bending operation knobs 19. A range of movement in the proximal end direction of the forward and backward movement of the coupling members 134 and 135 is regulated by the four stoppers 148.

As shown in FIG. 65, the stoppers 148 are formed in a substantially square pole shape including metal. As shown in FIG. 63, the two stoppers 148 superimpose on both the sides on the base plate 138 in the coupling portion of the grasping portion 17 and the main operation portion 18 and are fixed by fixing members such as screws.

The stoppers 148 have locking convex portions 148a projecting from surfaces opposed to each other on the proximal end portion side. As shown in FIGS. 66 and 67, for example, when the UD side coupling members 134 are tugged to the proximal end side, in the stoppers 148, distal end surfaces of the locking convex portions 148a thereof come into contact with proximal end surface of the convex portions 134b of the UD side coupling members 134 and stop the movement in the proximal end direction of the UD side coupling members 134. Similarly, the RL side coupling members 135 are also regulated from moving in the proximal end direction by the stoppers 148.

The respective coupling members 134 and 135 are not moved to the distal end side when the coupling members 134 and 135 forming pairs therewith are regulated to move on the proximal end side. In other words, when one of the coupling members 134 and 135 forming pairs is regulated, the rotating operation of the respective bending operation knobs 19 cannot be performed and the tugging and loosening of the respective chains 136 and 137 is stopped. In other words, since the respective coupling members 134 and 135 are connected to both the ends of the respective single chains 136 and 137, the other coupling members 134 and 135 are also stopped.

Therefore, the respective coupling members 134 and 135 forming pairs move the same distance in opposite directions by an amount of tugging and loosening of the respective chains 136 and 137 via the sprockets according to the rotating of the bending operation knobs 19. A range of forward and backward movement of the respective coupling members 134 and 135 is regulated to a distance set in advance by the stoppers 148.

Next, the first guide plate 139 and the second guide plate 140 are explained with reference to FIGS. 68 and 69.

As shown in FIG. 68, the two first guide plates 139 are plate bodies, upper surface portions of which are a trapezoidal shape. The first guide plates 139 have guide surfaces 139a, which are slopes connecting upper sides and lower sides forming the trapezoids, on both ends thereof. The first guide plates 139 are fixed to both the sides on the distal end side of the base plate 138 (see FIG. 60) side by side by fixing screws such that the respective guide surfaces 139a are set in the outer side direction.

As shown in FIG. 69, in the two second guide plates 140, two engaging cutout portions 151 and 152, which are cutouts of a substantially trapezoidal shape, are formed on one side portions. In the second guide plates 140, first engaging cutout portions 151 are disposed on a proximal end side and second engaging cutout portions 152 are disposed on a distal end side.

The respective second guide plates 140 have first slope portions 151a in one side portions on the proximal end side where the first engaging cutout portions 151 are formed and have second slope portions 152a in one side portions on the proximal end side where the second engaging cutout portions 152 are formed.

The second guide plates 140 are vertically fixed to the upper surface of the base plate 138 on both the sides of the base plate 138 such that the side portions where the respective engaging cutout portions 151 and 152 are formed are set upward.

The grasping portion 17 continuously provided with the main operation portion 18 configured as explained above is coupled to the motor box 16 when the coupling portion 17a in the distal end portion is fit in the proximal end surface of the motor box 16. In the operation portion 7, the grasping portion 17 is coupled (docked) to the motor box 16 such that one surface of the main operation portion 18 on which the bending operation knobs 19 are disposed and one surface on which the motor gear 123 of the motor box 16 is exposed face an identical direction.

The universal cord 18a, the bend preventing portion 18b, the two bending operation knobs 19, the various switches 20, 21, and 120, and the like are assembled to the main operation portion. Thus, the motor box 16, the grasping portion 17, and the main operation portion 18 are continuously provided in order from the distal end and the operation portion 7 shown in FIG. 51 is configured.

Next, the coupling (hereinafter referred to as docking as well) of the connector cover 15 and the motor box 16 is explained with reference to FIGS. 70 to 106.

The connector cover 15 is docked to the motor box 16 to change from a state shown in FIG. 70 to a state shown in FIG. 71. When viewed in section, the connector cover 15 is docked to the motor box 16 to change from a state shown in FIG. 72 to a state shown in FIG. 73.

At the point, the insertion portion side gear 96 disposed in the connector cover 15 and the motor gear 123 of the motor 124 built in the motor box 16 are meshed. The electric connector 99 on the male side disposed in the motor box 16 and the electric connector 125 on the female side disposed in the motor box 16 are electrically connected. Moreover, the four wire anchors 117 fastened to the respective ends of the bending operation wires 44 disposed in the wire connection plate 108 of the connector cover 15 are inserted in association with the respective four coupling members 134 and 135 disposed in the grasping portion 17.

The docking of the connector cover 15 and the motor box 16 describe above is specifically explained. The respective coupling members 134 and 135 disposed in the grasping portion 17 of the operation portion 7 are slid to initial positions in the grasping portion 17 by a predetermined assisting tool, although not shown in the figure.

First, as shown in FIGS. 74 and 75, the connector cover 15 is slid as a first action to move close to the motor box 16 from the distal end direction to the proximal end direction. At the point, the proximal end portion of the wire connection plate 108 of the connector cover 15 is inserted into the grasping portion 17.

As shown in FIG. 76, the wire connection plate 108 is guided linearly to the two guide portions 126 in which surfaces on the inner side of the respective side plates 109 project from one surface on the proximal end portion of the motor box 16. At the point, since the taper surfaces 126a (see FIG. 53) are formed on the surface in the outer side distal end portions of the two guide portions 126, even if shift slightly occurs in a position in the lateral direction, the surface on the inner side of the distal end portion of the respective side plates 109 are guided such that the wire connection plate 108 can move linearly in the major axis direction of the grasping portion 17.

Moreover, in the wire connection plate 108, even if shift slightly occurs in a position in the lateral direction, the surfaces on the inner side in the distal end portions of the respective side plates 109 are guided linearly in the major axis direction of the grasping portion 17 by the respective guide surfaces 139a (see FIG. 68) of the two first guide plates 139 in the grasping portion 17 in the same manner as the two guide portions 126. The respective guide surfaces 139a regulates the movement in the left to right direction, which is the lateral direction of the wire connection plate 108, and slight shift allowance is set.

In the wire connection plate 108, the surfaces on the inner side of the respective side plates 109 are guided linearly by the sides of the first guide portions 126.

When the connector cover 15 slides to the motor box 16, as shown in FIG. 77, the tilt portion 93a formed at the proximal end of the inner surface side of the connector cover 15 guides the guide convex portions 121c projecting from the side of the motor box 16 and the four engaging convex portions 127

(only one is shown in FIG. 77). The guide convex portions 121c and the engaging convex portions 127 are guided to the linear grooves 93.

Since the two guide convex portions 121c of the motor box 16 and the four engaging convex portions 127 are guided along the linear grooves 93, respectively, the connector cover 15 is regulated from sliding in parallel to the motor box 16. As shown in FIG. 78, the connector cover 15 is slid in parallel to the motor box 16 to a position where the four engaging convex portions 127 of the motor box 16 corresponding to the four guide grooves 92a formed in the inner side surfaces, respectively, are inserted.

The wire connection plate 108 of the connector cover 15 is housed in the grasping portion 17 while being guided linearly and regulated in position. At the point, the wire connection plate 108 is positioned in the up to down direction in the grasping portion 17 by the two second guide plates 140 disposed in the grasping portion 17.

Specifically, as shown in FIGS. 79 to 81, the two engaging convex portions 113 and 114, which project from the respective surfaces to which the respective side plates 109 of the wire connection plate 108 are opposed, are inserted into the two engaging cutout portions 151 and 152 formed in the two second guide plates 140.

First, as shown in FIG. 79, the wire connection plate 108 guided linearly is sent in the depth direction of the grasping portion 17 in a state in which the engaging convex portion 113 on the proximal end side passes the second engaging cutout portion 152 on the distal end side of the second guide plate 140 and the lower surface of the engaging convex portion 113 is along the upper surface in the center of the second guide plate 140.

Then, as shown in FIG. 80, the wire connection plate 108 is sent in the depth direction of the grasping portion 17 in a state in which the lower surface of the second engaging convex portion 114 on the distal end side is along the upper surface of the distal end side of the second guide plate 140. At the point, the first tilt portion 113a of the first engaging convex portion 113 comes into contact with the first slope portion 151a of the first engaging cutout portion 151 of the second guide plate 140 and is guided to move obliquely downward in the proximal end direction along the first slope portion 151a. The second tilt portion 114a of the second engaging convex portion 114 also comes into contact with the second slope portion 152a of the second engaging cutout portion 152 and is guided to move obliquely downward in the proximal end direction along the second slope portion 152a.

In other words, the respective engaging convex portions 113 and 114 are guided along the respective engaging cutout portions 151 and 152 of the second guide plate 140 and the wire connection plate 108 translates to be dropped obliquely downward in the proximal end direction. In other words, the respective engaging convex portions 113 and 114 are inserted into the respective engaging cutout portions 151 and 152 corresponding thereto.

When the wire connection plate 108 is inserted into the grasping portion 17 and translates obliquely downward in the proximal end direction to be dropped and is positioned in the grasping portion 17 by the second guide plate 140, the wire anchors 117 disposed to freely move forward and backward in the wire anchor holding plate 110 of the wire connection plate 108 are inserted into the anchor locking holes 150 corresponding thereto of the respective coupling members 134 and 135 disposed in the grasping portion 17.

Figure 82:
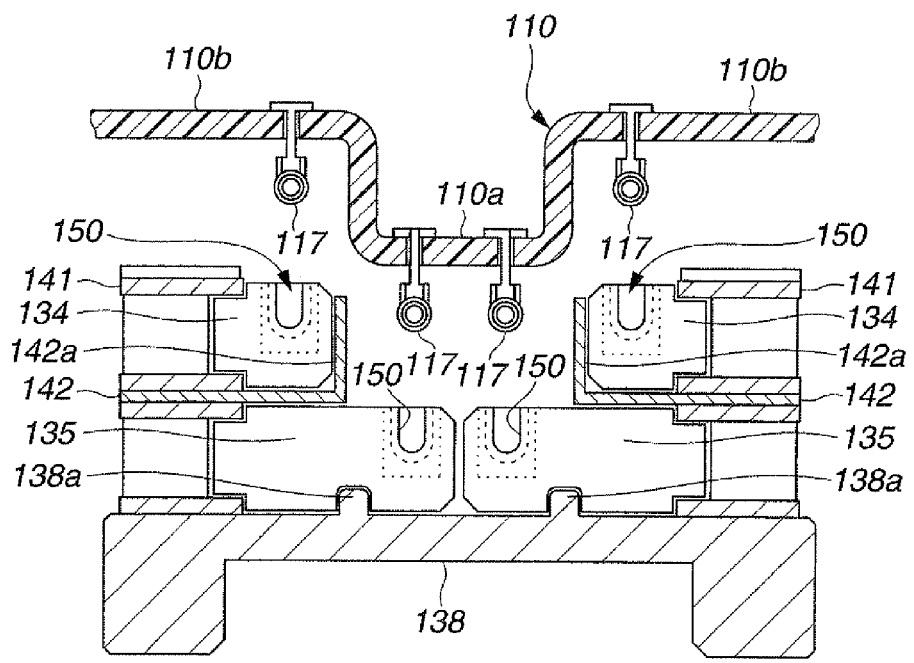
FIG. 82 is a diagram for explaining a state in which the wire anchor of the wire connection plate is inserted in an anchor locking hole of the coupling member according to the embodiment.
Figure 83:
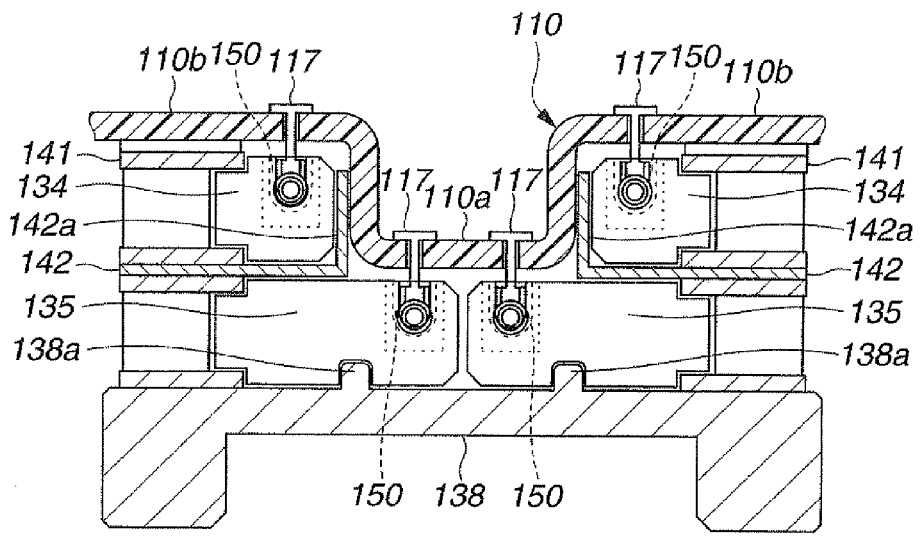
FIG. 83 is a diagram for explaining a state in which the wire anchor of the wire connection plate is inserted in the anchor locking hole of the coupling member according to the embodiment.

Specifically, as shown in FIGS. 82 and 83, the wire anchor holding plate 110 of the wire connection plate 108 is slid to the respective coupling members 134 and 135. At the point, the concave plate portion 110a of the wire anchor holding plate 110 is inserted between the respective arm portions 142a of the partition plate 142.

Figure 84:
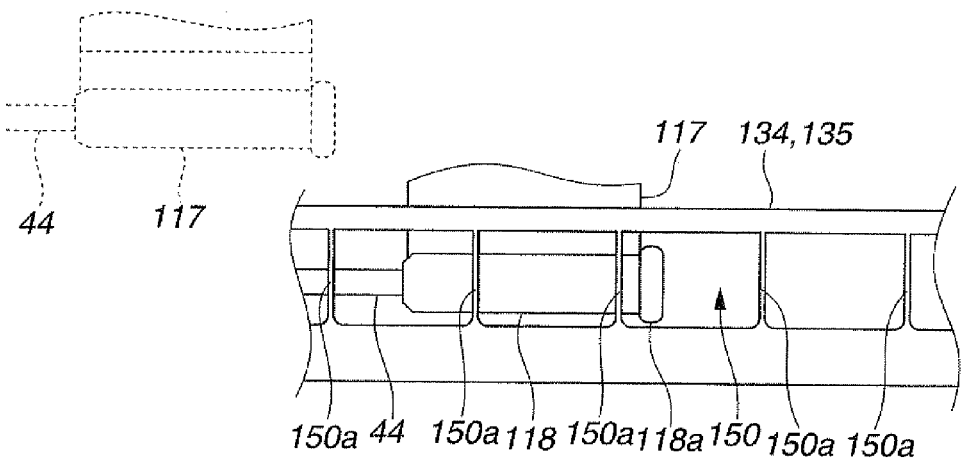
FIG. 84 is a diagram for explaining a state in which the wire anchor of the wire connection plate is inserted in the anchor locking hole of the coupling member according to the embodiment.
Figure 85:
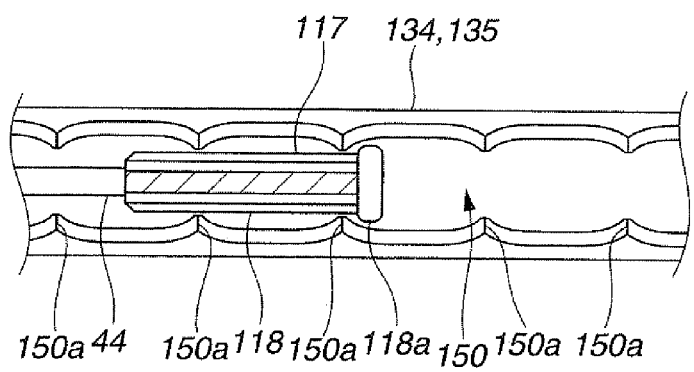
FIG. 85 is a diagram for explaining a state in which the wire anchor of the wire connection plate is inserted in the anchor locking hole of the coupling member according to the embodiment.
Figure 86:
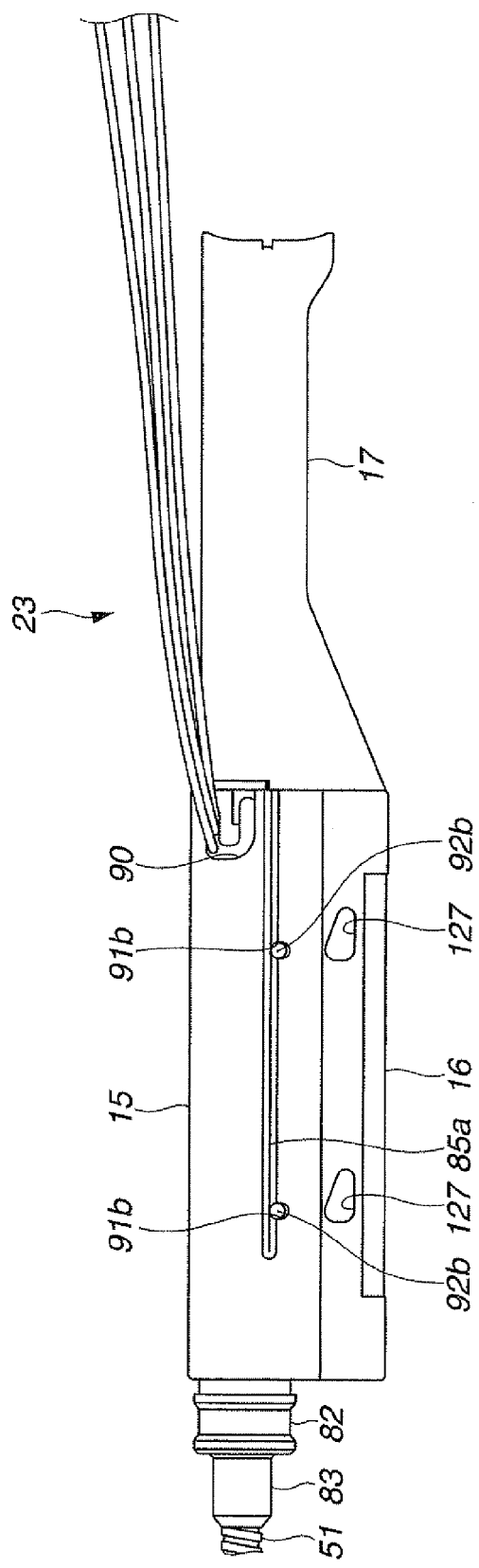
FIG. 86 is a side view showing a state in which the connector cover docks with the motor box according to the embodiment.

When the wire anchor holding plate 110 translates obliquely downward in the proximal end direction, as shown in FIGS. 84 and 85, the respective wire anchors 117 simultaneously (at a time) enter the anchor locking holes 150 of the respective coupling members 134 and 135 to which the respective wire anchoring tubes 118 correspond. At the point, the anchor side locking portions 118a of the wire anchoring tubes 118 are regulated from moving to the distal end side by the coupling member side locking portions 150a forming a part of the hole walls of the anchor locking holes 150.

In other words, the anchor side locking portions 111a configure outward flanges and the coupling member side locking portions 150a configure inward flanges. Therefore, the anchor side locking portions 115a and the coupling member side locking portions 150a interfere with each other and the bending operation wires 44 connected to the respective wire anchors 117 are regulated from moving to the distal end side.

In the anchor locking holes 150, the coupling member side locking portions 150a, which are plural concave portions, are provided in parallel. Therefore, the anchor side locking portions 118a of the wire anchoring tubes 118 interfere with any one of the coupling member side locking portions 150a. In other words, the connection of the respective wire anchors 117 and the respective coupling members 134 and 135 is first functional connection according to the present embodiment.

The anchor side locking portions 115a and the coupling member side locking portions 150a configure bending operation wire locking and connecting means. Moreover, a wire connecting mechanism is configured by the wire connection plate 108, the respective anchor side locking portions 118a, the respective coupling member side locking portions 150a, and the second guide plate 140.

As described above, the two coupling members 134 form a pair to be coupled to both the ends of the UD chain 136 and the two coupling members 135 form a pair to be coupled to the RL chain 137. The respective chains 136 and 137 are tugged and loosened in association with each other according to the rotating of the respective bending operation knobs 19 of the main operation portion 18, whereby the respective coupling members 134 and 135 move forward and backward in the distal end direction and the proximal end direction in the grasping portion 17. At the point, the coupling members 134 and 135 forming a pair move forward and backward in opposite directions.

Therefore, since the two bending operation wires 44 coupled by the UD side coupling member 134 and the wire anchor 117 bend the bending portion 9 up and down, the bending operation wires 44 are tugged and loosened in association with the UD side coupling member 134. At the point, when one bending operation wire 44 is tugged, the other bending operation wire 44 is loosened.

In the bending portion 9, since the bending pieces 40 in the inside are rotated in a tugging direction of the bending operation wire 44 only by the tugging by one bending operation wire 44, tension is not given to the other bending operation wire 44 forming the pair. Therefore, in order to tug the wire anchor 117, to which one on the tugged side of the two UD side coupling members 134 is connected, in the proximal end direction, the anchor side locking portion 118a is locked by the coupling member side locking portion 150a not to move to the distal end side.

The same applies to the two bending operation wires 44 forming a pair according to the coupling of the RL side coupling member 135 and the wire anchor 117. In other words, the same action is performed in left and right bending of the bending portion 9.

Thus, the respective chains 136 and 137 operate in association with each other according to the rotating operation of the respective bending operation knobs 19 and the respective bending operation wires 44 connected to the respective coupling members 134 and 135 are tugged and loosened, whereby the bending portion 9 of the endoscope 2 is bent in the four directions, i.e., the up, down, left, and right directions.

As shown in FIG. 86, the docking of the connector cover 15 is completed in a state in which the connector cover 15 is pushed into the motor box 16 side. The operation for pushing in the connector cover 15 to the motor box 16 side is a second action according to the present embodiment.

When the connector cover 15 is pushed into the motor box 16 as the second action, as shown in FIGS. 87 to 90, the four engaging convex portions 127 disposed on the sides of the motor box 16 are guided to the respective slope surfaces 94a and 94b from the respective guide grooves 92a and 92b formed in the inner side surfaces of the connector cover 15 and are inserted into the engaging holes 91a and 91b corresponding thereto.

Figure 87:
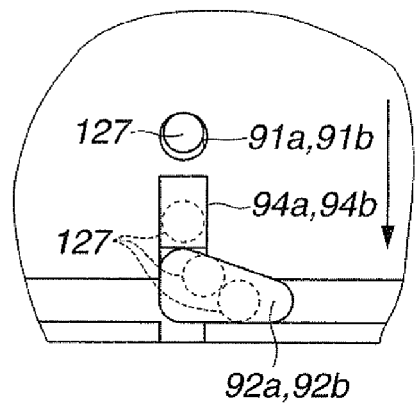
FIG. 87 is a diagram for explaining a state in which the engaging convex portion of the motor box is inserted in an engaging hole while being guided by a guide groove of the connector cover and an inclined surface according to the embodiment.

Specifically, as shown in FIG. 87, according to the movement of the connector cover 15, the respective engaging convex portions 127 are sent to the respective slope surfaces 94a and 94b along the slopes formed on the upper side of the guide grooves 92a and 92b corresponding thereto. For the respective guide grooves 92a and 92b, a groove shape is set in an allowable range not to prevent the movement of the respective engaging convex portions 127 when the connector cover 15 moves downward at the time when the wire connection plate 108 of the connector cover 15 is inserted into the grasping portion 17. In other words, even if there is slight backlash in the connector cover 15 and the wire connection plate 108 thereof, the connector cover 15 can be easily docked with the motor box 16.

Figure 88:
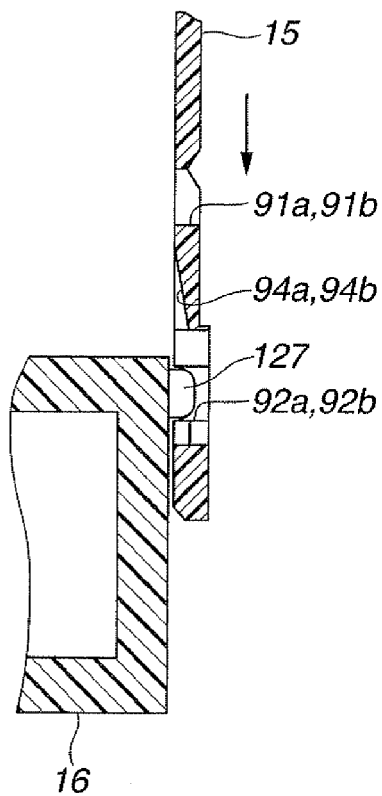
FIG. 88 is a diagram for explaining the state in which the engaging convex portion of the motor box is inserted in the engaging hole while being guided by the guide groove of the connector cover and the inclined surface according to the embodiment.

The engaging convex portions 127 are sent into the engaging holes 91a and 91b corresponding thereto while being guided linearly by the respective slope surfaces 94a and 94b. At the point, the respective slope surfaces 94a and 94b are inclined from the outer side of the inner side wall of the connector cover 15 to the inner side toward the respective engaging holes 91a and 91b. Therefore, as shown in FIGS. 88 to 90, the engaging convex portions 127 are inserted into the engaging holes 91a and 91b corresponding thereto from the guide grooves 92a and 92b. In other words, the side walls of the connector cover 15 slightly expand. The user can grasp, with a sense of click that occurs when the respective engaging convex portions 127 are inserted into the engaging holes 91a and 91b, that the docking (the coupling) of the connector cover 15 and the motor box 16 is completed.

Thus, the connector cover 15 is docked with the motor box 16.

As shown in FIG. 91, the respective engaging holes 91a and 91b are formed in an elliptical shape of hole surfaces slightly extended vertically with respect to the respective engaging convex portions 127 of a substantially columnar shape. In other words, the respective engaging convex portions 127 can freely travel in a distance of L8 in the figure in the respective engaging holes 91a and 91b. In other words, the connector cover 15 can travel the distance L8 with respect to the motor box 16.

This is for the purpose of adjusting the connector cover 15 subjected to a push-in force by providing clearance against the reaction by the respective bearings 97, the electric connector 99, the content holding body 103, and the respective bearing side elastic members 98, 102, and 106 interposed on the bottom surface of the connector cover 15 and surely perform docking of the connector cover 15 and the motor box 16.

In other words, a force moving away in a direction opposite in the push-in direction to the motor box 16 is applied to the connector cover 15 by the reaction of the respective bearing side elastic members 98, 102, and 106. A part of the side peripheral surfaces of the respective engaging convex portion 127 and a part of the inner peripheral surfaces forming the respective engaging holes 91a and 91b come into contact with each other with a predetermined force by the reaction.

Consequently, the connector cover 15 and the motor box 16 surely dock with each other in a generally fixed state while being subjected to the predetermined reaction.

When the connector cover 15 is docked with the motor box 16 in this way, the insertion portion side gear 96 and the motor gear 123 are meshed as the second functional connection according to the present embodiment and the electric connector 99 on the male side and the electric connector 125 on the female side are electrically connected as the third functional function according to the present embodiment.

The meshing of the insertion portion side gear 96 and the motor gear 123 and the electric connection of the electric connector 99 on the male side and the electric connector 125 on the female side is explained below more in detail.

First, the meshing of the insertion portion side gear 96 and the motor gear 123 as the second functional connection is explained with reference to FIGS. 92 to 99.

When the connector cover 15 is docked with the motor box 16, as indicated by a state shown in FIG. 92 (FIG. 95) to a state shown in FIG. 93, the insertion portion side gear 96 disposed in the connector cover 15 also moves to the motor cover 122 of the motor box 16 in a state in which the both end portions of the rotating shaft 84 are rotatably supported by the two bearings 97.

At the point, the ends of the four engaging leg portions 97a of the respective bearings 97 move to slide on the surface of the motor cover 122 and, as shown in FIG. 93, are guided to tilt surfaces 130a of the engaging holes 130 corresponding thereto formed in the motor cover 122.

When the connector cover 15 is pushed into the motor box 16, the engaging leg portions 97a of the respective bearings 97 are pierced through the engaging holes 130 corresponding thereto. At the point, as shown in FIGS. 94 and 96, since the respective bearing side elastic members 98 provided between the respective bearings 97 and the bottom surface of the connector cover 15 are elastically deformable in all the directions (on the figure, the bearings 97 shift in the right direction), even if the connector cover 15 slightly shifts, the four engaging leg portions 97a of the respective bearings 97 are drawn in and pierced through the engaging holes 130 corresponding thereto.

For example, even in a state in which the connector cover 15 is not parallel to the surface of the motor cover 122 of the motor box 16 as shown in FIG. 97, a state in which the bearings 97 shift vertically and the rotating shaft 84 is not parallel to the surface of the motor cover 122 of the motor box 16 as shown in FIG. 98, and the like, the two bearings 97 can independently move in all the directions because of deformation of the respective bearing side elastic members 98. Therefore, the four engaging leg portions 97a of the respective bearings 97 can be drawn in and pierced through the engaging holes 130 corresponding thereto.

In other words, the respective four engaging leg portions 97a of the respective bearing 97 are pierced through the engaging holes 130 corresponding thereto of the motor cover 122 and positioned on the surface of the motor cover 122.

In a state in which the connector cover 15 is docked with the motor box 16, the respective bearings 97 is pressed against the motor cover 122 by the reaction of the respective bearing side elastic members 98. In the state in which the bearings 97 are pressed toward the motor cover 122 by the bearing side elastic member 98, the insertion portion side gear 96 and the motor gear 123 mesh with each other via the rotating shaft 84. The rotating shaft 84 is rotatably supported by the bearings 97 with clearance. The clearance is set to a dimension with which the meshing of the respective gears 96 and 123 is maintained. Moreover, a positional relation of the respective gears 96 and 123 is in a range in which gear backlash does not occur.

Consequently, the insertion portion side gear 96 and the motor gear 123 exposed from the hole 131 (see FIG. 56) of the motor cover 122 surely mesh with each other. In the present embodiment, as shown in FIGS. 99 and 100, the insertion portion side gear 96 and the motor gear 123 are meshed in a state in which a center $O_1$ as a rotation axis of the insertion portion side gear 96 and a center $O_2$ as a rotation axis of the motor gear 123 are offset by a predetermined distance.

In other words, projecting positions of the four engaging leg portions 97a of the respective bearings 97, a setting position of the center $O_1$ as the rotation axis of the insertion portion side gear 96, which is a center position of the rotating shaft 84 that is rotatably held by the respective bearings 97, forming positions of the respective engaging holes 130 of the motor cover 122, and a setting position of the center $O_2$ as the rotation axis of the motor gear 123 of the motor 124 are determined such that the rotation axis (the center $O_1$) of the insertion portion side gear 96 and the rotation axis (the center $O_2$) of the motor gear 123 are offset by the predetermined distance.

When an offset amount of the rotation axis (the center $O_1$) of the insertion portion side gear 96 and the rotation axis (the center $O_2$) of the motor gear 123 is zero (0) as shown in FIG. 101, it is likely that gear tops of the respective gears 96 and 123 come into contact with each other and the insertion portion side gear 96 and the motor gear 123 do not surely mesh each other. Therefore, in the present embodiment, the technique described above is applied.

A rotation transmitting mechanism for driving to rotate the rotating cylinder 51 of the insertion portion main body 10 is configured by the insertion portion side gear 96, the two bearings 97 in which the bearing side elastic members 98 for rotatably holding the rotating shaft 84 in which the insertion portion side gear 96 is disposed, the respective engaging holes 130 formed in the motor cover 122 for positioning of the two bearings 97, and the motor gear 123 that transmits a rotation driving force to the insertion portion side gear 96 explained above.

Consequently, the rotation driving force of the motor 124 is transmitted to the insertion portion side gear 96 via the motor gear 123. The rotation driving force drives to rotate the rotating cylinder 51 connected to the rotating shaft 84 via the mouthpiece 83 around a predetermined axis. In the present embodiment, the rotation driving force of the motor 124 is transmitted from the proximal end side to the distal end side of the rotating cylinder 51 to rotate the entire rotating cylinder 51. However, the present invention is not limited to this. For example, the rotation driving force of the motor 124 may be transmitted in any position between the distal end and the proximal end of the rotating cylinder 51 to rotate the entire rotating cylinder 51.

In the configuration described above, regardless of the rotary self-propelled endoscope in the past, it is considered preferable that an insertion portion and an operation portion are detachably attachable to a medical endoscope from the viewpoints of storability in nonuse and sterilization and disinfection workability after use.

However, when the insertion portion and the operation portion are detachably attachable, the rotary self-propelled endoscope in the past has to be configured such that a rotation driving force can be surely transmitted from the operation portion side to a rotating cylinder rotatably disposed on an outer periphery of the insertion portion. In other words, in the rotary self-propelled endoscope, if a sufficient rotation driving force is not transmitted to the rotating cylinder, insertability of insertion portion into the body cavity is reduced.

Therefore, in the present embodiment, it is possible to adopt a rotary self-propelled endoscope 2 according to the present embodiment in which the insertion portion (in the present embodiment, the endoscope insertion portion with housing case 6) and the operation portion 7 are detachably attachable and a rotation driving force is surely transmitted from the operation portion 7 side to the rotating cylinder 51 of the insertion portion 6.

Next, electric connection of the electric connector 99 on the male side and the electric connector 125 on the female side as the third functional connection is explained with reference to FIGS. 102 to 105.

Figure 102:
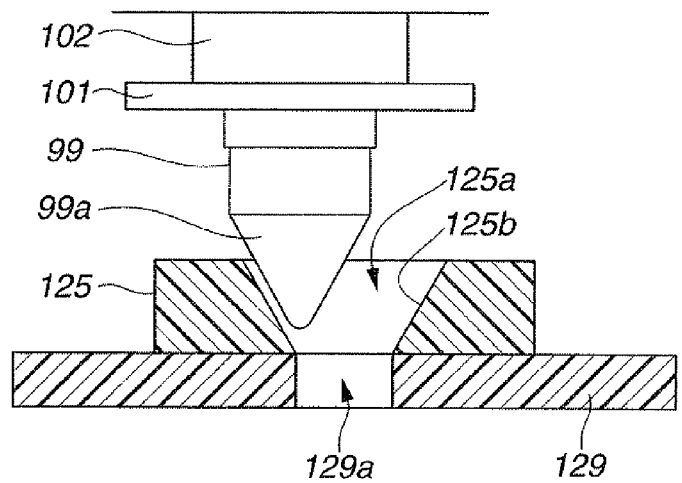
FIG. 102 is a diagram for explaining actions of a projecting portion of an electric connector on a male side and the fastened elastic member in connection of the electric connector on the male side and the electric connector on the female side according to the embodiment.
Figure 103:
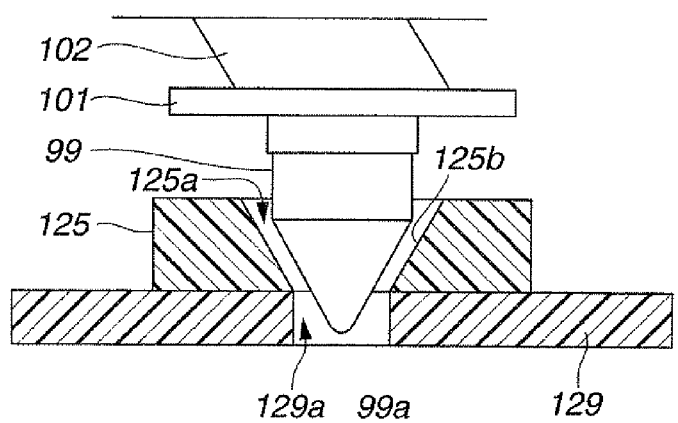
FIG. 103 is a diagram for explaining the actions of the projecting portion of the electric connector on the male side and the fastened elastic member in connection of the electric connector on the male side and the electric connector on the female side according to the embodiment.
Figure 104:
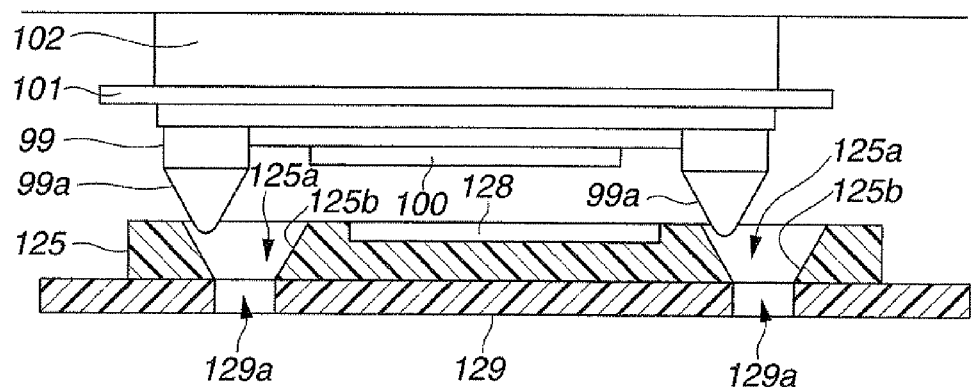
FIG. 104 is a diagram for explaining the actions of the projecting portion of the electric connector on the male side and the fastened elastic member in connection of the electric connector on the male side and the electric connector on the female side according to the embodiment.
Figure 105:
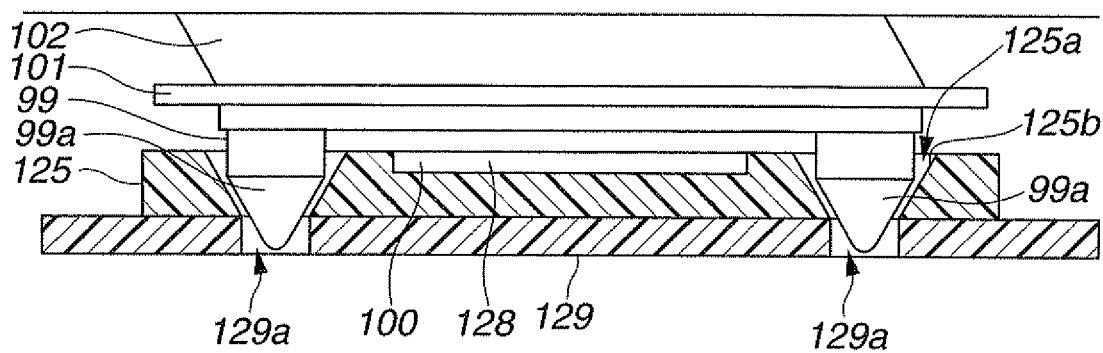
FIG. 105 is a diagram for explaining the actions of the projecting portion of the electric connector on the male side and the fastened elastic member in connection of the electric connector on the male side and the electric connector on the female side according to the embodiment.

When the connector cover 15 is docked with the motor box 16, as indicated by a state shown in FIG. 102 to a state shown in FIG. 103 and a state shown in FIG. 104 to a state shown in FIG. 105, the electric connector 99 on the male side disposed on the bottom surface of the connector cover 15 via the elastic member 102 also moves toward the electric connector 125 on the female side exposed in the motor cover 122 of the motor box 16 and is connected to the electric connector 125.

At the point, the two projecting portions 99a of the electric connector 99 are inserted in the engaging holes 125a formed in the electric connector 125 corresponding thereto. At the point, the slopes of the respective projecting portions 99a of a substantially pyramid shape of the electric connector 99 come into contact with the slope portions 125b of the engaging holes 125a and are drawn to be fit in the engaging holes 125a.

At the point, like the respective bearings 97, since the elastic member 102 interposed between the electric connector 99 and the connector cover 15 are deformable in all the directions, the electric connector 99 on the male side is surely connected to the electric connector 125 on the female side.

In other words, as indicated by a state shown in FIG. 104 to a state shown in FIG. 105, the connector portion 100 of the electric connector 99 and the connector portion 128 of the electric connector 125 come into electric contact and a transmission path for various electric signals and electric power supply is established. The electric connectors 99 and 125 configure a transmission path connecting mechanism.

Consequently, instruction signals of the various switches 21 provided in the main operation portion 18 shown in FIG. 1 and driving power of the light source 34 such as the LED, which is one of the electric devices built in the distal end portion 8 shown in FIG. 2, and the image pickup device 31, which is one of the electric devices, are supplied from the main operation portion 18 of the operation portion 7 and the motor box via the connector cover 15 and the insertion portion main body 10 of the endoscope insertion portion with housing case 6.

Like the respective bearings 97, the two projecting portions 103a of the content holding body 103 are pierced through the engaging holes 132 (see FIG. 56) corresponding thereto of the motor cover 122. Since the connector side elastic member 106 interposed between the content holding body 103 and the bottom surface of the connector cover 15 is deformed in all the directions, the content holding body 103 also easily fits in the engaging holes 132 to which the two projecting portions 103a correspond.

The content holding body 103 is fixed in a state in which the content holding body 103 is pressed against the surface of the motor cover 122 of the motor box 16 by the elastic deformation of the connector side elastic member 106.

As explained above, in the endoscope 2 of the endoscope system 1 according to the present embodiment, as shown in FIG. 106, since the connector cover 15 is docked with the motor box 16 before use, the endoscope insertion portion with housing case 6 and the operation portion 7 are coupled. In FIG. 106, the insertion assisting tool 11, the housing case main body 12, and the two guide tubes 13 and 14 configuring a part of the endoscope insertion portion with housing case 6 are not shown. However, the connection cylinder 79 explained with reference to FIGS. 19 and 20 is connected to the connector cover 15.

In the endoscope system 1 according to the present embodiment configured as explained above, the distal end portion 8, the bending portion 9, and the insertion portion main body 10 and the insertion assisting tool 11 to the connector cover 15 that cover the components are configured as the endoscope insertion portion with housing case 6 (see FIG. 1). The endoscope insertion portion with housing case 6 is a disposable portion that is disposed in every use. In the present embodiment, the endoscope insertion portion with housing case 6 is disposable. However, the endoscope insertion portion with housing case 6 can be reused if sterilization and disinfection are sufficiently performed after use.

Actions of the endoscope insertion portion with housing case 6 with respect to the endoscope system 1 are explained below. In the following explanation, a large intestine inspection is explained as an example mainly with reference to FIGS. 107 to 110.

First, when the insertion portion of the endoscope 2 is to be inserted through to, for example, the cecum of the large intestine, the endoscope system 1 according to the present embodiment shown in FIG. 107 is prepared by medical personnel as predetermined. An operator, who is a doctor, inserts the insertion assisting tool 11 from, for example, the anus of a patient lying on a bed. The insertion portion is housed in the housing case main body 12 in a bent state shown in FIG. 107.

As shown in FIG. 108, the aberration preventing portion 54 comes into contact with the hip 510 in the vicinity of the anus 501 of the patient, whereby only the insertion tube 53 of the insertion assisting tool 11 is inserted in the intestinum rectum 502 from the anus 501. In other words, the insertion assisting tool 11 is prevented from being entirely inserted into the intestinum rectum 502 by the aberration preventing portion 54. At the point, it is desirable that the operator fixes the aberration preventing portion 54 to the hip 510 of the patient with a tape or the like.

When the endoscope system 1 is set in such a state, the operator grasps the grasping portion 17 of the operation portion 7 and rotates the rotating cylinder 51 around an axis in a predetermined direction according to foot manual operation of the foot switch 25 or hand manual operation of the advancing and retracting switch 120 in the main operation portion 18 shown in FIG. 1.

The two thrust generating members 70a and 70b disposed in the guide tube fixing members 64 of the housing case main body 12 are always in press contact with the concave portion of the spiral shape portion 51a of the rotating cylinder 51 as shown in FIG. 17. In other words, the rotating cylinder 51 is given predetermined frictional resistance in substantially the center of the respective holes 77 of the thrust generating members 70a and 70b.

In the contact state, the operator brings the motor 124 disposed in the motor box 16 of the operation portion 7 into a rotation driving state by the foot manual operation or the hand manual operation. Then, torque is transmitted to the rotating cylinder 51 from the proximal end portion to the distal end side and the entire rotating cylinder 51 rotates in a predetermined direction around an axis as indicated by an arrow in FIG. 108.

Consequently, in a contact portion of a concave portion between the respective holes 77 of the thrust generating members 70a and 70b and the spiral shape portion 51a of the rotating cylinder 51, thrust for moving the rotating cylinder 51 forward like the movement of the male screw with respect to the female screw is generated.

In the rotating cylinder 51 in which the thrust is generated while being rotated, the mouthpiece 50 fastened to the distal end shown in FIG. 2 presses the third mouthpiece 48 at the proximal end of the bending portion 9. Consequently, the insertion portion including the distal end portion 8 and the bending portion 9 advances to the depth in the large intestine via the distal end side guide tube 13 and the insertion assisting tool 11 with the thrust of the rotating cylinder 51.

At the point, the operator can softly grasp the holding tube 55 of the insertion assisting tool 11 and move the insertion portion toward the depth of the large intestine only with the thrust generated by the respective thrust generating members 70a and 70b without grasping and pushing the insertion portion.

Since the two first and second thrust generating members 70a and 70b are spaced apart at the predetermined distance in the guide tube fixing member 64, the insertion portion is held in a stable state in the major axis direction and the thrust for moving the insertion portion is efficiently generated.

In addition, the spiral shape portion 51a formed on the outer surface of the rotating cylinder 51 comes into contact with the intestinal wall. At the point, a state of contact of the spiral shape portion 51a formed in the rotating cylinder 51 and the plicae of the intestinal wall is a relation between the male screw and the female screw. At the point, the rotating cylinder 51 smoothly moves forward with the thrust generated by the respective thrust generating members 70a and 70b in the guide tube fixing member 64 and the thrust generated by the contact with the plicae of the intestinal wall.

Then, the insertion portion advances from the intestinum rectum 502 to the sigmoid colon 503 with the thrust. Then, the distal end portion 8 and the bending portion 9 reach the sigmoid colon 503 as shown in FIG. 109. At the point, the operator operates the two bending operation knob 19 (see FIG. 1) in the main operation portion 18 while looking at an endoscopic image displayed by the monitor 4 and bends the bending portion 9 to match a bending state of the sigmoid colon 503.

With the bending operation of the bending portion 9, the operator can smoothly pass the insertion portion, to which the thrust is given, through the sigmoid colon 503, insertion into which is considered difficult.

The insertion portion is always given the thrust generated by the thrust generating members 70a and 70b in the guide tube fixing member 64 and the contact length of the spiral shape portion 51a and the intestinal wall increases as the insertion portion is inserted into the depth of the large intestine.

Therefore, even in a state in which a part of the spiral shape portion 51a is in contact with the plicae of the sigmoid colon 503, a state in which the insertion portion bends complexly, and the like, the stable thrust in the large intestine depth direction can be obtained. In addition, since the insertion portion has sufficient flexibility, the insertion portion smoothly moves forward along the intestinal wall without changing a traveling state of the sigmoid colon 503, a position of which easily changes.

The insertion portion including the rotating cylinder 51 in the rotated state passes the sigmoid colon 503 and, then, smoothly moves forward along walls of a bent portion that is a boundary of the sigmoid colon 503 and the descending colon 504 with poor mobility, the spleen bend 505 that is a boundary of the descending colon 504 and the transverse colon 506 with rich mobility, and the hepatic bend 507 that is a boundary of the transverse colon 506 and the ascending colon 508. As shown in FIG. 110, the insertion portion reaches, for example, in the vicinity of the cecum 509 that is a target region.

In the case of the insertion operation, when the distal end portion 8 reaches the respective bent portions (the spleen bend 505 and the hepatic bend 507), in the same manner as described above, the operator operates the two bending operation knobs 19 in the main operation portion 18 and bends the insertion portion to match bending states of the respective regions while looking at an endoscopic image displayed by the monitor 4.

After determining that the distal end portion 8 has reached in the vicinity of the cecum 509 according to the endoscopic image on the monitor 4, the operator once stops the rotation of the rotating cylinder 51 with the foot manual operation or the hand manual operation. Then, the operator performs, with the foot manual operation of the foot switch 25 or the hand manual operation of the advancing and retracting switch 120 in the main operation portion 18, operation for rotating the rotating cylinder 51 in a direction opposite to the rotating direction around the axis at the time of insertion.

In other words, the operator reverses the rotating cylinder 51 from the rotation at the time of insertion and performs a large intestine inspection while moving the insertion portion backward in a direction for pulling out the distal end portion 8 from the depth of the large intestine and in the vicinity of the cecum 509. Even at the point, the operator can move, without touching the insertion portion, the insertion portion backward with the thrust generated by the contact of the rotating cylinder 51 with the respective thrust generating members 70a and 70b and the plicae of the intestinal wall.

The distal end portion 8 and the bending portion 9 are pulled to the rotating cylinder 51 by the convexo-concave portion 50a of the mouthpiece 50 at the distal end of the rotating cylinder 51 that engages with the projecting portion 48a of the third mouthpiece 48 provided at the proximal end of the bending portion 9. Therefore, the entire insertion portion moves backward with the thrust of the rotating cylinder 51.

When the distal end portion 8 of the insertion portion reaches the insertion assisting tool 11, the operator pulls out the insertion portion from the anus 501 of the patient together with the insertion assisting tool 11 and finishes the large intestine inspection.

At the point, the insertion portion is given backward thrust by the respective thrust generating members 70a and 70b present in the guide tube fixing member 64 and is housed in the housing case main body 12 while bending to an original state shown in FIG. 26.

In the endoscope 2 according to the present embodiment, the respective guide tubes 13 and 14 that couples the housing case main body 12 and the insertion assisting tool 11 or the operation portion 7 to communicate with each other have flexibility. Therefore, even if the housing case main body 12 is placed and fixed, a grasping position of the operation portion 7 by the operator and a position of the insertion assisting tool 11 that approaches the anus of a patient are not limited and a desired position can be moved in a certain degree of an allowable range.

In other words, since the distal end side guide tube 13 that connects the insertion assisting tool 11 and the housing case main body 12 is a flexible tube body, it is unnecessary to fix a positional relation between the anus of the patient and the housing case main body 12. A degree of freedom of the operation portion 7 is not limited either because of the flexibility of the operation portion side guide tube 14.

In the case of, for example, the large intestine inspection described above, it is likely that because of the rotating of the rotating cylinder 51, twist stress occurs in the insertion portion that moves forward and backward. However, in the endoscope system 1 according to the present embodiment, a distance between the plate bodies 61 and 62 in the housing case main body 12 is smaller than two times of a diameter of the convex portion that is a largest outer diameter of the spiral shape portion 51a of the rotating cylinder 51 forming the external shape of the insertion portion. Therefore, the insertion portion is prevented from changing to a ring shape in the housing case main body 12 because of the twist stress.

In the respective guide tubes 13 and 14, since an inner diameter of each of the guide tubes 13 and 14 is also smaller than two times of an outer diameter (a diameter) of the convex portion that is the maximum outer diameter of the spiral shape portion 51a of the rotating cylinder 51, the insertion portion is prevented from changing to a ring shape because of the twist stress. Therefore, the insertion portion is smoothly rotated around an axis in the housing case main body 12 and in the distal end side guide tube 13.

Since the housing case main body 12 and the respective guide tubes 13 and 14 are formed of a transparent or semi-transparent material, the operator can visually check the movement of the insertion portion, in particular, a rotation state of the rotating cylinder 51.

Moreover, since the connection portions of the insertion assisting tool 11 and the distal end side guide tube 13, the housing case main body 12, and the operation portion side guide tube 14 are water-tightly held, for example, liquid such as soil in the large intestine is prevented from scattering in an operating room. Therefore, the endoscope insertion portion with housing case 6 has a configuration excellent in terms of sanitation.

Since the insertion assisting tool 11 prevents the insertion portion before insertion into the body cavity from being subjected to resistance such as tightening by the anus 501 of the patient, it is possible to reduce occurrence of bending and twist due to the rotation is prevented. Moreover, the insertion assisting tool 1 prevents the insertion portion from coming into direct contact with the anus 501 when the insertion portion is introduced into the large intestine. Therefore, since the insertion portion with high flexibility is not subjected to resistance such as tightening by the anus 501, introduceability into the large intestine is improved.

The first and second thrust generating members 70a and 70b disposed in the insertion assisting tool 11 can generate thrust in the rotating cylinder 51 of the endoscope system 1 and improve introduceability and insertability of the rotating cylinder 51 into the body cavity, i.e., the large intestine. In the rotating cylinder 51, the two first and second thrust generating members 70a and 70b are provided in the guide tube fixing member 64, whereby a position in the major axis direction in the guide tube fixing member 64 is stabilized in substantially the center. Therefore, thrust for progress by an equal pressing force from the first and second thrust generating members 70a and 70b is efficiently generated.

As explained above, in the rotary self-propelled endoscope 2 and the endoscope insertion portion with housing case 6 thereof according to the present embodiment, the insertion portion main body 10 before insertion into the test region and the rotating cylinder 51 can be smoothly inserted into the test region. Therefore, the rotary self-propelled endoscope 2 and the endoscope insertion portion with housing case 6 have a configuration extremely excellent in operability.

After, for example, the large intestine inspection described above is finished, since the endoscope insertion portion with housing case 6 according to the present embodiment is disposable, the medical personnel has to prevent the used endoscope insertion portion with housing case 6 from being reused. In detaching the endoscope insertion portion with housing case 6 from the operation portion 7, the medical personnel detaches the connector cover 15 from the motor box 16.

At the point, in the present embodiment, as shown in FIGS. 111 and 112, the connector cover 15 is folded to be broken in an outer side direction along a folding groove 85a extended to the front and rear on both outer side surfaces of the connector cover 15 and is detached from the motor box 16. Thus, the medical personnel can easily detach the endoscope insertion portion with housing case 6 and the operation portion 7.

Since the connector cover 15 is broken along the folding groove 85a, it is impossible to dock the connector cover 15 with the motor box 16 again. Consequently, the used endoscope insertion portion with housing case 6 is discarded as medical waste without being reused. As a result, the endoscope system 1 according to the present embodiment is excellent in terms of sanitation because the reuse of the contaminated endoscope insertion portion with housing case 6 is prevented. A projecting portion 15a shown in FIG. 1 that makes it easy for the user to grasp the side of the connector cover 15, in which the folding groove 85a is disposed, may be provided.

As explained above, the endoscope 2 of the endoscope system 1 according to the present embodiment is realized in a configuration in which the endoscope insertion portion with housing case 6 and the operation portion 7 are detachably attachable. In other words, in order to couple the endoscope insertion portion with housing case 6 and the operation portion 7, the connector cover 15 is docked with the motor box 16.

In this case, the endoscope 2 is configured such that the motor gear 123 of the motor 124 built in the motor box 16 and the insertion portion side gear 96 disposed in the connector cover 15 surely mesh with each other. In other words, the respective bearings 97 that rotatably holds the rotating shaft 84, in which the insertion portion side gear 96 is disposed, is allowed to freely move in a certain degree of range with respect to the connector cover 15 by the bearing side elastic member 98 pasted thereto. The engaging leg portions 97a of the respective bearings 97 are pierced into the engaging holes 130 corresponding thereto formed in the surface of the motor cover 122 and the bearings 97 are positioned in predetermined positions on the motor cover 122.

Consequently, the insertion portion side gear 96 disposed in the connector cover 15 surely meshes with the motor gear 123 of the motor 124. Since the respective bearings 97 are always urged to the motor cover 122 side by the elastic member, a state in which the teeth of the insertion portion side gear 96 and the motor gear 123 surely mesh with each other is maintained.

The endoscope 2 according to the present embodiment has a configuration excellent in terms of sanitation that does not need to be sterilized and disinfected because the endoscope insertion portion with housing case 6 and the operation portion 7 are detachably attachable and the used endoscope insertion portion with housing case 6 is disposable. Even if the endoscope insertion portion with housing case 6 is reusable, since the endoscope insertion portion with housing case 6 and the operation portion 7 can be separately sterilized and disinfected, it is easy to sterilize and disinfect the endoscope insertion portion with housing case 6 and the operation portion 7 of the endoscope 2 and a burden on the user can be reduced.

When the endoscope insertion portion with housing case 6 and the operation portion 7 are coupled, in the four bending operation wires 44 for bending the bending portion 9 by tugging and loosening the bending portion 9, the wire anchors 117 provided at the respective ends thereof are simultaneously (at a time) connected the respective coupling members 134 and 135 corresponding thereto in the grasping portion 17 of the operation portion 7. Therefore, in the rotary self-propelled endoscope according to the present embodiment, it is easy to connect the endoscope insertion portion with housing case 6 and the operation portion 7, convenience of use is improved, and a mechanism for surely performing bending operation of the bending portion 9 in association with the bending operation knob 19 is configured.

In a state in which the endoscope insertion portion with housing case 6 and the operation portion 7 are coupled, the respective electric connectors 99 and 125 for supplying electric power to the image pickup device 31 and the light source 34 disposed in the distal end portion 8 and exchanging various signals are electrically connected surely.

As a result of the above, in the endoscope 2 according to the present embodiment even if the endoscope insertion portion with housing case 6 and the operation portion 7 are configured to be detachably attachable, it is possible to attach and detach, simultaneously (at a time) with the attachment and detachment operations of the endoscope insertion portion with housing case 6 and the operation portion 7, the respective gears 96 and 123 that transmit a rotation driving force to the rotating cylinder 51, the wire anchors 117 of the plural bending operation wires 44 for bending the bending portion 9 and the respective coupling members 134 and 135, and the respective electric connectors 99 and 125.

The invention described in the embodiment is not limited to the embodiment. Besides, it is possible to carry out various modifications without departing from the spirit of the invention at an implementation stage. Moreover, inventions at various stages are included in the embodiment. Various inventions can be extracted according to appropriate combinations in the disclosed plural elements.

For example, even if several elements are deleted from all the elements described in the embodiment, when the problem described in the section of the problem to be solved by the invention can be solved and the effects described in the effect of the invention can be obtained, the configuration from which the elements are deleted can be extracted as an invention.

The invention described above has characteristics of notes described below.

(Note 1)

An endoscope including:

an insertion portion including a bending portion;

an operation portion separate from the insertion portion;

a bending operation wire that is inserted through the insertion portion and used for bending the bending portion in a predetermined direction with tugging in a forward/backward tugging direction; and a connecting mechanism that makes it possible to couple the insertion portion and the operation portion in a manner in which the bending wire is freely tugged in the operation portion.

(Note 2)

The endoscope according to note 1, wherein the connecting mechanism is configured to couple the insertion portion and the operation portion in the forward/backward tugging direction, whereby the bending wire is guided to and hooked on a bending wire locking member that moves forward and backward in the tugging direction in association with operation of an operation lever provided in the operation portion.

(Note 3)

The endoscope according to note 1, wherein the connecting mechanism is configured to couple the insertion portion and the operation portion in the forward/backward tugging direction, whereby the bending wire is moved forward and backward in the tugging direction and guided to and hooked on any one of concave plural portions provided side by side in the tugging direction in a bending wire locking member including the concave portions in association with operation of an operation lever provided in the operation portion.

(Note 4)

The endoscope according to note 1, further including:

a wire connection plate in which the connecting mechanism is provided in the insertion portion and a proximal end portion of the bending wire is attached with movement in directions other than the forward/backward tugging direction substantially regulated;

a wire connection plate engaging portion that is provided in the operation portion and with which the wire connection plate can be engaged when the insertion portion and the operation portion are coupled; and a bending wire locking member that moves forward and backward in the tugging direction in association with operation of an operation lever provided in the operation portion and movement in directions other than the forward/backward tugging direction is substantially regulated and on which the proximal end portion of the bending wire can be hooked when the wire connection plate is engaged with the wire connection plate engaging portion.

(Note 5)

An endoscope including:

an insertion portion including a bending portion;

an operation portion that has a bending operation knob for bending the bending portion in a predetermined direction and to which the insertion portion is detachably attached;

plural bending operation wires that are inserted through the insertion portion and used for bending the bending portion in the predetermined direction with tugging and loosening; and a wire connecting mechanism that simultaneously connects the plural bending operation wires to the operation portion when the insertion portion and the operation portion are coupled.

(Note 6)

The endoscope according to note 5, wherein the connecting mechanism includes:

plural anchors connected to respective ends of the plural bending operation wires;

a wire connection plate that is disposed in the insertion portion and holds the plural anchors to freely move forward and backward;

plural bending wire locking members that are disposed in the operation portion and move forward and backward in association with operation of the bending operation knob and in which locking holes for locking the anchors are formed; and a guide plate that is disposed in the operation portion and guides the plate body in a predetermined direction, wherein when the insertion portion and the operation portion are coupled, the guide plate guides the plate body in the predetermined direction, whereby the plural anchors are simultaneously inserted in the locking holes corresponding thereto of the plural bending wire locking members.

(Note 7)

The endoscope according to note 6, wherein the wire connection plate has a convex portion projecting from a side, the guide plate has a cutout for guiding the convex portion, and when the insertion portion and the operation portion are coupled, the convex portion moves along the cutout, whereby the wire connection plate moves toward the bending wire locking member and the plural anchors are simultaneously inserted in the locking holes corresponding thereto.

(Note 8)

The endoscope according to note 7, wherein the guide plate has a slope portion in which the cutout is formed and tilts toward the bending wire locking member, and in the wire connection plate, the convex portion is guided to move in a direction toward the bending wire locking member along the slope portion of the guide plate in addition to the movement in the forward/backward direction.

(Note 9)

A rotary self-propelled endoscope, wherein the insertion portion of the endoscope according to any one of notes 1 to 8 includes a spiral tube that has a spiral shape portion formed on a surface thereof and is rotatable around an axis.

(Note 10)

A rotary self-propelled endoscope including:

an insertion portion including an insertion portion main body having a bending portion on a distal end side thereof and a rotating cylinder externally fit in the insertion portion main body rotatably;

an operation portion separated from the insertion portion;

driving means that is provided in the operation portion and engages with the rotating cylinder to rotate the rotating cylinder with respect to the insertion portion main body;

a bending wire that is inserted through the insertion portion and used for bending the bending portion in a predetermined direction according to forward/backward tugging direction; and a coupling mechanism having first functional connection for enabling tugging operation for the bending wire in the operation portion and second functional connection for making it possible to transmit a rotation driving force of the driving means to the rotating cylinder, by coupling operation of connection portions each provided in the insertion portion and the operation portion.

(Note 11)

The rotary self-propelled endoscope according to note 10, wherein the coupling mechanism is configured to enable the first functional connection with first action for coupling connectors along the forward/backward tugging direction and enable the second functional connection with second action for coupling the connectors in a vertical direction with respect to the first action.

(Note 12)

The rotary self-propelled endoscope according to note 11, wherein the coupling mechanism has third functional connection for electrically connecting the insertion portion and the operation portion with the second action.

(Note 13)

The rotary self-propelled endoscope according to note 11 or 12, wherein the coupling mechanism is configured to guide, with the first action, the bending wire to and hook the bending wire on a bending wire locking member that moves forward and backward in association with operation of an operation lever provided in the operation portion.

(Note 14)

The rotary self-propelled endoscope according to any one of notes 11 to 13, wherein the coupling mechanism is configured such that a first gear coupled to the rotating cylinder provided on the insertion portion side and a second gear coupled to a rotating shaft of a driving motor come close to and mesh with each other with the second action.

(Note 15)

A rotary self-propelled endoscope including:

an insertion portion including a distal end portion, a bending portion, and a spiral tube that has a spiral shape portion formed on a surface thereof and is rotatable around an axis;

an operation portion that has a bending operation knob for bending the bending portion in a predetermined direction and to which the insertion portion is detachably attachable;

driving means that is disposed in the operation portion and gives a rotation driving force around an axis to the spiral tube;

a rotation transmitting mechanism that transmits the rotation driving force of the driving means to the spiral tube in a state in which the insertion portion and the operation portion are coupled;

plural bending operation wires that are inserted through the insertion portion and used for bending the bending portion in a predetermined direction with tugging and loosening;

a wire connecting mechanism that simultaneously connects the plural bending operation wires to the operation portion when the insertion portion and the operation portion are coupled; and a transmission line connecting mechanism that supplies electric power to an electric device disposed in the distal end portion and exchanges various signals in a state in which the insertion portion and the operation portion are coupled.

(Note 16)

The rotary self-propelled endoscope according to note 15, wherein the insertion portion includes a connector cover on a proximal end side of the spiral tube, the operation portion includes a box body detachably attachable to the connector cover, the rotation transmitting mechanism includes:

a first gear that is disposed in the box body and rotated by the driving means;

a cover body that configures one surface of the box body and has a hole for exposing the first gear and an engaging hole;

a second gear disposed in a rotating shaft connected to the spiral tube to which the rotation of the first gear is transmitted; and a bearing that is disposed in the connector cover via a bearing side elastic member, rotatably holds the rotating shaft, and includes an engaging leg projecting from a surface on an opposite side of the elastic member, and in a state in which the connector cover and the box body are coupled, the engaging leg is pierced through the engaging hole of the cover body and the bearing is positioned in a predetermined position on the cover body where the first gear and the second gear mesh with each other.

(Note 17)

The rotary self-propelled endoscope according to note 16, wherein, such that the engaging leg of the bearing is guided to and sent into the engaging hole, the cover body has an inclined surface, which is inclined into the motor box toward a proximal end direction, on a wall surface on a distal end side where the engaging hole is formed.

(Note 18)

The rotary self-propelled endoscope according to note 17, wherein, when the connector cover and the box body are coupled, an end of the engaging leg is moved by elastic deformation of the bearing side elastic member along the inclined surface of the engaging hole and the bearing is positioned in the predetermined position.

(Note 19)

The rotary self-propelled endoscope according to note 10, wherein the wire connecting mechanism includes:

plural anchors connected to respective ends of the plural bending operation wires;

a wire connection plate that is disposed in the insertion portion and holds the plural anchors to freely move forward and backward;

plural bending wire locking members that are disposed in the operation portion and move forward and backward in association with operation of the bending operation knob and in which locking holes for locking the anchors are formed; and a guide plate that is disposed in the operation portion and guides the plate body in a predetermined direction, and when the insertion portion and the operation portion are coupled, the guide plate guides the plate body in the predetermined direction, whereby the plural anchors are simultaneously inserted in the locking holes corresponding thereto of the plural bending wire locking members.

(Note 20)

The rotary self-propelled endoscope according to note 19, wherein the wire connection plate is a plate body of a C shape in section and has a convex portion projecting from a side thereof, the guide plate has a cutout for guiding the convex portion, and when the insertion portion and the operation portion are coupled, the convex portion moves along the cutout, whereby the wire connection plate moves toward the bending wire locking members and the plural anchors are simultaneously inserted in the locking holes corresponding thereto.

(Note 21)

The rotary self-propelled endoscope according to note 20, wherein the guide plate has a slope portion in which the cutout is formed and that tilts toward the bending wire locking members, and in the wire connection plate, the convex portion is guided to move in a direction toward the bending wire locking members along the slope of the guide plate in addition to the movement in the forward/backward direction.

(Note 22)

The rotary self-propelled endoscope according to note 16, wherein the transmission line connecting mechanism includes:

a first electric connector that is disposed in the connector cover via a connector side elastic member and has a conical projecting portion projecting from a connector surface; and a second electric connector that is exposed on the one surface of the box body and in which an engaging hole in which the projecting portion of the first electric connector is inserted is formed, and the projecting portion is inserted in the engaging hole, whereby a connection position of the first electric connector to the second electric connector is determined and an electric transmission line is established.

(Note 23)

The rotary self-propelled endoscope according to note 22, wherein the second electric connector has, on a hole peripheral surface forming the engaging hole, a slope portion for guiding the conical projecting portion of the first electric connector and sending the projecting portion into the engaging hole.

(Note 24)

The rotary self-propelled endoscope according to note 23, wherein, when the connector cover and the box body are coupled, the first electric connector is moved by elastic deformation of the connector side elastic member, the projecting portion is sent along the slope portion of the second connector, and an electric connection position of the first electric connector to the second connector is determined.

(Note 25)

An endoscope including:

an insertion portion including a distal end portion and a bending portion;

an operation portion that has a bending operation knob for bending the bending portion in a predetermined direction and to which the insertion portion is detachably attachable;

plural bending operation wires that are inserted through the insertion portion and is used for bending the bending portion in the predetermined direction with tugging and loosening;

a wire connecting mechanism that simultaneously connects the plural bending operation wires to the operation portion when the insertion portion and the operation portion are coupled; and a transmission line connecting mechanism that supplies electric power to an electric device disposed in the distal end portion and exchanges various signals in a state in which the insertion portion and the operation portion are coupled (Note 26)

The endoscope according to note 25, wherein the wire connecting mechanism includes:

plural anchors connected to respective ends of the plural bending operation wires;

a wire connection plate that is disposed in the insertion portion and holds the plural anchors to freely move forward and backward;

plural bending wire locking members that are disposed in the operation portion and move forward and backward in association with operation of the bending operation knob and in which locking holes for locking the anchors are formed; and a guide plate that is disposed in the operation portion and guides the plate body in a predetermined direction, and when the insertion portion and the operation portion are coupled, the guide plate guides the plate body in the predetermined direction, whereby the plural anchors are simultaneously inserted in the locking holes corresponding thereto of the plural bending wire locking members.

(Note 27)

The endoscope according to note 26, wherein the wire connection plate is a plate body of a C shape in section and has a convex portion projecting from a side thereof, the guide plate has a cutout for guiding the convex portion, and when the insertion portion and the operation portion are coupled, the convex portion moves along the cutout, whereby the wire connection plate moves toward the bending wire locking members and the plural anchors are simultaneously inserted in the locking holes corresponding thereto (Note 28)

The endoscope according to note 27, wherein the guide plate has a slope portion in which the cutout is formed and that tilts toward the bending wire locking members, and in the wire connection plate, the convex portion is guided to move in a direction toward the bending wire locking members along the slope portion of the guide plate in addition to the movement in the forward/backward direction.

(Note 29)

The endoscope according to note 28, wherein the transmission line connecting mechanism includes:

a first electric connector that is disposed in the connector cover via a connector side elastic member and has a conical projecting portion projecting from a connector surface; and a second electric connector that is exposed on the one surface of the box body and in which an engaging hole in which the projecting portion of the first electric connector is inserted is formed, and the projecting portion is inserted in the engaging hole, whereby a connection position of the first electric connector to the second electric connector is determined and an electric transmission line is established.

(Note 30)

The endoscope according to note 29, wherein the second electric connector has, on a hole peripheral surface forming the engaging hole, a slope portion for guiding the conical projecting portion of the first electric connector and sending the projecting portion into the engaging hole.

(Note 31)

The endoscope according to note 30, wherein, when the connector cover and the box body are coupled, the first electric connector is moved by elastic deformation of the connector side elastic member, the projecting portion is sent along the slope portion of the second connector, and an electric connection position of the first electric connector to the second connector is determined.

(Note 32)

A rotary self-propelled endoscope including:

an insertion portion that includes an insertion portion main body, a rotating cylinder externally fit to the insertion portion main body rotatably, and a gear coupled to the rotating cylinder and in which a rotating shaft of the rotating cylinder is born by a bearing portion supported by an elastic body; and an operation portion that is detachably attachable to the insertion portion main body and that includes an engaged portion with which an engaging portion provided in the bearing portion engages and a second gear with which a first gear coupled to the rotating cylinder meshes and that is coupled to an output shaft of driving means for generating a driving force for rotating the rotating cylinder.

(Note 33)

The rotary self-propelled endoscope according to note 32, wherein, when the insertion portion and the operation portion are coupled, the engaging portion provided in the bearing portion engages with the engaged portion and, then, the first gear coupled to the rotating cylinder meshes with the second gear coupled to the output shaft.

(Note 34)

The rotary self-propelling endoscope according to note 33, wherein a direction of engaging operation with the engaging portion provided in the bearing portion and meshing operation for the first gear coupled to the rotating cylinder and the second gear coupled to the output shaft are substantially identical, the engaging portion projects further to a side in the engaging operation direction than a meshing portion with the first gear coupled to the rotating cylinder in the second gear coupled to the output shaft, and the elastic body elastically deforms in the meshing operation direction, whereby the first gear coupled to the rotating cylinder and the second gear coupled to the output shaft mesh with each other.

(Note 35)

The rotary self-propelled endoscope according to any one of notes 32 to 34, wherein the operation portion has a connector portion in which the engaged portion and the second gear are disposed, and the operation portion has a connector portion in which the bearing portion and the first gear are disposed such that the insertion portion is coupled to the connector, whereby the engaging portion and the engaged portion are engaged, and the first gear coupled to the rotary cylinder and the second gear coupled to the output shaft mesh with each other.

(Note 36)

A rotary self-propelled endoscope including:

an insertion portion that has a spiral tube that has a spiral shape portion formed on a surface thereof and rotatable around an axis;

an operation portion to which the insertion portion is detachably attachable;

driving means that is disposed in the operation portion and gives a rotation driving force around an axis to the spiral tube; and a rotation transmitting mechanism that transmits the rotation driving force of the driving means to the spiral tube in a state in which the insertion portion and the operation portion are coupled.

(Note 37)

The rotary self-propelled endoscope according to note 36, wherein the insertion portion includes a connector cover on a proximal end side of the spiral tube, the operation portion includes a box body detachably attachable to the connector cover, the rotation transmitting mechanism includes:

a first gear that is disposed in the box body and rotated by the driving means;

a cover body that configures one surface of the box body and has a hole for exposing the first gear and an engaging hole;

a second gear disposed in a rotating shaft connected to the spiral tube to which the rotation of the first gear is transmitted; and a bearing that is disposed in the connector cover via an elastic member, rotatably holds the rotating shaft, and includes an engaging leg projecting from a surface on an opposite side of the elastic member, and in a state in which the connector cover and the box body are coupled, the engaging leg is pierced through the engaging hole of the cover body and the bearing is positioned in a predetermined position on the cover body where the first gear and the second gear mesh with each other.

(Note 38)

The rotary self-propelled endoscope according to note 37, wherein, such that the engaging leg of the bearing is guided to and sent into the engaging hole, the cover body has an inclined surface, which is inclined into the motor box toward a proximal end direction, on a wall surface on a distal end side where the engaging hole is formed.

(Note 39)

The rotary self-propelled endoscope according to note 38, wherein, when the connector cover and the box body are coupled, an end of the engaging leg is moved by elastic deformation of the elastic member along the inclined surface of the engaging hole and the bearing is positioned in the predetermined position.

What is claimed is:

1. An endoscope comprising:
an operation portion separate from and detachably attachable to the insertion portion, wherein the operation portion comprises a grasping portion and an operation lever;
a bending operation wire that is inserted through the insertion portion and used for bending the bending portion in a predetermined direction with ragging in a forward/backward tagging direction;
a connecting mechanism comprising a first connecting mechanism, the first connecting mechanism provided on a side of the insertion portion, the first connecting mechanism comprising:
a plate having a groove formed thereon; and
a wire anchor, the wire anchor comprising:
a connection portion which the bending operation wire is connected;
a locking plate portion that is lifted into the groove and is linearly guided to be allowed to advance and retract along the groove when a bending operation of the bending portion is performed,
and a projecting portion projecting in a outer peripheral direction of the wire anchor;
the connecting mechanism further comprising
a second connecting mechanism provided on a side of the grasping portion of the operation portion in a state where the insertion portion and the operation portion are not coupled and are separated from each other, the second connecting mechanism comprising a coupling member, the coupling member comprising
a concave portion, into which the wire anchor of the first connecting mechanism is fitted when the operation portion and the insertion portion are coupled, formed thereon, and movement of the projecting portion of the wire anchor fitted into the concave portion is regulated by wall surfaces forming the concave portion to thereby enable tugging of the bending operation wire,
where the coupling member is configured to move forward and backward in association with operation of the operation lever provided to the operation portion,
and where the connecting mechanism is configured to perform connection of the bending operation wire and the coupling member to coincide with coupling operation of the operation portion and the insertion portion, thereby allowing the coupling member to move proximally with respect to the insertion portion tug the bending operation wire in association with the operation of the operation lever so as to bend the bending portion.

2. The endoscope according to claim 1, wherein the coupling member is provided with a plurality of concave portions and the connecting mechanism is configured to cause the wire anchor to be engaged with any of the plurality of concave portions continuously formed to the coupling member, and connect the bending operation wire and the coupling member, in connection with the coupling operation of the operation portion and the insertion portion.

3. The endoscope according to claim 2, wherein the groove comprises:
   a groove in which the wire anchor is disposed to be movable forward and backward so as to substantially regulate movement in directions other than the direction of the tugging operation of the bending wires.

4. The endoscope according to claim 1, wherein the projecting portion is provided at a proximal end portion on an opposite side with respect to the connection portion, and the concave portion is an elongated hole which has a shape of a plurality of continuing ellipses on a surface of the coupling member with portions where the ellipses cross projecting to be opposed to a center of the hole.

5. The endoscope according to claim 1, comprising a chain which moves in association with rotation of the operation lever and the coupling member is connected to the chain and moves in accordance with movement of the chain.

\* \* \* \* \*

UNITED STATES PATENT AND TRADEMARK OFFICE
CERTIFICATE OF CORRECTION

Page 1 of 1

PATENT NO. : 8,858,428 B2
APPLICATION NO. : 12/168610
DATED : October 14, 2014
INVENTOR(S) : Hiroaki Miyoshi et al.

It is certified that error appears in the above-identified patent and that said Letters Patent is hereby corrected as shown below:

In the Claims

Column 52, line 36 (Claim 1, line 15) should read:

a connection portion to which the bending operation

Signed and Sealed this
Seventeenth Day of March, 2015

Michelle K. Lee
*Director of the United States Patent and Trademark Office*